United States Patent
Dantus et al.

(10) Patent No.: US 7,105,811 B2
(45) Date of Patent: Sep. 12, 2006

(54) CONTROL SYSTEM AND APPARATUS FOR USE WITH LASER EXCITATION OF IONIZATION

(75) Inventors: Marcos Dantus, Okemos, MI (US); Vadim V. Lozovoy, Okemos, MI (US)

(73) Assignee: Board of Trustees operating Michigan State Univesity, East Lansing, MI (US)

( * ) Notice: Subject to any disclaimer, the term of this patent is extended or adjusted under 35 U.S.C. 154(b) by 146 days.

(21) Appl. No.: 10/628,874

(22) Filed: Jul. 28, 2003

(65) Prior Publication Data

US 2004/0089804 A1 May 13, 2004

Related U.S. Application Data

(63) Continuation of application No. PCT/US02/02548, filed on Jan. 28, 2002.
(60) Provisional application No. 60/265,133, filed on Jan. 30, 2001.

(51) Int. Cl.
  *H01J 49/16* (2006.01)
(52) U.S. Cl. ........................................... 250/288
(58) Field of Classification Search ................ 250/288, 250/423 P, 281, 282
  See application file for complete search history.

(56) References Cited

U.S. PATENT DOCUMENTS

| | | | |
|---|---|---|---|
| 4,288,691 A | * | 9/1981 | Horton ......................... 250/281 |
| 5,526,171 A | | 6/1996 | Warren |
| 5,754,292 A | | 5/1998 | Kane et al. |
| 5,936,732 A | | 8/1999 | Smirl et al. |
| 6,042,603 A | | 3/2000 | Fisher et al. |
| 6,057,919 A | | 5/2000 | Machida et al. |
| 6,111,251 A | | 8/2000 | Hillenkamp |
| 6,130,426 A | | 10/2000 | Laukien et al. |
| 6,156,527 A | | 12/2000 | Schmidt et al. |
| 6,219,142 B1 | | 4/2001 | Kane |
| 6,296,810 B1 | | 10/2001 | Ulmer |
| 6,327,068 B1 | | 12/2001 | Silberberg et al. |
| 6,337,606 B1 | | 1/2002 | Brombaugh et al. |
| 6,421,154 B1 | | 7/2002 | Diels et al. |
| 6,573,493 B1 | * | 6/2003 | Futami et al. ............... 250/288 |
| 6,697,196 B1 | | 2/2004 | Suzuki |
| 6,723,991 B1 | * | 4/2004 | Sucha et al. .............. 250/341.1 |
| 2004/0145735 A1 | | 7/2004 | Silberberg et al. |
| 2004/0155184 A1 | | 8/2004 | Stockman et al. |
| 2004/0240037 A1 | | 12/2004 | Harter |
| 2004/0263950 A1 | | 12/2004 | Fermann et al. |

FOREIGN PATENT DOCUMENTS

| | | |
|---|---|---|
| WO | WO 99/57318 | 11/1999 |
| WO | WO 00/70647 | 11/2000 |
| WO | WO 01/54323 A2 | 7/2001 |
| WO | WO 02/061799 A2 | 8/2002 |

OTHER PUBLICATIONS

Teaching Laser to Control Molecules; Richard S. Judson et al.; Physical Review Letters; vol. 68, No. 10, pp. 1500–1503 (Mar. 9, 1992).

(Continued)

*Primary Examiner*—Kiet T. Nguyen
(74) *Attorney, Agent, or Firm*—Harness, Dickey & Pierce, P.L.C.

(57) ABSTRACT

A control system and apparatus for use with laser ionization is provided. In another aspect of the present invention, the apparatus includes a laser, pulse shaper, detection device and control system. A further aspect of the present invention employs a femtosecond laser and a mass spectrometer. In yet other aspects of the present invention, the control system and apparatus are used in MALDI, chemical bond cleaving, protein sequencing, photodynamic therapy, optical coherence tomography and optical communications processes.

50 Claims, 22 Drawing Sheets

OTHER PUBLICATIONS

Feedback–controlled femtosecond pulse shaping; T. Brixner, A. Oehrlein, M. Strehle, G. Gerber; Applied Physics B70, Laser and Optics (2000); pp. S119–S124.

Feedback Quantum Control of Molecular Electronic Population Transfer; Chemical Physics Leters; Christopher J. Bardeen et al.; (published prior to Oct. 4, 2002) (19 pages).

Compression Of Amplified Chirped Optical Pulses; Optics Communications; Donna Strickland et al.; vol. 55, No. 6; (Oct. 15, 1985), pp. 447–449.

Femtosecond laser pulse shaping by use of microsecond radio–frequency pulses; C.W. Hillegas et al.; Optics Letters, vol. 19, No. 10 (May 15, 1994), pp. 737–739.

Ultrabroadband Femtosecond Lasers; Christian Spielmann et al.; IEEE Journal Of Quantum Electronics, vol. 30, No. 4 (Apr. 1994); pp. 1100–1114.

Programmable Shaping of Femtosecond Optical Pulses by Use of 128–Element Liquid Crystal Phase Modulator; Andrew M. Weiner et al.; IEEE Journal Of Quantum Electronics, vol. 28, No. 4 (Apr. 1992), pp. 908–920.

Back–side–coated chirped mirrors with ultra–smooth broadband dispersion characterisitcs; N. Matuschek et al.; Applied Physics B Lasers and Optics (Sep. 6, 2000); pp. 509–522.

Femtosecond pulse shaping by an evolutionary algorithm with feedback; T. Baumert et al.; Applied Physics B Lasers and Optics (1997); pp. 779–782.

Adaptive real–time femtosecond pulse shaping; D. Meshulach et al.; vol. 15, No. 5/May 1998/J. Opt. Soc. Am. B., pp. 1615–1619.

Femtosecond pulse shaping by dynamic holograms in photorefractive multiple quantum wells; Y. Ding et al.; Optics Letters/vol. 22, No. 10/May 15, 1997, pp. 718–720.

Engineerable femtosecond pulse shaping by second–harmonic generation with Fourier synthetic quasi–phase–matching gratings; G. Imeshev et al.; Optics Letters/vol. 23, No. 11/Jun. 1, 1998, pp. 864–866.

Controlling the Future of Matter; Bern Kohler et al.; Acc. Chem. Res. 1995, 28, pp. 133–140.

High–Resolution, Ultrafast Laser Pulse Shaping and Its Applications; J. X. Tull et al.; Advances in Magnetic And Optical Resonance, vol. 20, pp. 1–65 (1997).

Femtosecond pulse shaping using spatial light modulators; A.M. Weiner; Review Of Scientific Instruments, vol. 71, No. 5 (May 2000) pp. 1929–1960.

Chemisry with Photons; W. S. Warren; SCIENCE vol. 262, Nov. 12, 1993, pp. 1008–1009.

Transform–Limited Pulses Are Not Optimal for Resonant Multiphoton Transitions; Nirit Dudovich et al.; Physical Review Letters, vol. 86, No. 1 (Jan. 1, 2001) pp. 47–50.

Laser scanning third–harmonic–generation microscopy in biology; D. Yelin et al.; Optics Express; Oct. 11, 1999/ vol. 5, No. 8, pp. 169–175.

Coherent quantum control of two–photon transitions by a femtosecond laser pulse; Doron Meshulach et al.; NATURE/vol 396/Nov. 19, 1998, pp. 239–242.

Selective Bond Dissociation and Rearrangement with Optimally Tailored, Strong–Field Laser Pulses; Robert J. Levis et al.; SCIENCE, vol. 292 (Apr. 27, 2001) pp. 709–713.

Femtosecond pulse shaping with a stratified diffractive structure; Frank Schreier et al.; Optics Communications 185 (2000) pp. 227–231.

Nonlinear limits to the information capacity of optical fibre communications; Partha P. Mitra et al.; NATURE/vol 411/ Jun. 28, 2001, pp. 1027–1030.

In vivo ultrahigh–resolution optical coherence tomography; W. Drexler et al.; Optics Letters; vol. 24, No. 17 (Sep. 1, 1999) pp. 1221–1223.

Mass spectrometry; McGraw–Hill Encyclopedia Of Science & Technology, $6^{th}$ Ed., pp. 492–502; 1987 (12 pages).

Coherent quantum control of multiphoton transitions by shaped ultrashort optical pulses; Doron Meshulach et al.; Physical Review A; vol. 60, No. 2 (Aug. 1999); pp. 1287–1292.

Nonlinear limits to the information capacity of optical fibre communications; Partha P. Mitra et al.; Nature/vol 411/Jun. 28, 2001, pp. 1027–1030.

Control of Chemical Reactions by Feedback–Optimized Phase–Shaped Femtosecond Laser Pulses; A. Assion et al.; SCIENCE; vol. 282 (Oct. 30, 1998) pp. 919–922.

Multiphoton Intrapulse Interference. 1. Control of Multiphoton Processes in Condensed Phases; Katherine A. Walowicz, Igor Pastirk, Vadim V. Lozovoy, and Marcos Dantus; American Chemical Society, J. Phys. Chem. A; Aug. 2002 (5 pages).

Measuring ultrashort laser pulses in the time–frequency domain using frequency–resolved optical gating; Rick Trebino et al.; 1997 American Institute Of Physics; Rev. Sci. Instrum. 68 (9), Sep. 1997, pp. 3277–3295.

Ambuguity of Ultrashort Pulses Retrieved From the Intensity Autocorrelation and Power Spectrum Traces; J.–H. Chung et al.; CERIAS Tech Report 2002–01, IEEE Journal on Selected Topics in Quantum Electronics, vol. 7, No. 4; Jul./Aug. 2001, pp. 656–666.

Measuring Ultrashort Laser Pulses Just Got A Lot Easier!; Rick Trebino et al.; Optics & Photonics News, pp. 23–25, Jun. 2001.

Coherent control of second harmonic generation using spectrally phase coded femtosecond waveforms; Z. Zheng, et al.; Chemical Physics 267, (2001); pp. 161–171.

Spectral phase correlation of coded femtosecond pulses by second–harmonic generation in thick nonlinear crystals; Z. Zheng et al.; Optics Letters/vol. 25, No. 13/Jul. 1, 2000, pp. 984–986.

Mass–Correlated Pulsed Extraction: Theoretical Analysis and Implementation With a Linear matrix–Assisted laser Desorption/Ionization Time of Flight Mass Spectrometer; Slava V. Kovtoun et al.; American Society for Mass Spectrometry, (2000); pp. 841–853.

Femtoscond laser mass spectroscopy of ferrocenes: Photochemical stabilization by bridge cyclopentadienyl rings?; M. Clara et al.; International Journal of Mass Spectrometry 203 (2000), pp. 71–81.

GeneticAlgorithm–v4.nb; Marcos Dantus; Oct. 2001 to simulate an adaptive genetic algorithm, pp. 1–7.

Abstract–Laser desorption/ionization mass spectrometry of peptides and proteins with particle suspension matrixes; M. Schurenberg et al.; Analytical Chemistry; 71 (1): 221–229; (Jan. 1, 1999); (1 page).

Abstract–Matrix–assisted laser desorption/ionisation, an experience; F. Hillenkamp et al.; International Journal Of Mass Spectrometry; 200 (1–3): 71–77 (Dec. 25, 2000); (1 page).

Abstract–Innovative pulse shaping for high–performance wireless TDMA; B. Natarajan et al.; IEEE Communications Letters; 5 (9): 372–374 (Sep. 2001); (1 page).

Abstract–20-fs pulse shaping with a 512-element phase-only liquid crystal modulator; H. Wang et al.; IEEE Journal Of Selected Topics In Quantum Electronics; 7 (4): 719–727 (Jul.–Aug. 2001); (1 page).

Abstract–Femtosecond quantum control; T Brixner et al.; Advances In Atomic, Molecular, And Optical Physics, vol. 46; 46: 1–54 (2001); (1 page).

Abstract–Photoselective adaptive femtosecond quantum control in the liquid phase; T Brixner et al.; Nature; 414 (6859): 57–60 (Nov. 1, 2001); (1 page).

Abstract–Interference effects in femtosecond spectroscopy; G Roberts; Philosophical Transcations Of The Royal Society Of London Series A–Mathematical Physical and Engineering Sciences; 360 (1794): 987–1021 (May 15, 2002); (1 page).

Abstract–Programmable chirp compensation for 6-fs pulse generation with a prism-pair-formed pulse shaper; L. Xu et al.; IEEE Journal Of Quantum Electronics; 36 (8): 893–899 (Aug. 2000); (1 page).

TNM–2 Negative Group Velocity Dispersion Mirrors; www.cvilaser.com/ultra-fast; CVI Laser Corporation; (Jan. 13, 2000); (2 pages).

Photogen–Technology; www.photogen.com/body/tech_body.html; Photogen Technologies, Inc., (Dec. 20, 2001); (19 pages).

International Search Report of PCT/US02/02548 dated Nov. 28, 2002, 4 pages.

Jerome Paye; "How to Measure the Amplitude and Phase of an Ultrashort Light Pulse with an Autocorrelator and a Spectrometer"; IEEE Journal of Quantum Electronics, vol. 30, No. 11, Nov. 1994; pp. 2693–2697.

Juan L.A. Chilla et al.; "Direct determination of the amplitude and the phase of femtosecond light pulses"; Jan. 1, 1991; vol. 16, No. 1; Optics Letters; pp. 39–41.

Daniel J. Kane et al.; "Single-shot measurement of the intensity and phase of an arbitrary ultrashort pulse by using frequency-resolved optical gating"; May 15, 1993, vol. 18, No. 10 Optics Letters; pp. 823–825.

Daniel J. Kane et al.; "Single-shot measurement of the intensity and phase of a femtosecond UV laser pulse with frequency-resolved optical gating"; Jul. 15, 1994, vol. 19, No. 14; Optic Letters; pp. 1061–1063.

D.S. Kim et al.; "Femtosecond pulse distortion in GaAs quantum wells and its effect on pump-probe or four-wave-mixing experiments"; Dec. 15, 1994; Physical Review B, vol. 50, No. 24, pp. 18 240–18 249.

Tracy Sharp Clement et al.; "Single-Shot measurement of the amplitude and phase of ultrashort laser pulses in the violet"; Jan. 1, 1995; Optics Letters, vol. 20, No. 1; pp. 70–72.

Bern Kohler et al.; "Phase and intensity characterization of femtosecond pulses from a chirped-pulse amplifier by frequency-resolved optical gating"; Mar. 1, 1995, vol. 20, No. 5, Optics Letters; pp. 483–485.

John N. Sweetser et al.; "Transient-grating frequency-resolved optical gating"; Apr. 15, 1997, vol. 22, No. 8; Optics Letters; pp. 519–521.

Rick Trebino et al.; "Measuring ultrashort laser pulses in the time–frequency domain using frequency-resolved optical gating"; Rev. Sci. Instrum. 68 (9), Sep. 1997; pp. 3277–3295.

John M. Dudley et al.; "Complete Characterization of Ultrashort Pulse Sources at 1550 nm"; IEEE Journal of Quantum Electronics, vol. 35, No. 4; Apr. 1999; pp. 441–450.

Rick Trebino et al.; "The Dilemma of Ultrashort-Laser-Pulse Intensity and Phase Measurement and Applications"; IEEE Journal of Quantum Electronics, vol. 35, No. 4, Apr. 1999; pp. 418–420.

Robert A. Kaindl et al.; "Generation, shaping, and characterization of intense femtosecond pulses tunable from 3 to 20 μm"; J. Opt. Soc. Am. B, vol. 17, No. 12, Dec. 2000; pp. 2086–2094.

I.G. Cormack et al.; "Practical measurement of femtosecond optical pulses using time-resolved optical gating"; Optics Communications 194 (Jul. 15, 2001); pp. 415–424.

Dmitriy Panasenko et al; "Single-shot sonogram generation for femtosecond laser pulse diagnostics by use to two-photon absorption in a silicon CCD camera"; Aug. 15, 2002, vol. 27, No. 16; Optics Letters; pp. 1475–1477.

Andrius Baltuska et al.; "Visible pulse compression to 4 fs by optical parametric amplification and programmable dispersion control"; Optics Letters, vol. 27, No. 5, Mar. 1, 2002; pp. 306–308.

Juan L.A. Chilla et al.; "Direct determination of the amplitude and the phase of femtosecond light pulses"; Jan. 1, 1991, vol. 16, No. 1; Optics Letters; pp. 39–41.

W.E. White et al.; "Direct measurement of the spectral phase of femtosecond pulses"; Apr. 15, 1995, vol. 20, No. 8; Optics Letters; pp. 904–906.

A. Sullivan et al.; "Quantitative investigation of optical phase-measuring techniques for ultrashort pulse lasers"; J. Opt. Soc. Am. B, vol. 13, No. 9, Sep. 1996; pp. 1965–1978.

Ellen M. Kosik et al.; "The effects of noise on ultrashort optical pulse measurement using SPIDER"; The Institute of Optics, University of Rochester, Rochester, NY; pp. 21–23.

T. Baumert et al.; "Femtosecond pulse shaping by an evolutionary algorithm with feedback"; Appl. Phys. B 65 (1997); pp. 779–782.

D. Meshulach et al.; "Adaptive ultrashort pulse compression and shaping"; Optics Communications 138 (1997); pp. 345–348.

Andrius Baltuska et al.; "Amplitude and phase characterization of 4.5-fs pulses by frequency-resolved optical gating"; Optics Letters, vol. 23, No. 18, Sep. 15, 1998; pp. 1474–1476.

L. Gallmann et al.; "Techniques for the characterization of sub-10-fs optical pulses: a comparison"; Appl. Phys. B 70 (Suppl), 2000; pp. S67–S75.

M.E. Anderson et al.; "The effects of noise on ultrashort-optical-pulse measurement using SPIDER"; Appl. Phys. B 70 (Suppl.); 2000; pp. S85–S93.

T. Brixner et al.; "Feedback-controlled femtosecond pulse shaping"; Appl. Phys. B 70 (Suppl.) 2000; pp. S119–S124.

G. Stobrawa et al.; "A new high-resolution femtosecond pulse shaper"; Appl. Phys. B 72 (2001); pp. 627–630.

M. Hacker et al.; "Frequency doubling of phase-modulated, ultrashort laser pulses"; Appl. Phys. B 73; (2001); pp. 273–277.

J.W. Nicholson et al.; "Noise sensitivity and accuracy of femtosecond pulse retrieval by phase and intensity from correlation and spectrum only (PICASO)"; J. Opt. Soc. Am. B; vol. 19, No. 2; Feb. 2002; pp. 330–339.

Christophe Dorrer et al.; "Precision and consistency criteria in spectral phase interferometry for direct electric–field reconstruciton"; J. Opt. Soc. Am. B, vol. 19, No. 5, May 2002; pp. 1030–1038.

Ian A. Walmsley et al.; "Characterization of the electric field of ultrashort optical pulses"; J. Opt. Soc. Am. B, vol. 13, No. 11; Nov. 1996; pp. 2453–2463.

K.C. Chu et al.; "Direct measurement of the spectral phase of femtosecond pulses"; Optics Letters, vol. 20, No. 8; Apr. 15, 1995; pp. 904–906.

H. Rudiger Lange et al.; "Reconstruction of the Time Profile of Femtosecond Laser Pulses Through Cross–Phase Modulation"; IEEE Journal of Selected Topics in Quantum Electronics, vol. 4, No. 2; Mar./Apr. 1998; pp. 295–300.

C. Iaconis et al.; "Direct Interferometric Techniques for Characteriziang Ultrashort Optical Pulses"; IEEE Journal of Selected Topics in Quantum Electronics, vol. 4, No. 2; Mar./Apr. 1998; pp. 285–294.

Andrew M. Weiner et al.; "Femtosecond Pulse Shaping for Synthesis, Processing and Time–to Space Conversion of Ultrafast Optical Waveforms"; IEEE Journal of Selected Topics in Quantum Electronics, vol. 4, No. 2; Mar./Apr. 1998; pp. 317–331.

C. Iaconis et al.; "Spectral phase interferometry for direct electric–field reconstruction of ultrashort optical pulses"; Optics Letters, vol. 23, No. 10, May 15, 1998; pp. 792–794.

P. Dietrich et al.; "Determining the absolute carrier phase of a few–cycle laser pulse"; Optics Letters, vol. 25, No. 1, Jan. 1, 2000; pp. 16–18.

D.T. Reid et al.; "Amplitude and phase measurement of mid–infrared femtosecond pulses by using cross–correlation frequency–resolved optical gating"; Optics Letters, vol. 25, No. 19, Oct. 1, 2000; pp. 1478–1480.

K. Michelmann et al.; "Measurement of the Page function of an ultrashort laser pulse"; Optics Communications, Oct. 15, 2001; pp. 163–170.

L. Gallmann et al.; "Spatially resolved amplitude and phase characterization of femtosecond optical pulses"; Optics Letters, vol. 26, No. 2, Jan. 15, 2001; pp. 96–98.

Masayuki Kakehata et al.; "Single–shot measurement of carrier–envelope phase changes by spectral interferometry"; Optics Letters, vol. 26, No. 18, Sep. 15, 2001; pp. 1436–1438.

J.P. Geindre et al.; "Single–shot spectral interferometry with chirped pulses"; Optics Letters, vol. 26, No. 20, Oct. 15, 2001; pp. 1612–1614.

C. Dorrer et al.; "Direct space–time characterization of the electric fields of ultrashort optical pulses"; Optics Letters, vol. 27, No. 7, Apr. 1, 2002; pp. 548–550.

Greg Taft et al.; "Measurement of 10–fs Laser Pulses"; IEEE Journal of Selected Topics in Quantum Electronics, vol. 2, No. 3, Sep. 1996; pp. 575–585.

Daniel J. Kane et al.; "Simultaneous measurement of two ultrashort laser pulses from a single spectrogram in a single shot"; Optical Society of America; vol. 14, No. 4, Apr. 1997; pp. 935–943.

Peter J. Delfyett et al.; "Joint Time–Frequency Meaurements of Mode–Locked Semiconductor Diode Lasers and Dynamics Using Frequency–Resolved Optical Gating"; IEEE Journal of Quantum Electronics, vol. 35, No. 4, Apr. 1999; pp. 487–500.

David N. Fittinghoff et al.; "Frequency–Resolved Optical Gating Measurement of Ultrashort Pulses Passing Through a High Numerical Aperture Objective"; IEEE Journal of Quantum Electronics, vol. 35, No. 4, Apr. 1999; pp. 479–486.

Andrius Baltuska et al.; "Second–Harmonic Generation Frequency–Resolved Optical Gating in the Single–Cycle Regime"; IEEE Journal of Quantum Electronics, vol. 35, No. 4, Apr. 1999; pp. 459–478.

Hilary K. Eaton et al.; "Investigating Nonlinear Femtosecond Pulse Propagation with Frequency–Resolved Optical Gating"; IEEE Journal of Quantum Electronics, vol. 35, No. 4, Apr. 1999; pp. 451–458.

Craig W. Siders et al.; "Multipulse Interferometric Frequency–Resolved Optical Gating"; IEEE Journal of Quantum Electronics, vol. 35, No. 4, Apr. 1999; pp. 432–440.

Derryck T. Reid; "Algorithm for Complete and Rapid Retrieval of Ultrashort Pulse Amplitude and Phase from a Sonogram"; IEEE Journal of Quantum Electronics; vol. 35, No. 11, Nov. 1999; pp. 1584–1598.

M.R. Fetterman et al.; "Propagation of Complex Laser Pulses in Optically Dense Media"; The American Physical Society, Physical Review Letters, vol. 82, No. 20, May 17, 1999; pp. 3984–3987.

Atsushi Yabushita et al.; "SHG FROG and XFROG methods for phase/intensity characterization of pulses propagated through an absorptive optical medium"; Optics Communications; Oct. 15, 2001; pp. 227–232.

Roer G.M.P. Koumans et al.; "Time–Resolved Optical Gating Based on Dispersive Propagation: A New Method to Characterize Optical Pulses"; IEEE Journal of Quantum Electronics, vol. 36, No. 2, Feb. 2000; pp. 137–144.

Daniel J. Kane et al.; "Convergence test for inversion of frequency–resolved optical gating spectrograms"; Optics Letters, vol. 25, No. 16, Aug. 15, 2000; pp. 1216–1218.

I.G. Cormack et al.; "Rapid measurement of ultrashort–pulse amplitude and phase from a two–photon absorption sonogram trace"; J. Opt. Soc. Am. B; vol. 18, No. 9, Sep. 2001; pp. 1377–1382.

Julie A. Greutzmacher et al.; "Time and frequency–gated FID: a new approach to study the vibrational dephasing of water"; pp. 530–532.

Juan L.A. Chilla et al.; "Analysis of a Method of Phase Measurement of Ultrashort Pulses in the Frequency Domain"; IEEE Journal of Quantum Electronics, vol. 27, No. 5, May 1991; pp. 1228–1235.

David N. Fittinghoff et al.; "Noise sensitivity in frequency–resolved optical–gating measurements of ultrashort pulses"; J. Opt. Soc. Am. B, vol. 12, No. 10, Oct. 1995; pp. 1955–1967.

Noriaki Tsurumachi et al.; "Interferometric observation of femtosecond free induction decay"; Optics Letters, vol. 19, No. 22, Nov. 15, 1994; pp. 1867–1869.

D. Yelin et al.; "Adaptive femtosecond pulse compression"; Optics Letters, vol. 22, No. 23, Dec. 1, 1997; pp. 1793–1795.

Gregory D. Goodno et al.; "Ultrafast heterodyne–detected transient–grating spectroscopy using diffractive optics"; Optical Society of America, vol. 15, No. 6, Jun. 1998; pp. 1791–1794.

A.V. Sokolov; "Subfemtosecond compression of periodic laser pulses"; Optics Letters, vol. 24, No. 17, Sep. 1, 1999; pp. 1248–1250.

H.S. Eisenberg et al.; "Phase Defects in Self–Focusing of Ultrashort Pulses"; Physical Review Letters, vol. 83, No. 3, Jul. 19, 1999; pp. 540–543.

C. Dorrer et al.; "Characterization of chirped–pulsed amplification systems with spectral phase interferometry for direct electric–field reconstruction"; Applied Physics B 70 (Suppl.), 2000; pp. S77–S84.

C. Radzewicz et al.; "A poor man's FROG"; Optics Communications, Dec. 15, 2000; pp. 329–333.

M. Hacker et al.; "Iterative Fourier transform algorithm for phase–only pulse shaping"; Optics Express, vol. 9, No. 4, Aug. 13, 2001; pp. 191–199.

L. Misoguti et al.; "Generation of Broadband VUV Light Using Third–Order Cascaded Processes"; Physical Review Letters, vol. 87, No. 1, Jul. 2, 2001; pp. 013601–1–013601–4.

Dong Gun Lee et al.; "Coherent Control of High–Order Harmonics with Chirped Femtosecond Laser Pulses"; Physical Review Letters, vol. 87, No. 24, Dec. 10, 2001; pp. 243902–1–243902–4.

D. Zeidler et al.; "Amplification of tailored white–light continuum"; Applied Physics, B74 (Suppl.), 2002; pp. S51–S56.

M. Armstrong et al.; "Versatile seven–femtosecond pulse compressor of parametrically amplified pulses using adaptive optics: studies of the primary events in protein dynamics"; Applied Physics B 74 (Suppl), 2002; pp. S127–S132.

T. Brixner et al.; "Generation and characterization of polarization–shaped femtosecond laser pulses"; Applied Physics B74 (Suppl); 2002; pp. S133–S144.

D.M. Villeneuve et al.; "Using frequency–domain manipulation of stretched femtosecond laser pulses to create fast rise and fall times on picosecond pulses"; Applied Physics B74 (Suppl.), 2002; pp. S157–S161.

C. Dorrer et al.; "Spatio–temporal characterization of the electric field of ultrashort optical pulses using two–dimensional shearing interferometry"; Applied Physics B74 (Suppl.), 2002; pp. S209–S217.

K.H. Hong et al.; "Time–frequency analysis of chirped femtosecond pulses using Wigner distribution function"; Applied Physics B74 (Suppl), 2002, pp. S231–S236.

Christophe Dorrer et al.; "Accuracy criterion for ultrashort pulse characterization techniques: application to spectral phase interferometry for direct electric field reconstruction"; Appl. Phys. B 74, vol. 19, No. 5, May 2002; pp. 1019–1029.

Dai–Sik Kim et al.; "Femtosecond–pulse distortion in quantum wells"; Appl. Phys B 74, vol. 48. No. 24; Dec. 15, 1993; pp. 17902–17905.

E. Tokunaga et al.; "Frequency–domain interferometer for femtosecond time–resolved phase spectroscopy"; Optics Letters, vol. 17, No. 16; Aug. 15, 1992; pp. 1131–1133.

Kazunori Naganuma et al; "General Method for Ultrashort Light Pulse Chirp Measurement"; IEEE Journal of Quantum Electronics, vol. 25, No. 5; Jun. 1989; pp. 1225–1233.

Victor Wong et al.; "Analysis of ultrashort pulse–shape measurement using linear interferometers"; Optics Letters, vol. 19, No. 4; Feb. 15, 1994; pp. 287–289.

D.S. Chemla et al; "Ultrafast phase dynamics of coherent emission from excitons in GaAs quantum wells"; Physical Review B, vol. 50, No. 12; Sep. 15, 1994; pp. 8439–8453.

Victor Wong et al.; "Linear filter analysis of methods for ultrashort–pulse–shape measurements"; J. Opt.Soc. Am. B, vol. 12, No. 8; Aug. 1995; pp. 1491–1499.

Y. Ding et al.; "Time–Domain Image Processing Using Dynamic Holography"; IEEE Journal of Selected Topics in Quantum Electronics, vol. 4, No. 2; Mar./Apr. 1998; pp. 332–341.

Jerome Tignon et al.; "Spectral Interferometry of Semiconductor Nanostructures"; IEEE Journal of Quantum Electronics, vol. 35, No. 4; Apr. 1999; pp. 510–522.

Arthur L. Smirl et al.; "Heavy–Hole and Light–Hole Quantum Beats in the Polarization State of Coherent Emission from Quantum Wells"; IEEE Journal of Quantum Electronics, vol. 35, No. 4; Apr. 1999; pp. 523–531.

Chris Iaconis et al; "Self–Referencing Spectral Interferometry for Measuring Ultrashort Optical Pulses"; IEEE Journal of Quantum Electronics, vol. 35, No. 4; Apr. 1999; pp. 501–509.

Jung–Ho Chung et al.; "Ambiguity of Ultrashort Pulse Shapes Retrieved From the Intensity Autocorrelation and the Power Spectrum"; IEEE Journal on Selected Topics of Quantum Electronics, vol. 7, No. 4; Jul./Aug. 2001; pp. 656–666.

John D. Hybl et al; "Two–dimensional Fourier transform electronic spectroscopy"; Journal of Chemical Physics, vol. 115, No. 14; Oct. 8, 2001; pp. 6606–6622.

Anthony P. Peirce et al.; "Optimal control of quantum–mechanical systems; Existence, numerical approximation and applications"; Physical Review A, vol. 37, No. 12; Jun. 15, 1988; pp. 4950–4964.

Richard S. Judson et al.; "Teaching Lasers to Control Molecules"; Physical Review Letters, vol. 68, No. 10; Mar. 9, 1992; pp. 1500–1503.

Michael Messina et al.; "Quantum control of multidimensional systems; Implementation within the time–dependent Hartree approximation"; J. Chem Phys. 104; Jan. 1996; pp. 173–182.

D.H. Schirrmeister et al; "Femtosecond pulse dependence of dissipation in molecular systems"; Chemical Physic Letters Dec. 4, 1998; pp. 383–390.

Herschel Rabitz et al.; "Optimal Control of Molecular Motion: Design, Implementation and Inversion"; Acc. Chem. Res., vol. 33, No. 8; 2000; pp. 572–578.

R. deVivie–Riedle et al.; "Design and interpretation of laser pulses for the control of quantum systems"; Applied Physics B; 2000; pp. 285–292.

J.M. Geremia et al.; "Incorporating physical implmentation concerns into closed loop quantum control experiments"; Journal of Chemical Physics, vol. 113, No. 24; Dec. 22, 2000; pp. 10841–10848.

Thomas Hornung et al.; "Adapting optimal control theory and using learning loops to provide experimentally feasible shaping mask patterns"; Journal of Chemical Physics, vol. 115, No. 7; Aug. 15, 2001; pp. 3105–3111.

Moshe Shapiro et al.; "On the Origin of Pulse Shaping Control of Molecular Dynamics"; J: Phys. Chem. A, vol. 105, No. 105; 2001; pp. 2897–2902.

S. Abbas Hosseini et al.; "Coherent control of multiphoton transitions with femtosecond pulse shaping"; Physical Review A, pp. 033410–1–033410–7.

Thomas Hornung et al.; "Teaching optimal control theory to distill robust pulses even under experimental constraints"; Physical Review A, vol. 65; 2002; pp. 021403–1–021403–4.

Yi Jing Yan et al.; "Electronic dephasing, vibrational relaxation, and solvent friction in molecular nonlinear optical line shapes"; J. Chems. Phys., Oct. 15, 1988; pp. 5160–5176.

Y.J. Yan et al.; "Pulse shaping and coherent Raman spectroscopy in condensed phases"; J. Chem. Phys 94 (2); Jan. 15, 1991; pp. 997–1001.

Bern Kohler et al.; "Mode–Locking Matter with Light"; J. Phys. Chem 1993, 97; pp. 12602–12608.

Jeffrey L. Krause et al.; "Optical control of molecular dynamics: Molecular cannons, reflectrons and wave–packet focusers"; J. Chem. Phys. 99(9); Nov. 1, 1993; pp. 6562–6578.

V. Engel et al.; "Two–photon wave–packet interferometry"; J. Chem Phys. 100 (8); Apr. 15, 1994; pp. 5448–5458.

David M. Jonas et al.; "Femtosecond Wavepacket Spectroscopy: Influence of Temperature, Wavelength and Pulse Duration"; J. Phys. Chem.; 1995; pp. 2594–2608.

Jeffrey L. Krause et al.; "Quantum Control of Molecular Dynamics: The Strong Response Regime"; J. Phys. Chem; 1995, 99; pp. 13736–13747.

Jianwei Che et al.; "Detection and Control of Molecular Quantum Dynamics"; J. Phys. Chem.; 1995; pp. 14949–14958.

M. Sterling et al.; "Interrogation and control of condensed phase chemical dynamics with linearly chirped pulses:$I_2$ in solid Kr"; J. Chem. Phys. 104; May 1, 1996; pp. 6497–6506.

Jianwei Che et al.; "Semiclassical Dynamics and Quantum Control in Condensed Phases: Application to $I_2$ in a Solid Argon Matrix"; J. Phys. Chem. 1996, 100; pp. 7873–7883.

Jianshu Cao et al.; "A simple physical picture for quantum control of wave packet localization"; J. Chem Phys., 197; Aug. 1, 1997; pp. 1441–1450.

Jianshu Cao et al.; "Intrapulse Dynamical Effects in Multiphoton Processes: Theoretical Analysis"; J. Phys. Chem. A; vol. 102, 1998; pp. 4284–4290.

Kenji Mishima et al.; "A theoretical study on laser control of a molecular nonadiabatic process by ultrashort chirped laser pulses"; Journal of Chemical Physics, vol. 109., No. 5; Aug. 1, 1998; pp. 1801–1809.

Amichay Vardi et al.; "Laser catalysis with pulses"; Physical Review A, vol. 58, No. 2; Aug. 1998; pp. 1352–1360.

H.A. Kim et al.; "Expanded concept of the adiabatic population transfer using dressed states"; Physical Review A, vol. 59, No. 2; Feb. 1999; pp. 1404–1407.

Jianshu Cao et al.; "Molecular pie pulses: Population inversion with positively chirped short pulses"; Journal of Chemical Physics, vol. 113, No. 5; Aug. 1, 2000; pp. 1898–1909.

A.J. Wurzer et al.; "Highly localized vibronic wavepackets in large reactive molecules"; Appl. Phys. B 71, 2000; pp. 405–409.

F. Legare et al.; "Laser pulse control of Raman processes by chirped non–adiabatic passage"; Journal of Raman Spectroscopy; 2000; pp. 15–23.

Moshe Shapiro et al.; "Coherently Controlled Asymmetric Synthesis with Achiral Light"; Physical Review Letters, vol. 84, No. 8; Feb. 21, 2000; pp. 1669–1672.

Gabriel Turinici et al.; "Quantum wavefunction controllability"; Chemical Physics 267; 2001; pp. 1–9.

M. Gruebele; "Fully quantum coherent control"; Chemical Physics 267; 2001; pp. 33–46.

V.S. Malinovsky et al.; "General theory of population transfer by adiabatic rapid passage with intense, chirped laser pulses"; The European Physical Journal D 14; 2001; pp. 147–155.

Z.W. Shen et al.; "Selective preparation of ground state wave–packets: a theoretical analysis of femtosecond pump–dump–probe experiments on the potassium dimer"; The European Physical Journal D 14; 2001; pp. 167–172.

Sanislav S. Bychkov et al.; "Laser coherent control of molecular chiral states via entanglement of the rotational and torsional degrees of freedom"; Journal of Raman Spectroscopy; 2002; pp. 962–973.

S.E. Harris; "Control of Feshbach resonances by quantum interference"; Physical Review A66; 2002; pp. 010701-1–010701-4.

John M. Jean et al.; "Application of a multilevel Redfiled theory .to electron transfer in condensed phases"; J. Chem. Phys. 96; Apr. 15, 1992; pp. 5827–5842.

Bjarne Amstrup et al.; "Control of HOD photodissociation dynamics via bond–selective infrared multiphoton excitation and a femtosecond ultraviolet laser pulse"; J. Chem. Phys., vol. 97, No. 11; Dec. 1, 1992; pp. 8285–8295.

L.D. Ziegler et al.; "Nonlinear polarization description of phase–locked pulse–pair spectroscopy"; J. Chem. Phys., vol. 97, No. 7; Oct. 1, 1992; pp. 4704–4713.

D. Lalovic et al.; "Quantum mechanics in terms of non–negative smoothed Wigner functions"; Physical Review A, vol. 46, No. 3; Aug. 1, 1992; pp. 1206–1212.

S. Meyer et al.; "Photoelectron distributions from femtosecond pump/probe excitation with chirped probe pulses"; Journal of Chemical Physics, vol. 108, No. 18; pp. 7631–7636.

V.M. Akulin et al.; "Laser Control of Atomic Motion inside Diatomic Molecules"; J. Phys. Chem. A, vol. 102, No. 23; 1998; pp. 4310–4320.

Jeffrey L. Krause et al.; "Creating and Detecting Shaped Rydberg Wave Packets"; Physical Review Letters, vol. 79, No. 25; Dec. 22, 1997; pp. 4978–4981.

Jianshu Cao et al.; "Molecular Pi PUlse to Total Inversion of Electronic State Population"; Physical Review Letters, vol. 80, No. 7; Feb. 16, 1998; pp. 1406–1409.

Christopher J. Bardeen et al.; "Using time–dependent rate equations to describe chirped pulse excitation in condensed phases"; Chemical Physics Letters 302; 1999; pp. 405–410.

Moshe Shapiro et al.; "Nonadiabatic wave packet dynamics: Experiment and theory in IBr"; Journal of Chemical Physics, vol. 110, No. 5; Feb. 1, 1999; pp. 2465–2473.

Zhenwen Shen et al.; "Pump–dump control and the related transient absorption spectroscopies"; Journal of Chemical Physics, vol. 110, No. 15; Apr. 15, 1999; pp. 7192–7201.

Kenji Mishima et al.; "Theoretical study on quantum control of photodissociation and photodesorption dynamics by femtosecond chirped laser pulses"; Journal of Chemical Physics, vol. 110, No. 16; Apr. 22, 1999; pp. 7756–7769.

Yu–Chen Shen et al.; "What can short–pulse pump–probe spectroscopy tell us about Franck–Condon dynamics?"; Journal of Chemical Physics, vol. 110, No. 20; May 22, 1999; pp. 9793–9806.

H.S. Moon et al.; "Coherence control using the ratio of Rabi frequencies for complete coherent inversion in a four–level system"; J. Phys B At. Mol. Phys. vol. 32; 1999; pp. 987–999.

Jeffrey A. Cina; "Nonlinear wavepacket interferometry for polyatomic molecules"; Journal of Chemical Physics, vol. 113, No. 21; Dec. 1, 2000; pp. 9488–9496.

M. Ovchinnikov et al.; "Semiclassical molecular dynamics computation of spontaneous light emission in the condensed phase: Resonance Raman spectra"; Journal of Chemical Physics, vol. 114, No. 16; Apr. 22, 2001; pp. 7130–7143.

F. Gelmukhanov et al.; "Dynamics of two–photon absorption by molecules and solutions"; J. Opt. Soc. Am. B, vol. 19, No. 5; May 2002; pp. 937–945.

V. Kabelka et al.; "Time–frequency imaging of a single ultrashort light pulse from anularly resolved autocorrelation"; Optics Letters, vol. 20, No. 1; Jun. 1, 1995; pp. 1301–1303.

Paul R. Bolton et al.; "Propagation of intense, ultrashort laser pulses through metal vapor: refraction–limited behavior for single pulses"; J. Opt. Soc. Am. B, vol. 13, No. 2; Feb. 1996; pp. 336–346.

June–Koo Rhee et al.; "Real–time dispersion analyzer of femtosecond laser pulses with use of a spectrally and temporally resolved upconversion technique"; J. Opt. Soc. Am. B, vol. 13, No. 8; Aug. 1996; pp. 1780–1785.

Marco A. Krumbugel et al.; "Direct ultrashort–pulse intensity and phase retrieval by frequency–resolved optical gating and a computational neural network"; Optics Letters, vol. 21, No. 2; Jan. 15, 1996; pp. 143–145.

S. Backus et al.; "16–fs, 1–µJ ultraviolet pulses generated by third–harmonic conversion in air"; Optics Letters, vol. 21, No. 9; May 1, 1996; pp. 665–667.

C. Iaconis et al.; "Direct measurment of the two–point field correlation function"; Optics Letters, vol. 21, No. 21; Nov. 1, 1996; pp. 1783–1785.

David N. Fittinghoff et al.; "Measurement of the intensity and phase of ultraweak, ultrashort laser pulses"; Optics Letters, vol. 21, No. 12; Jun. 15, 1996; pp. 884–886.

T. Feurer et al.; "Measuring the temporal intensity of ultrashort laser pulses by triple correlation"; Appl. Phys. B; 1998; pp. 163–168.

Alfred Kwok et al.; "Frequency–Resolved Optical Gating Using Cascaded Second–Order Nonlinearities"; Journal of Selected Topics in Quantum Electronics, vol. 4, No. 2; Mar./Apr. 1998; pp. 271–277.

Daniel J. Kane; "Real–Time Measurement of Ultrashort Laser Pulse Using Principal Component Generalized Projection"; IEEE Journal of Selected Topics in Quantum Elecronics; vol. 4, No. 2; Mar./Apr. 1998; pp. 278–284.

Scott A. Diddams et al.; "Characterizing the Nonlinear Propagation of Femtosecond Pulses in Bulk Media"; IEEE Journal of Selected Topics in Quantum Electronics, vol. 4, No. 2; Mar./Apr. 1998; pp. 306–316.

Kazuya Takasago et al.; "Evaluation of Femtosecond Pulse Shaping with Low–Loss Phase–Only Masks"; IEEE Journal of Selected Topics in Quantum Electronics, vol. 4, No. 2; Mar./Apr. 1998; pp. 346–352.

J. Peatross et al.; "Temporal decorrelation of short laser pulses"; J. Opt. Soc. Am. B, vol. 15, No. 1; Jan. 1998; pp. 216–222.

Michael J. Stimson et al.; "Noisy–light correlation functions by frequency resolved optical gating"; J. Opt. Soc. Am. B, vol. 15, No. 2; Feb. 1998; pp. 505–514.

J. W. Nicholson et al.; "Full–field characterization of femtosecond pulses by spectrum and cross–correlation measurements"; Optics Letters, vol. 24, No. 23; Dec. 1, 1999; pp. 1774–1776.

F. Romstad et al.; "Measurement of Pulse Amplitude and Phase Distortion in a Semiconductor Optical Amplifier: from Pulse Compression to Breakup"; IEEE Photonics Technology Letters, vol. 12, No. 12; Dec. 2000; pp. 1674–1676.

Tzu–Ming Liu et al.; "Triple–optical autocorrelation for direct optical pulse–shape meausrement"; Applied Physics Letters, vol. 81, No. 8; Aug. 19, 2002; pp. 1402–1404.

Julie A. Gruetzmacher et al.; "Few–cycle mid–infrared pulse generation, characterization and coherent propagation in optically dense media"; Review of Scientific Instruments, vol. 73, No. 6; Jun. 2002; pp. 2227–2236.

A.M. Weiner et al.; "Femtosecond Pulse Sequences Used for Optical Manipulation of Molecular Motion"; Reports; Mar. 16, 1990; pp. 1317–1319.

Yoshihiro Takagi et al.; "Multiple– and single–shot autocorrelator based on two–photon conductivity in semiconductors"; Optics Letters, vol. 17, No. 9; May 1, 1992; pp. 658–660.

Thomas J. Dunn et al.; "Experimental Determination of the Dynamics of a Molecular Nuclear Wave Packet via the Spectra of Spontaneous Emission"; Physical Review Letters, vol. 70, No. 22; May 31, 1993; pp. 3388–3391.

M.E. Fermann et al.; "Shaping of ultrashort optical pulses by using an integrated acousto–optic tunable filter"; Optics Letters, vol. 18, No. 18; Sep. 15, 1993; pp. 1505–1507.

V.L. da Silva et al.; "Nonlinear pulse shaping and causality"; Optics Letters, vol. 18, No. 8; Apr. 15, 1993; pp. 580–582.

T. Brixner et al.; "Feedback–controlled optimization of amplified femtosecond laser pulses"; Applied Physics B 68; 1999; pp. 281–284.

S. Yeremenko et al.; "The criterion of pulse reconstruction quality based on Wigner representation"; Applied Physics B 70 (Suppl.); 2000; pp. S109–S117.

A. Efimov et al.; "Minimization of dispersion in an ultrafast chirped pulse amplifier using adaptive learning"; Appl. Phys. B 70 (Suppl.); 2000; pp. S133–S141.

T. Kobayashi et al.; "Tunable visible and near–infrared pulse generator in a 5 fs regime"; Appl. Phys. B 70 (Suppl.); 2000; pp. S239–S246.

R. deVivie–Riedle et al.; "Design and interpretation of laser pulses for the control of quantum systems"; Appl. Phys. B 71; 2000; pp. 285–292.

Ch. Warmuth et al.; "Studying vibrational wavepacket dynamics by measuring fluorescence interference fluctuations"; Journal of Chemical Physics, vol. 112, No. 11; Mar. 15, 2000; pp. 5060–5069.

E. Zeek et al.; "Adaptive pulse compression for transform–limited 15–fs high–energy pulse generation"; Optics Letters, vol. 25, No. 8; Apr. 15, 2000; pp. 587–589.

A. Apolonski et al.; "Controlling the Phase Evolution of Few–Cycle Light Pulses"; Physical Review Letters, vol. 85, No. 4; Jul. 24, 2000; pp. 740–743.

Ch. Warmuth et al.; "Molecular quantum dynamics in a thermal system: Fractional wave packet revivals probed by random–phase fluorescence interferometry"; Journal of Chemical Physics, vol. 114, No. 22; Jun. 8, 2001; pp. 9901–9910.

A.N. Naumov et al.; "Frequency–time and time–space mappings for single–shot coherent four–wave mixing with chirped pulses and broad beams"; Journal of Raman Spectroscopy, 2001; pp. 960–970.

G.G. Paulus et al.; "Absolute–phase phenomena in photo-ionization with few–cycle laser pulses"; Nature, vol. 414; Nov. 8, 2001; pp. 182–184.

Yaron Silberberg; "Physics at the attosecond frontier"; Nature, vol. 414, Nov. 29, 2001; pp. 494–495.

M. Hentschel et al.; "Attosecond metrology"; Nature, vol. 414; Nov. 29, 2001; pp. 509–513.

K. Michelmann et al.; "Measurement of the Page function of an ultrashort laser pulse"; Optics Communications; Oct. 15, 2001; pp. 163–170.

L. Lepetit et al.; "Linear techniques of phase measurement by femtosecond spectral interferometry for applications in spectroscopy"; J. Opt. Soc. Am. B, vol. 12, No. 12; Dec. 1995; pp. 2467–2474.

E.T.J. Nibbering et al.; "Spectral determination of the amplitude and the phase of intense ultrashort optical pulses"; J. Opt. Soc. Am. B, vol. 13, No. 2; Feb. 1996; pp. 317–329.

L. Lepetit et al.; "Two–dimensional nonlinear optics using Fourier–transform spectral interferometry"; Optics Letters, vol. 21, No. 8; Apr. 15, 1996; pp. 564–566.

K.C. Chu et al.; "Temporal interferometric measurement of femtosecond spectral phase"; Optics Letters, vol. 21, No. 22; Nov. 15, 1996; pp. 1842–1844.

Victor Wong et al.; "Ultrashort–pulse characterization from dynamic spectrograms by iterative phase retrieval"; J. Opt. Soc. Am. B, vol. 14, No. 4; Apr. 1997; pp. 944–949.

W.J. Walecki et al.; "Characterization of the polarization state of weak ultrashort coherent signals by dual–channel spectral interferometry"; Optics Letters, vol. 22, No. 2; Jan. 15, 1997; pp. 81–83.

J.P. Likforman et al.; "Measurement of photon echoes by use of femtosecond Fourier–transform" Spectral Interferometry; Optics Letters, vol. 22, No. 14; Jul. 15, 1997; pp. 1104–1106.

Michel F. Emde et al.; "Spectral interferometry as an alternative to time–domain heterodyning"; Optics Letters, vol. 22, No. 17; Sep. 1, 1997; pp. 1338–1340.

X. Chen et al.; "Temporally and spectrally resolved amplitude and phase of coherent four–wave–mixing emission from GaAs quantum wells"; Physical Review B, vol. 56, No. 15; Oct. 15, 1997; pp. 9738–9743.

Christophe Dorrer et al.; "Phase Amplitude Coupling in Spectral Phase Modulation"; IEEE Journal of Selected Topics in Quantum Electronics, vol. 4, No. 2; Mar./Apr. 1998; pp. 342–345.

Sarah M. Gallagher et al.; "Heterodyne detection of the complete electric field of femtosecond four–wave mixing signals"; J. Opt. Soc. Am. B, vol. 15, No. 8; Aug. 1998; pp. 2338–2345.

Christophe Dorrer; "Influence of the calibration of the detector on spectral interferometry"; J. Opt. Soc. Am. B; vol. 16, No. 7; Jul. 1999; pp. 1160–1168.

Allison W. Albrecht et al.; "Experimental distinction between phase shifts and time delays: Implications for femtosecond spectroscopy and coherent control of chemical reactions"; Journal of Chemical Physics, vol. 111, No. 24; Dec. 22, 1999; pp. 10934–10955.

C. Dorrer et al.; "Single–shot real–time characterization of chirped–pulse amplification systems by spectral phase interferometry for direct electric–field reconstruction"; Optics Letters, vol. 24, No. 22; Nov. 15, 1999; pp. 1644–1646.

C. Dorrer; "Implementation of spectral phase interferometry for direct electric–field reconstruction with a simultaneously recorded reference interferogram"; Optics Letters, vol. 24, No. 21; Nov. 1, 1999; pp. 1532–1534.

Christophe Dorrer et al.; "Spectral resolution and sampling issues in Fourier–transform spectral interferometry"; J. Opt. Soc. Am. B, vol. 17, No. 10; Oct. 2000; pp. 1795–1802.

C.Y. Chien et al.; "Single–shot chirped–pulse spectral interferometry used to measure the femtosecond ionization dynamics of air"; Optics Letters, vol. 25, No. 8; Apr. 15, 2000; pp. 578–580.

J.W. Nicholson et al.; "Unbalanced third–order correlations for full characterization of femtosecond pulses"; Optics Letters, vol. 25, No. 24; Dec. 15, 2000; pp. 1801–1803.

A. Apolonski et al.; "Controlling the Phase Evolution of Few–Cycle Light Pulses"; Physical Review Letters, Vo. 85, No. 4; Jul. 24, 2000; pp. 740–743.

David J. Jones et al.; "Carrier–Envelope Phase Control of Femtosecond Mode–Locked Lasers and Direct Optical Frequency Synthesis"; Science magazine, vol. 288; Apr. 28, 2000; pp. 635–639.

A. Poppe et al; "Few–cycle optical waveform synthesis"; Applied Physics B 72; 2001; pp. 373–376.

Allison Albrecht Ferro et al.; "Complete femtosecond linear free induction decay, Fourier algorithm for dispersion relations and accuracy of the rotating wave approximation"; Journal of Chemical Physics, vol. 114, No. 10; Mar. 8, 2001; pp. 4649–4656.

Chantal Daniel et al.; "Deciphering the Reaction Dynamics Underlying Optimal Control Laser Fields"; Science Magazine, vol. 299; Jan. 24, 2003; pp. 536–539.

T. Witte et al.; "Controlling molecular ground–state dissociation by optimizing vibrational ladder climbing"; Journal of Chemical Physics, vol. 118, No. 5; Feb. 1, 2003; pp. 2021–2024.

R.J. Levis et al.; "Closing the Loop on Bond Selective Chemistry Using Tailored Strong Field Laser Pulses"; The Journal of Physical Chemistry, vol. 106, No. 27; Jul. 11, 2002; pp. 6427–6444.

Mustafa Demirplak et al.; "Optical control of molecular dynamics in a liquid"; Journal of Chemical Physics, vol. 116, No. 18; May 8, 2002; pp. 8028–8035.

M. Bergt et al.; "Time–resolved organometallic photochemistry Femtosecond fragmentation and adaptive control of $CpFe(CO)_2X$ (X=C1,Br,1)"; Journal of Organometallic Chemistry 661; 2002; pp. 199–209.

Ben R. Torralva et al; "Mechanisms for laser control of chemical reactions"; Journal of Modern Optics, vol. 49, No. 3/4; 2002; pp. 593–625.

N.H. Damrauer et al.; "Control of bond–selective photochemistry in $CH_2BrCl$ using adaptive femtosecond pulse shaping"; The European Physical Journal D, 20, 2002; pp. 71–76.

L. Windhorn et al.; "Molecular dissociation by mid–tR femtosecond pulses"; Chemical Physics Letters 357, May 3, 2002; pp. 85–90.

Robert J. Levis et al.; "Selective Bond Dissociation and Rearrangement with Optimally Tailored, Strong–Field Laser Pulses"; Science Magazine, vol. 292; Apr. 27, 2001; pp. 709–713.

T. Brixner et al.; "Problem complexity in femtosecond quantum control"; Chemical Physics 267; 2001; pp. 241–246.

O.M. Sarkisov et al.; "Control of elementary chemical reactions by femtosecond light pulses"; Quantum Electronics, vol. 31, No. 6; 2001; pp. 483–488.

Julie A. Mueller et al.; "Competing isomeric product channels in the 193 nm photodissociation of 2–chloropropene and in the unimolecular dissociation of the 2–propenyl radical"; Journal of Chemical Physics, vol. 114, No. 10; Mar. 8, 2001; pp. 4505–4521.

Chantal Daniel et al.; "Analysis and control of laser induced fragmentation processes in $CpMn(CO)_3$"; Chemical Physics 267; 2001; pp. 247–260.

A. Glass et al.; "Control of the photodissociation of CsCl"; Applied Physics B 71; 2000; pp. 267–276.

T. Frohnmeyer et al.; "Femtosecond pump–probe photoelectron spectroscopy on Na2: a tool to study basic coherent control schemes"; Applied Physics B 71; 2000; pp. 259–266.

M. Bergt et al.; "Controlling the Femtochemistry of $Fe(CO)_5$"; J. Phys. Chem. A, vol. 103, No. 49; 1999; pp. 10381–10387.

A. Assion et al.; "Control of Chemical Reactions by Feedback–Optimized Phase–shaped Femtosecond Laser Pulses"; Science Magazine, vol. 282; Oct. 30, 1998; pp. 919–922.

A. Assion et al.; "Coherent control by a single phase shaped femtosecond laser pulse"; Chemical Physics Letters 259; Sep. 13, 1996; pp. 488–494.

Langchi Zhu et al.; "Coherent Laser Control of the Product Distribution Obtained in the Photoexcitation of HI"; Science Magazine, vol. 270; Oct. 6, 1995; pp. 77–80.

Yu–húi Chiu et al.; "Vibrational mode effects, scattering dynamics and energy disposal in reaction of $C_2H_2$ with methane"; J. Chem. Phys., vol. 102, No. 3; Jan. 15, 1995; pp. 1199–1216.

J.S. Keller et al.; "Selective bond fission in methyl mercaptan at 193 nm via radial derivative coupling between. the $2^1A''$ and $1^1A''$ adiabatic electronic states"; J. Chem. Phys. vol. 96, No. 6; Mar. 15, 1992; pp. 4324–4329.

I. Bar et al.; "Mode–selective bond fission: Comparison between the photodissociation of HOD (0,0,1) and HOD (1,0,0)"; J. Chem. Phys. vol. 95, No. 5; Sep. 1, 1991; pp. 3341–3346.

Michael J. Bronikowski et al.; "Bond–specific chemistry: OD:OH product ratios for the reactions H+HOD(100) and H+HOD(001)"; J. Chem. Phys., vol. 95, No. 11; Dec. 1, 1991; pp. 8647–8648.

I. Bar et al.; "Direct observation of preferential bond fission by excitation of a vibrational fundamental: Photodissociation of HOD (0,0,1)"; J. Chem. Phys., vol. 93, No. 3; Aug. 1, 1990; pp. 2146–2148.

R.L. VanderWal et al.; "Selectively breaking the O–H bond in HOD"; J. Chem. Phys., vol. 92, No. 1; Jan. 1, 1990; pp. 803–805.

Neil Shafer et al.; "Isotope effect in the photodissociation of HDO at 157.5 nm"; J. Chem. Phys., vol. 90, No. 11; Jun. 1, 1989; pp. 6807–6808.

L.J. Butler et al.; "The electronic state–selective photodissociation of CH2BrI at 248, 210 and 193 nm"; J. Chem. Phys. vol. 86, No. 4; Feb. 15, 1997; pp. 2051–2074.

L.J. Butler et al.; "Bond selective photochemistry in CH2BrI through electronic excitation at 210 nm"; J. Chem. Phys., vol. 84, No. 7; Apr. 1 1986; pp. 4104–4106.

David J. Tannor et al.; "Control of selectivity of chemical reaction via control of wave packet evolution"; J. Chem. Phys., vol. 83, No. 10; Nov. 15, 1985; pp. 5013–5018.

Lutfur R. Khundkar et al.; "Ultrafast Molecular Reaction Dynamics in Real–Time: Progress Over a Decade"; Annu. Rev. Phys. Chem., 1990; pp. 15–60.

Stuart A. Rice; "Optical control of reactions"; Nature Magazine, vol. 403; Feb. 3, 2000; pp. 496–497.

Richard N. Zare; "Laser Control of Chemical Reactions"; Science magazine, vol. 279; Mar. 20, 1998; pp. 1875–1879.

Stuart A. Rice; "Active Control of Molecular Dynamics: Coherence versus Chaos"; Journal of Statistical Physics, vol. 101, Nos. 1/2; 2000; pp. 187–212.

Herschel Rabitz et al.; "Whither the Future of Controlling Quantum Phenomena?"; Science magazine, vol. 288; May 5, 2000; pp. 824–828.

Yuri T. Mazurenko; "Spectral Holography and Spectral Nonlinear Optics of Ultrashort Pulses"; Journal of the Chinese Chemical Society, vol. 47, No. 4A; 2000; pp. 679–582.

Marcos Dantus; "Coherent Nonlinear Spectroscopy: From Femtosecond Dynamics to Control"; Annu. Rev. Phys. Chem. 2001; pp. 639–679, C1–C7.

Stuart A. Rice; "Interfering for the good of a chemical reaction"; Nature magazine; vol. 409; Jan. 18, 2001; pp. 422–426.

Wolfgang Kiefer et al.; "Femtosecond time–resolved spectroscopy of elementary molecular dynamics"; Naturwissenschaften; 2000; pp. 250–258.

Alois Renn et al.; "Multidimensional Holography by Persistent Spectral Hole Burning"; The Journal of Physical Chemistry A, vol. 106, No. 13; Apr. 4, 2002; pp. 3045–3060.

T. C. Weinacht et al.; "Using feedback for coherent control of quantum systems"; Journal of Optics B: Quantum and Semiclassical Optics; 2002; pp. R35–R52.

Niels E. Henriksen; "Laser control of chemical reactions"; 2002; pp. 37–42. Chem. Soc. Rev. 3137 42.

Stuart A. Rice et al.; "Active control of product selection in a chemical reaction: a view of the current scene"; Phys. Chem. Chem. Phys.; 2002; pp. 1683–1700.

Allen J. Bard et al.; "Holy Grails in Chemistry"; American Chemical Society, vol. 28, No. 3; Mar. 1995.

Marcos Dantus; "Ultrafast Probing and Control of Molecular Dynamics: Beyond the Pump–Probe Method"; pp. 169–188. Kuhn & Weyh SRZ Sep. 4, 2001.

Phillip H. Bucksbaum; "Ultrafast control"; Nature magazine, vol. 421; Feb. 6, 2003; pp. 593–594. Kuhn & Weyn SR2 Sep. 4, 2001.

Christopher J. Bardeen et al.; "Effect of Pulse Shape on the Efficiency of Multiphoton Processes: Implications for Biological Microscopy"; Journal of Biomedical Optics, vol. 4, No. 3; Jul. 1999; pp. 362–367.

Doron Meshulach et al.; "Coherent quantum control of multiphoton transitions by shaped ultrashort optical pulses"; Physical Review A, vol. 60, No. 2; Aug. 1999; pp. 1287–1292.

T. Hornung et al.; "Optimal control of one– and two–photon transitions with shaped femtosecond pulses and feedback"; Applied Physics B 71; 2000; pp. 277–284.

T. Brixner et al.; "Photoselective adaptive femtosecond quantum control in the liquid phase"; Nature magazine, vol. 414; Nov. 2001; pp. 57–60.

B.J. Pearson et al.; "Coherent control using adaptive learning algorithms"; Physical Review A, vol. 63; 2001; pp. 063412–1–063412–12.

D. Zeidler et al.; "Evolutionary algorithms and their application to optimal control studies"; Physical Review A, vol. 64; 2001; pp. 023420–1–023420–13.

Jennifer L. Herek et al.; "Quantum control of energy flow in light harvesting"; Nature magazine, vol. 417; May 30, 2002; pp. 533–535.

Nirit Dudovich et al.; "Single–pulse coherently controlled nonlinear Raman spectroscopy and microscopy"; Nature magazine, vol. 418; Aug. 1, 2002; pp. 512–514.

Dan Oron et al.; "Single–Pulse Phase–Contrast Nonlinear Raman Spectroscopy"; Physical Review Letters, vol. 89, No. 27; Dec. 30, 2002; pp. 27300-1–273001-4.

T. Brixner et al.; "Liquid–phase adaptive femtosecond quantum control: Removing intrinsic intensity dependencies"; Journal of Chemical Physics, vol. 118, No. 8; Feb. 22, 2003; pp. 3692–3701.

R. Netz et al., "Observation of Selectivity of Coherent Population Transfer Induced by Optical Interference"; Physical Review Letters, vol. 90, No. 6; Feb. 14, 2003; pp. 063001-1–063001-4.

Bern Kohler et al.; "Controlling the Future of Matter"; Acc. Chem. Res., vol. 28, No. 3; 1995; pp. 133–140.

D.W. Schumacher et al.; Physical Review A, vol. 54, No. 5; Nov. 1996; pp. 4271–4278. "Phase Dependence of Intense Field Ionization".

Christopher J. Bardeen et al.; "Feedback quantum control of molecular electronic population transfer"; Chemical Physics Letters 280; 1997; pp. 151–158.

Christopher J. Bardeen et al.; "Quantum Control of NaI Photodissociation Reaction Product States by Ultrafast Tailored Light Pulses"; J. Phys. Chem. A, vol. 101, No. 20; pp. 3815–3822. 1997.

Christopher J. Bardeen et al.; "Quantum Control of Population Transfer in Green Fluorescent Protein by Using Chirped Femtosecond Pulses"; J. Am. Chem. Soc., vol. 120, No. 50; 1998; 13023–13027.

Doron Meshulach et al.; "Coherent quantum control of two–photon transitions by a femtosecond laser pulse"; Nature magazine, vol. 396; Nov. 19, 1998; pp. 239–242.

Peifang Tian et al.; "Ultrafast measurement of two–photon absorption by loss modulation"; Optics Letters, vol. 27, No. 18; Sep. 15, 2002; pp. 1634–1636.

Sergey Yeremenko et al.; "Frequency–resolved pump–probe characterization of femtosecond infrared pulses"; Optics Letters, vol. 27, No. 13; Jul. 1, 2002; pp. 1171–1173.

Vladimir Kalosha et al.; "Generation of Single Dispersion Precompensated 1–fs Pulses by Shaped–Pulse Optimized High–Order Stimulated Raman Scattering"; Physical Review Letters, vol. 88, No. 10; Mar. 11, 2002; pp. 103901-1–13901-4.

A. Baltuska et al.; "Attosecond control of electronic processes by intense light fields"; Nature magazine, vol. 421; Feb. 6, 2003; pp. 611–615.

T.C. Weinacht et al.; "Controlling the shape of a quantum wavefunction"; Nature magazine, vol. 397; Jan. 21, 1999; pp. 233–235.

Arjan H. Buist et al.; "Probing microscopic chemical environments with high–intensity chirped pulses"; Optics Letters, vol. 24, No. 4; Feb. 15, 1999; pp. 244–246.

D.J. Maas et al.; "Population transfer via adiabatic passage in the rubidium quantum ladder system"; Physical Review A, vol. 59, No. 2; Feb. 1999; pp. 1374–1381.

Zohar Amitay et al.; "Phase–tailoring molecular wave packets to time shift their dynamics"; Chemical Physics 267; 2001; pp. 141–149.

T.C. Weinacht et al.; "Coherent learning control of vibrational motion in room temperature molecular gases"; Chemical Physics Letters 344; 2001; pp. 333–338.

R. van Leeuwen et al.; "Manipulation of differential electron yields via autoionizing wave–packet control"; Physical Review A, vol. 63; 2001; pp. 033403-1–033403-5.

C. Rangan et al.; "Optimally shaped terahertz pulses for phase retrieval in a Rydberg–atom data register"; Physical Review A, vol. 64; 2001; pp. 0033417-1–0033417-5.

Nirit Dudovich et al.; "Transform–Limited Pulses Are Not Optimal for Resonant Multiphoton Transitions"; Physical Review Letters, vol. 86, No. 1; Jan. 1, 2001; pp. 47–50.

Dan Oron et al.; "Quantum control of coherent anti–Stokes Raman processes"; Physical Review A, vol. 65; 2002; pp. 043408-1–043408-4.

Nirit Dudovich et al.; "Coherent Transient Enhancement of Optically Induced Resonant Transitions"; Physical Review Letters, vol. 88, No. 12; Mar. 25, 2002; pp. 123004-1–123004-4.

Jerome Degert et al.; Relization of a Time–Domain Fresnel Lens with Coherent Control; Physical Review Letters, vol. 89, No. 20; Nov. 11, 2002; pp. 203003-1–203003-4.

M. Wollenhaupt et al.; "Interferences of Ultrashort Free Electron Wave Packets"; Physical Review Letters, vol. 89, No. 17; Oct. 21, 2002; pp. 173001-1–173001-4.

R. Teets et al.; "Coherent Two–Photon Excitation by Multiple Light Pulses"; Physical Review Letters, vol. 38, No. 14; Apr. 4, 1977; pp. 760–764.

B. Broers et al.; "Large interference effects of small chirp observed in two–photon absorption"; Optics Communications 91; 1992; pp. 57–61.

R.R. Jones; "Multiphoton Ionization Enhancement Using Two Phase–Coherent Laser Pulses"; Physical Review Letters, vol. 75, No. 8; Aug. 21, 1995; pp. 1491–1494.

D.J. Maas et al.; "Vibrational ladder climbing in NO by ultrashort infrared laser pulses"; Chemical Physics Letters 270; May 16, 1997; pp. 45–49.

Christopher J. Bardeen et al.; "Quantum control of $I_2$ in the gas phase and in condensed phase solid Kr matrix"; J. Chem. Phys., vol. 106, No. 20; May 22, 1997; pp. 8486–8503.

D.J. Maas et al.; Vibrational ladder climbing in NO by (sub)picosecond frequency–chirped infrared laser pulses: Chemical Physics Letters 290; 1998; pp. 75–80.

Vladislav V. Yakovlev et al.; "Chirped pulse enhancement of multiphoton absorption in molecular iodine"; Journal of Chemical Physics, vol. 108, No. 6, Feb. 8, 1998; pp. 2309–2313.

Radoslaw Uberna et al.; "Phase and amplitude control in the formation and detection of rotational wave packets in the E1Eg state of Li2"; Journal of Chemical Physics, vol. 108, No. 22; pp. 9259–9274.

John M. Papanikolas et al.; "Erratum: Manipulation of rovibrational wave packet composition in the Li2 E(Eg) shelf state using intermediate state selection and shaped femtosecond laser pulses"; J. Chem Phys. 107, 4172; 1997; p. 10830.

T.C. Weinacht et al.; "Measurement of the Amplitude and Phase of a Sculpted Rydberg Wave Packet"; Physical Review Letters; vol. 80, No. 25; Jun. 22, 1998; pp. 5508–511.

Radoslaw Uberna et al.; "Phase control of wavepacket dynamic using shape femtosecond pulses"; Faraday Discuss, vol. 113; 1999; pp. 385–400.

T.C. Weinacht et al.; "Toward Strong Field Mode–Selective Chemistry"; J. Phys. Chem. A, vol. 103, No. 49; 1999; pp. 10166–10168.

Mohamed Aziz Bouchene et al.; "Wavepacket interferometry with chirped pulses"; J. Phys. B At. Mol. Opt. Phys. 32; 1999; pp. 5167–5177.

D.J. Maas et al.; "Rotational interference in vibrational ladder climbing in NO by chirped infrared laser pulses"; Physical Review A, vol. 60, No. 2; Aug. 1999; pp. 1351–1362.

R. van Leeuwen et al.; "Coherent Control of the Energy and Angular Distribution of Autoionized Electrons"; Physical Review Letters, vol. 82, No. 14; Apr. 5, 1999; pp. 2852–2855.

Celine Nicole et al.; "Saturation of wave–packet interferences: Direct observation of spin precision in potassium atoms"; Physical Review A, vol. 60, No. 3; Sep. 1999; pp. R1755–R1758.

Mohamed Aziz Bouchene et al.; "Interplay between wave packet interferences and second harmonic generation"; Optics Communications 181; 2000; pp. 327–336.

Radoslaw Uberna et al.; "Ultrafast spectroscopy of wavelength–dependent coherent photoionization cross sections of Li2 wave packets in the E1Eg state: The role of Rydberg states"; Journal of Chemical Physics, vol. 114, No. 23; Jun. 15, 2001; pp. 10311–1320.

Lorenzo Pesce et al.; "Quantum dynamics simulation of the ultrafast photoionization of Li2"; Journal of Chemical Physics, vol. 114, No. 3; Jan. 15, 2001; pp. 1259–1271.

M.F. DeCamp et al.; "Dynamics and coherent control of high–amplitude optical phonons in bismuth"; Physical Review B, vol. 64; 2001; pp. 092301–1–092301–3.

J. Ahn et al.; "Quantum Phase Retrieval of a Rydberg Wave Packet Using a Half–Cycle Pulse"; Physical Review Letters, vol. 86, No. 7; Feb. 12, 2001; pp. 1179–1182.

Sebastien Zamith et al.; "Observation of Coherent Transients in Ultrashort Chirped Excitation of an Undamped Two–Level System"; Physical Review Letters, vol. 87, No. 3; Jul. 16, 2001; pp. 033001–1–033001–4.

Hans U. Stauffer et al.; "Simultaneous phase control of $Li_2$ wave packets in two electronic states"; Journal of Chemical Physics, vol. 116, No. 3; Jan. 15, 2002; pp. 946–954.

Joshua B. Ballard et al.; "Optimization of wave packet coefficients in Li 2 using an evolutionary algorithm: The role of resonant and nonresonant wavelengths"; Journal of Chemical Physics, vol. 116, No. 4; Jan. 22, 2002; pp. 1350–1360.

Elizabeth Mirowski et al.; "Effect of nonresonant frequencies on the enhancement of quantum beat amplitudes in rovibrational states of Li2: The role of state spacing"; Journal of Chemical Physics, vol. 117, No. 24; Dec. 22, 2002; pp. 11228–11238.

S.N. Pisharody et al.; "Phase–controlled stair–step decay of autoionizing radial wave packets"; Physical Review A, vol. 65; 2002; pp. 033418–1–033418–10.

R. Netz et al.; "Coherent population dynamics of a three–level atom in spacetime"; Physical Review A, vol. 65; pp. 043406–1–043406–12.

Joshua B. Ballard et al.; "Simultaneous control of time–dependent population transfer dynamics and wave–packet quantum interferences in Li2 by shaped ultrafast pulses"; Physical Review A 66; 2002; pp. 043402–1–043402–7.

Dan Oron et al.; "Narrow–Band Coherent Anti–Stokes Raman Signals from Broad–Band Pulses"; Physical Review Letters, vol. 88, No. 6; Feb. 11, 2002; pp. 063004–1–063004–4.

M.M. Salour et al.; "Observation of Ramsey's Interference Fringes in the Profile of Doppler–Free Two–Photon Resonances"; Physical Review Letters, vol. 38, No. 14; Apr. 4, 1977; pp. 757–760.

N.F. Scherer et al.; "Time resolved dynamics of isolated molecular systems studied with phase–locked femtosecond pulse pairs"; J. Chem Phys. vol. 93, No. 1; Jul. 1, 1990; pp. 856–857.

J.S. Melinger et al.; "Adiabatic population inversion in $I_2$ vapor with picosecond laser pulses"; J. Chem. Phys. vol. 95, No. 3; Aug. 1, 1991; pp. 2210–2213.

J.J. Gerdy et al.; "Femtosecond selective control of wave packet population"; Chemical Physics Letters, vol. 171, No. 1, /2; Jul. 27, 1990; pp. 1–4.

Norbert F. Scherer et al.; "Fluorescence–detected wave packet interferometry: Time resolved molecular spectroscopy with sequences of femtosecond phase–locked pulses"; J. Chem. Phys., vol. 95, No. 3; Aug. 1, 1991; pp. 1487–1511.

N.F. Scherer et al.; "Fluorescence–detected wave packet interferometry. II. Role of rotations and determination of the susceptibility"; J. Chem. Phys., vol. 96, No. 6; Mar. 15, 1992; pp. 4180–4194.

L.D. Noordam et al.; "Redistribution of Rydberg States by Intense Picosecond Pulses"; Physical Review Letters, vol. 68, No. 10; Mar. 9, 1992; pp. 1496–1499.

J.S. Melinger et al.; "Generation of Narrowband Inversion with Broadband Laser Pulses"; vol. 68, No. 13; Mar. 30, 1992; pp. 2000–2003.

B. Broers et al.; "Efficient Population Transfer in a Three–Level Ladder System by Frquency–Swept Ultrashort Laser Pulses"; Physical Review Letters, vol. 69, No. 14; Oct. 5, 1992; pp. 2062–2065.

B. Broers et al.; "Diffraction and focusing of spectral energy in multiphoton processes"; Physical Review A, vol. 46, No. 5; Sep. 1, 1992; pp. 2749–2756.

R.R. Jones et al.; "Ramsey Interference in Strongly Driven Rydberg Systems"; Physical Review Letters, vol. 71, No. 16; Oct. 18, 1993; pp. 2575–2578.

J.F. Christian et al.; "Rubidium electronic wavepackets probed by a phase–sensitive pump–probe technique"; Optics Communications, vol. 103, No. 1/2; Nov. 1, 1993; pp. 79–84.

J.S. Melinger et al.; "Adiabatic population transfer with frequency–swept laser pulses"; J. Chem. Phys. vol. 101, No. 8; Oct. 15, 1994; pp. 6439–6454.

P. Balling et al.; "Interference in climbing a quantum ladder system with frequency–chirped laser pulses"; Physical Review A, vol. 50, No. 5; Nov. 1994; pp. 4276–4285.

D.W. Schumacher et al.; "Phase Dependence of Intense Field Ionization: A Study Using Two Colors"; Physical Review Letters, vol. 73, No. 10; Sep. 5, 1994; pp. 1344–1347.

L. Marmet et al.; "Observation of Quasi–Landau Wave Packets"; Physical Review Letters, vol. 72, No. 24; Jun. 13, 1994; pp. 3779–3782.

Valerie Blanchet et al.; "One–color coherent control in Cs2 Observation of 2.7 fs beats in the ionization signal"; Chemical Physics Letters, vol. 233; Feb. 25, 1995; pp. 491–499.

R.R. Jones et al.; "Bound–state interferometry using incoherent light"; J. Phys. B 28 At. Mol. Opt. Phys.; 1995; pp. L405–L411.

D.W. Schumacher et al.; "Programmable cesium Rydberg wave packets"; Physical Review A, vol. 52, No. 6; Dec. 1995; pp. 4719–4726.

R.R. Jones; "Interference Effects in the Multiphoton Ionization of Sodium"; Physical Review Letters, vol. 74, No. 7; Feb. 13, 1995; pp. 1091–1094.

Bern Kohler et al.; "Quantum Control of Wave Packet Evolution with Tailored Femtosecond Pulses"; Physical Review Letters, vol. 74, No. 17; Apr. 24, 1995; pp. 3360–3363.

V.A. Apkarian; "Comment on Time–resolved laser induced harpoon reactions"; J. Chem. Phys. vol. 106, No. 12; Mar. 22, 1997; pp. 5298–5299.

M. Ovchinnikov et al.; "Quantum interference in resonant Raman spectra of I2 in condensed media"; J. Chem. Phys., vol. 106, No. 13; Apr. 1, 1997; pp. 5775–5778.

Richard M. Williams et al.; "Compositional control of rovibrational wave packets in the E(1Eg) "shelf" state of $Li_2$ via quantum–state–resolved intermediate state selection"; J. Chem. Phys. vol. 106, No. 20; May 22, 1997; pp. 8310–8323.

John M. Papanikolas et al.; "Manipulation of rovibrational wave packet composition in the Li2 E(1Eg) shelf state using intermediate state selection and shaped femtosecond laser pulses"; J. Chem. Phys., vol. 107, No. 11; Sep. 15, 1997; pp. 4172–4178.

R.B. Vrijen et al.; "Limitations on quantum ladder climbing in complex systems"; Physical Review A, vol. 56, No. 3; Sep. 1997; pp. 2205–2212.

Valerie Blanchet et al.; "Temporal Coherent Control in Two–Photon Transitions: From Optical Interferences to Quantum Interferences"; Physical Review Letters, vol. 78, No. 14; Apr. 7, 1997; pp. 2716–2719.

R. Zadoyan et al.; "Wavepacket diagnosis with chirped probe pulses"; Chemical Physics, vol. 233; 1998; pp. 353–363.

M.A. Bouchene et al.; "Temporal coherent control induced by wave packet interferences in one and two photon atomic transitions"; The European Physical Journal D, vol. 2; 1998; pp. 131–141.

Valerie Blanchet et al.; "Temporal coherent control in the photoionization of Cs2: Theory and experiment"; Journal of Chemical Physics, vol. 108, No. 12; Mar. 22, 1998; pp. 4862–4876.

R.A. Bartels et al.; "Nonresonant Control of Multimode Molecular Wave Packets at Room Temperature"; Physical Review Letters, vol. 88, No. 3; Jan. 21, 2002; pp. 033001-1 through 033001-4.

J. M. Dudley, et al.; "Direct measurement of pusle distortion near the zero–disperson wavelength in an optical fiber by frequency–resolved optical gating"; Optics Letters, vol. 22, No. 7; Apr. 1, 1997; 457–459.

D. Meshulach et al.; "Adaptive real–time femtosecond pulse shaping"; J. Opt. Soc. Am. B, vol. 15, No. 5; May 1998; pp. 1615–1619.

D. Zeidler et al.; "Adaptive compression of tunable pulses from a non–collinear–type OPA to below 16 fs by feedback–controlled pulse shaping"; Appl. Phys. B 70 [Suppl.], S125–S131 (2000)/Digital Object Identifier (DOI) 10.1007/s003400000306.

David C. Clary; "Quantum Theory of Chemical Reaction Dynamics"; Science, vol. 279, Mar. 20, 1998; p. 1879.

* cited by examiner

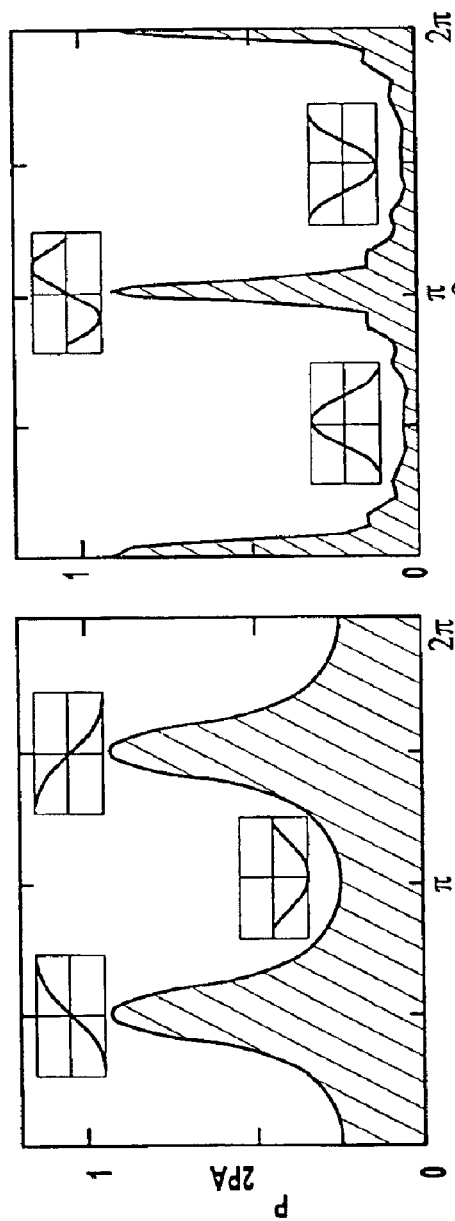
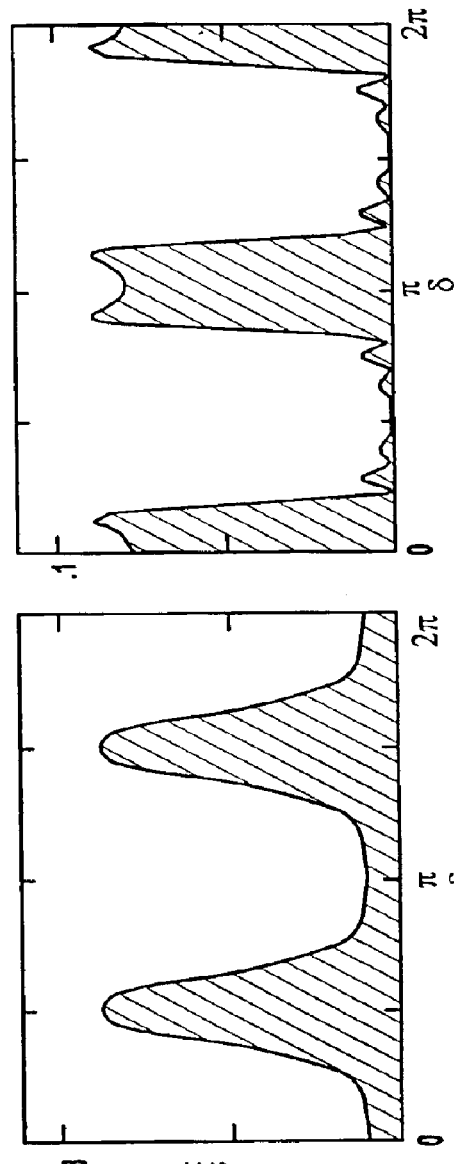
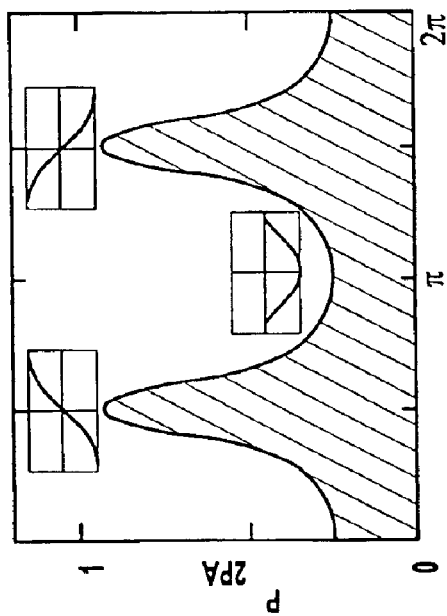
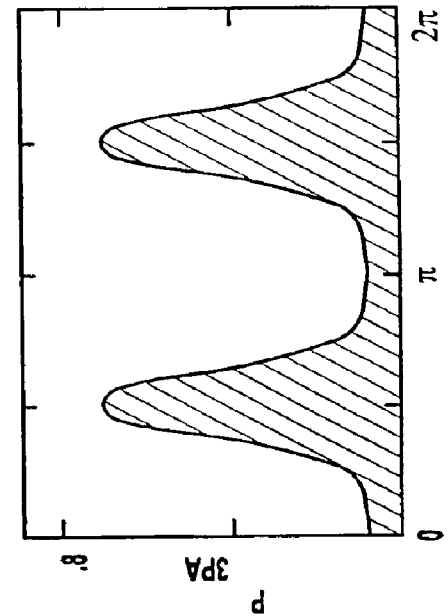
Figure - 14A
Figure - 14B
Figure - 14C
Figure - 14D

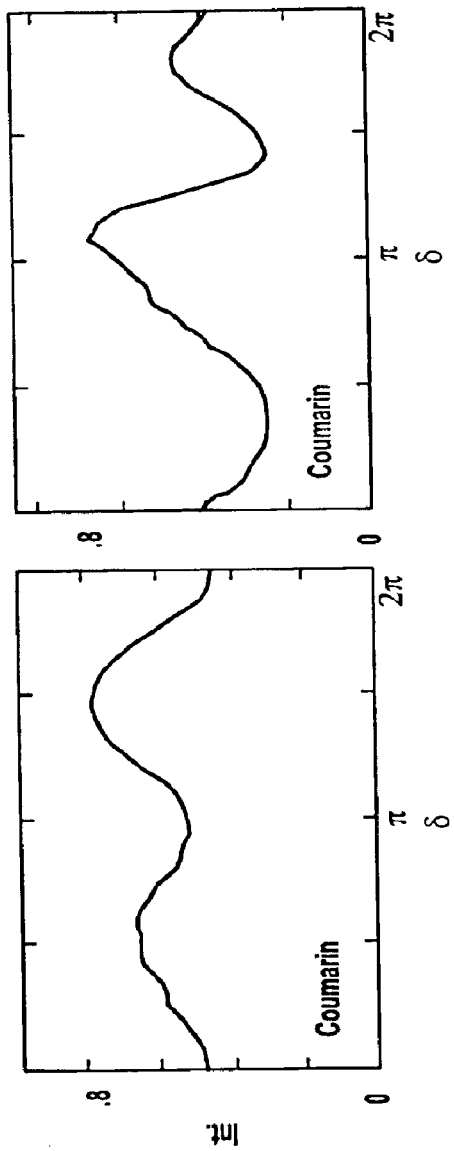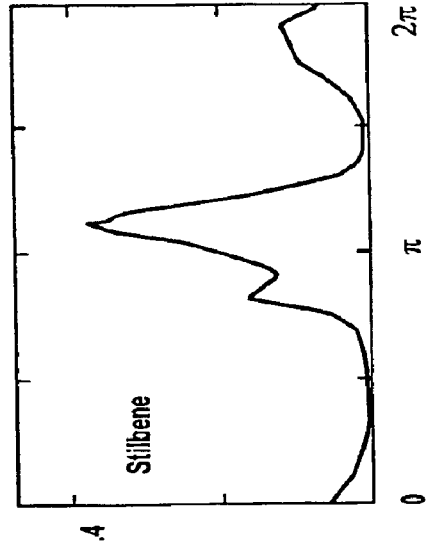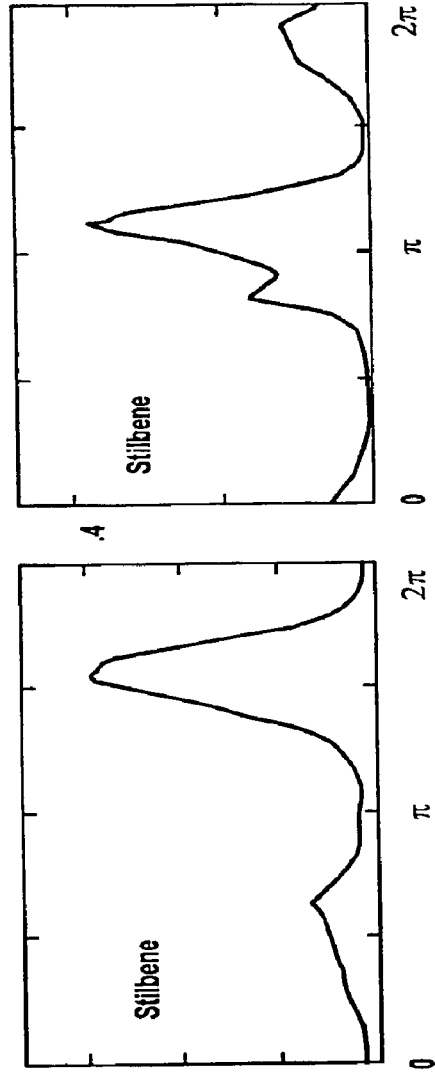
*Figure - 14E*  *Figure - 14G*
*Figure - 14F*  *Figure - 14H*

 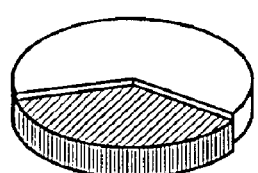
*Figure - 16A*  *Figure - 16B*
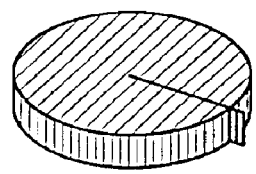 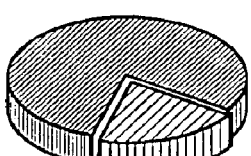
*Figure - 16C*  *Figure - 16D*
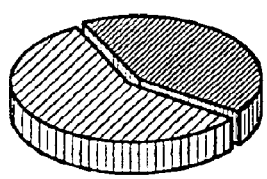 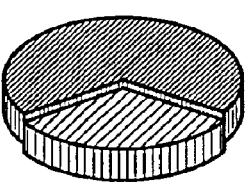
*Figure - 16E*  *Figure - 16F*

CONTROL SYSTEM AND APPARATUS FOR USE WITH LASER EXCITATION OF IONIZATION

CROSS-REFERENCE TO RELATED APPLICATIONS

This application is a continuation of PCT/US02/02548, filed Jan. 28, 2002, which claims priority to U.S. Provisional Application Ser. No. 60/265,133, filed Jan. 30, 2001.

BACKGROUND AND SUMMARY OF THE INVENTION

The present invention generally relates to control systems and apparatuses for use with laser excitation or ionization, and more particularly to a system and apparatus which employs a laser, pulse shaper, mass spectrometer and electrical control system.

Conventionally, laser desorption mass spectrometry has been used with a fixed laser beam pulse shape and computers for simple chemical analysis processes on purified molecules with or without a matrix. The laser beam pulse shape was not considered an important parameter and was not modified; whatever fixed shape was set by the manufacturer for the ultraviolet laser was used in the tests. The general concept of typically laser selective ion formation from molecules in a molecular beam is disclosed in the following publication: Assion et al., "Control of Chemical Reactions by Feedback-Optimized Phase-Shaped Femtosecond Laser Pulses," *Science,* Vol. 282, page 919 (Oct. 30, 1998). The pulse shaping process with a learning algorithm is disclosed in Judson et al., "Teaching Lasers to Control Molecules," *Physical Review Letters,* Vol. 68, No. 10, page 1500 (Mar. 9, 1992). It is noteworthy, however, that the Assion article discloses use of an 80 femtosecond laser pulse and requires molecules to be isolated in a molecular beam, while the Judson article discloses use of a one nanosecond laser pulse and is purely conceptual as it does not include experimental results.

It is also known to employ nanosecond lasers for matrix-assisted laser desorption ionization (hereinafter "MALDI"). Examples of this are disclosed in U.S. Pat. No. 6,130,426 entitled "Kinetic Energy Focusing for Pulsed Ion Desorption Mass Spectrometry" which issued to Laukien et al. on Oct. 10, 2000, and U.S. Pat. No. 6,111,251 entitled "Method and Apparatus for MALDI Analysis" which issued to Hillenkamp on Aug. 29, 2000; both of these patents are incorporated by reference herein.

Until recently, commercially practical femtosecond lasers have been unavailable. For example, lasers which can generate 10 femtosecond or less laser pulse durations have traditionally been extremely expensive, required unrealistically high electrical energy consumption (for extensive cooling, by way of example) and depended on laser dyes that had to be replenished every month thereby leading to commercial impracticality. The efficiency of sub-10 femtosecond lasers was not practical until the year 2000 because of the prior need for dyes and flash lamps instead of YAG and Ti: Sapphire crystals pumped by light or laser emitting diodes.

Furthermore, the traditional role of the laser in a mass spectrometer with MALDI is to provide energy to the matrix molecules, wherein this energy dissipates and causes evaporation and ionization of the protein analyte dissolved in it. The laser, therefore, plays an indirect role that depends on energy transfer processes that may take from picoseconds to microseconds. Because excitation is indirect, pulse wavelength has not been found to cause significant differences in the outcome. Direct laser excitation of the proteins with nanosecond lasers typically causes the proteins to char.

In contrast, the present invention uses a different approach to MALDI in which the laser plays a more active and direct role in the ionization and even selective fragmentation of the analyte proteins. Shaped femtosecond pulses are required to achieve this goal. The optimum pulse shape cannot be found using the traditional laser sources, and trial and error. This is because the search for an optimal laser pulse shape involves a very wide range of possibilities. For example, if a 100 femtosecond laser pulse is used to produce pulse trains as long as several picoseconds in duration, splitting the laser beam spectrum into at least 100 spectral components is required since the length of the pulse is roughly inversely proportional to the band width. Since each component can be attenuated in 10 steps or phases shifted over 10 angles, then there are $(10 \times 10)^{100}$ different possible pulse shapes, and it would be impractical to systemically explore even a subset of these pulse shapes through conventional trial and error methods.

Laser induced, selective chemical bond cleavage has also been explored but with fairly limited success. It is believed that very simple molecules, such a HOD (partially deuterated water), have had only the OH and OD bonds cleaved with a nanosecond narrow line laser to vibrationally excite the specimen and then an ultraviolet laser pulse was employed to perform the cleaving. The desired laser frequency for vibrational excitation could be determined a priori in the gas-phase sample. More importantly, the HOD molecule is unique because the energy can be deposited in one of the bonds and it remains there for very long times, which are longer than nanoseconds. For the HOD experiments using selective bond excitation, no appreciable pulse shaping was used. This method was not known to have been employed for a protein or MALDI process, and was not known to have been successfully used for any other atomic bonds in other molecules, especially not in a condensed phase. It is also noteworthy that MALDI, with a matrix, has been used in an attempt to perform limited bond cleavage, as is discussed in U.S. Pat. No. 6,156,527 entitled "Characterizing Polypeptides" which issued to Schmidt et al. on Dec. 5, 2000, and is incorporated by reference herein. However, the approach of Schmidt et al. does not modify and optimize the laser pulse shape or other laser properties to achieve limited bond cleavage.

In accordance with the present invention, a control system and apparatus for use with laser excitation or ionization is provided. In another aspect of the present invention, the apparatus includes a laser, pulse shaper, detection device and control system. A further aspect of the present invention employs a femtosecond laser and a mass spectrometer. In yet another aspect of the present invention, the control system and apparatus are used in a MALDI process. Still another aspect of the present invention employs the control system and apparatus to cleave chemical bonds in a specimen and/or to determine the amino acid sequence of a protein specimen. Photodynamic therapy and fiber optic communication systems use the laser excitation apparatus with additional aspects of the present invention. A method of ionizing and determining a characteristic of a specimen is also provided.

The control system and apparatus of the present invention are advantageous over conventional constructions since the present invention allows for analysis and identification of constituents of complex and unknown molecules, such as those used in a MALDI process or proteins, in a relatively quick and automated manner. The present invention advantageously determines optimum laser conditions for maximizing the sensitivity of MALDI based protein sequencing, and to examine ion formation efficiencies for various matrices using tailored laser pulses. The present invention is also advantageously used to control the degree and type of fragmentation for automated protein sequencing. Furthermore, the adaptive laser source permits the optimal desorption from an insoluble protein source and allows for ionization analysis of a protein with or without a matrix.

The present invention is advantageous by employing ultra-fast laser beam pulses which can be repeatedly transmitted onto a specimen at least 1,000 times without replacing the specimen and without significant degradation of results. The ultra-fast laser also does not over-heat or "cook" a specimen, such as a protein. Recent improvements and efficiencies of femtosecond lasers have allowed for their commercially practical usefulness with the present invention. The automated feedback and pulse shaping of the control system of the present invention enhances signal-to-background sensitivity, especially for MALDI-based protein sequencing, while also statistically optimizing the process; this leads to significant time, cost and accuracy improvements. Additional advantages and features of the present invention will become apparent from the following description and appended claims, taken in conjunction with the accompanying drawings.

BRIEF DESCRIPTION OF THE DRAWINGS

FIGS. 14A–14H are sets of laser beam pulse shapes employed with the laser excitation apparatus for two and three photon induced fluorescence;

FIGS. 16A–16F are sets of pie charts and laser beam pulse shape graphs showing contrast ratios of the laser excitation apparatus;

DETAILED DESCRIPTION OF THE PREFERRED EMBODIMENT

Figure 1:
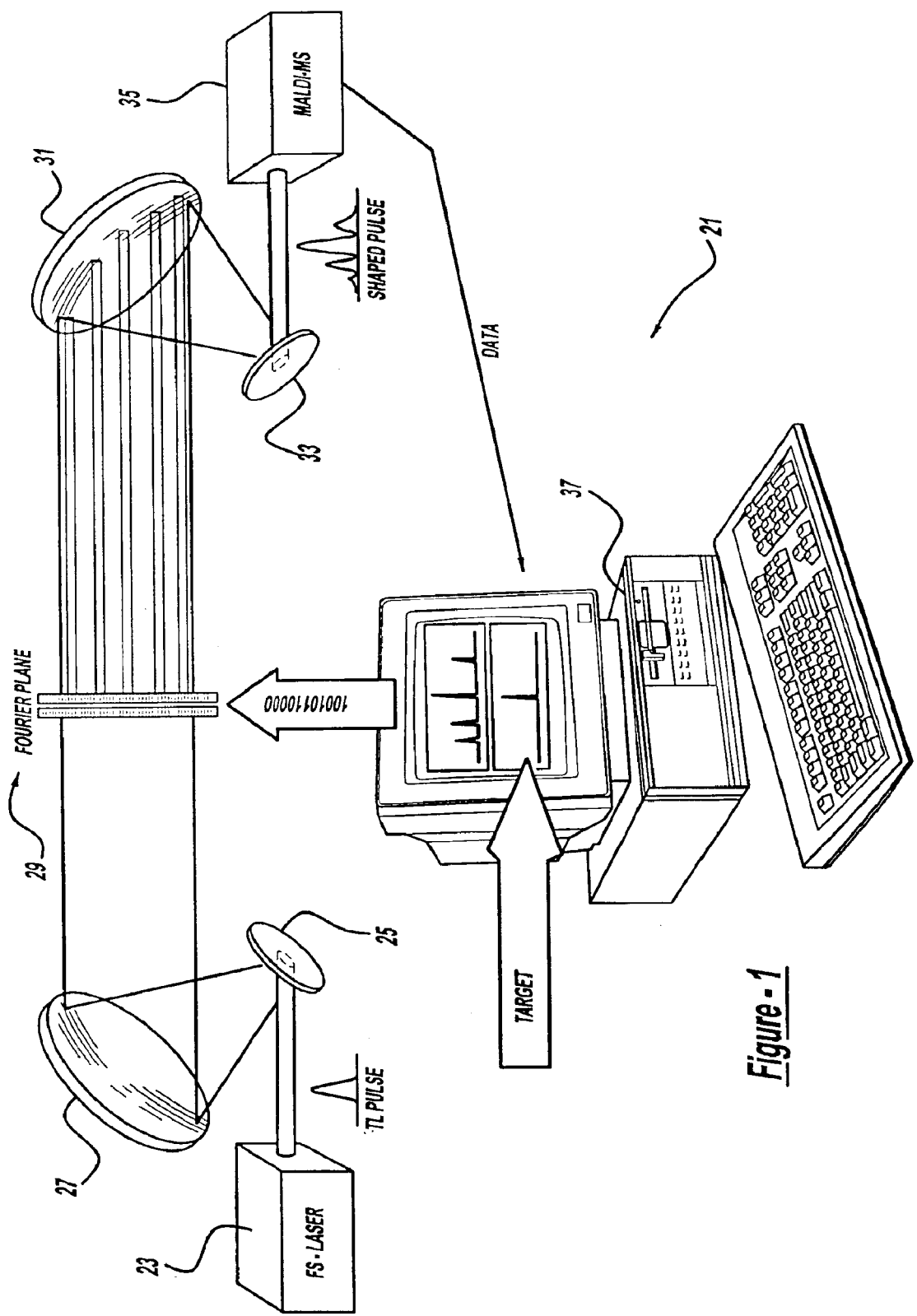
FIGS. 1 through 3 are diagrammatic views showing a first preferred embodiment of a control system and apparatus of the present invention.
Figure 2:
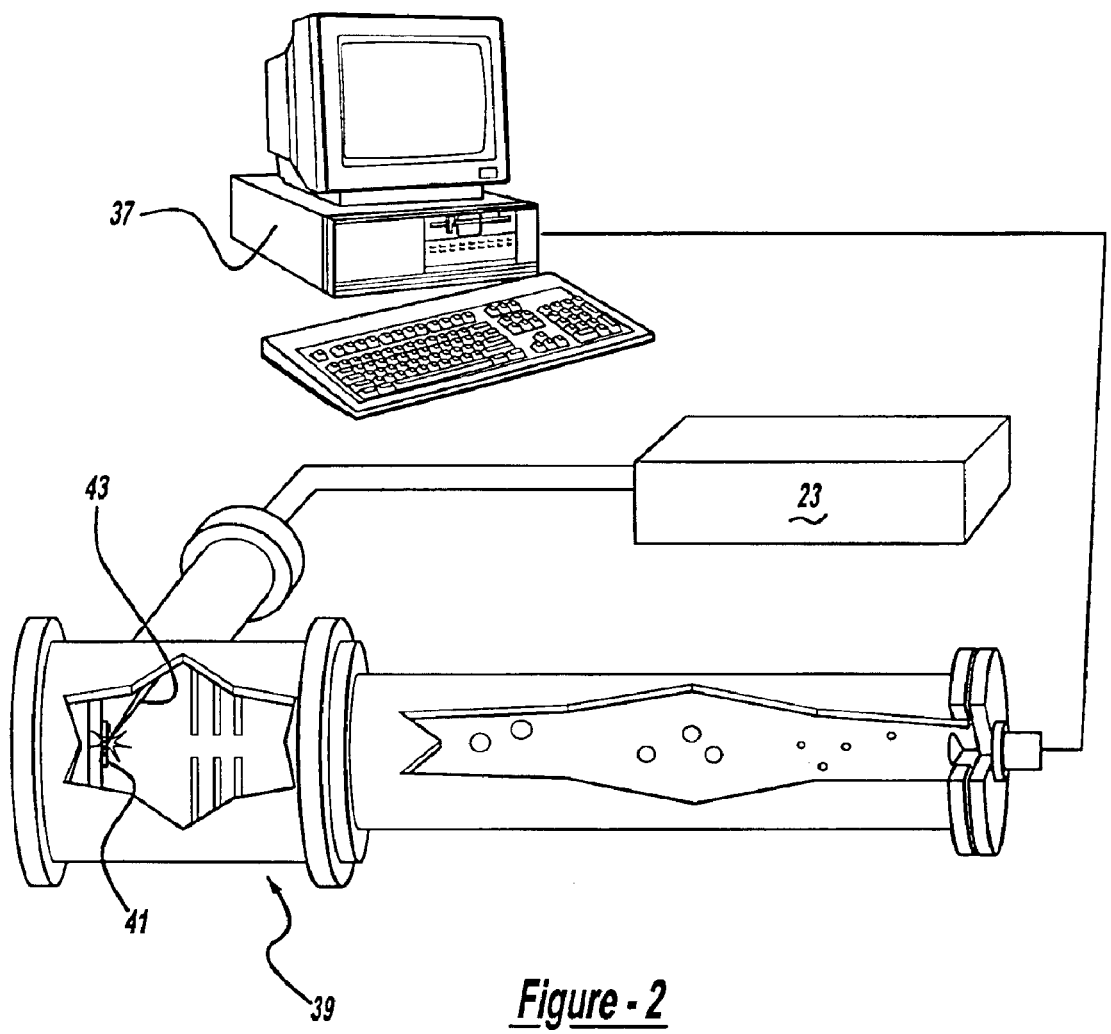

The first preferred embodiment of a control system and apparatus 21 of the present invention for use with laser excitation or ionization is generally shown in FIGS. 1 and 2. Apparatus 21 includes a femtosecond laser 23, an upstream grating 25, an upstream convex mirror 27, a laser beam pulse shaper 29, a downstream concave mirror 31, a downstream grating 33, a matrix-assisted laser desorption ionization device 35, and a personal computer 37. Personal computer 37 has a microprocessor based electrical control system, an output screen, a data storage device, an input keyboard, and a removable disk. More specifically, the MALDI device provides a time-of-flight mass spectrometer ("TOF MS") 39. A sample or specimen 41 to be analyzed is placed within mass spectrometer 39. Bursts or pulses of a laser beam 43 are emitted from laser 23, through the optics 25, 27, 31 and 33, as well as through pulse shaper 29, and onto specimen 41; this causes fragmentation and ionization of a top layer of the specimen for detection and sensing by mass spectrometer 39 for further evaluation, analysis, comparison and subsequent control by personal computer 37.

The laser is preferably an ultra-fast femtosecond and high peak intensity (with a typical peak greater than $10^{10}$ watts/$cm^2$) laser which preferably emits laser beam pulses of less than 100 femtosecond duration, and more preferably at or less than 50 femtoseconds, and for certain applications (such as, but not limited to, sequencing) even more preferably at or less than 10 femtosecond duration, for each pulse burst or shot. The intense optical pulses that are required to modify material are formed in a Kerr-Lens modelocked titanium sapphire oscillator. Such lasers are capable of producing hundreds of nanometers of coherent bandwidth, although only about 10 nm are typically used. The output is amplified in a 1 kHz regenerative chirped pulsed amplifier. The output pulse is typically 100 fs long with a central wavelength of out 790 nm and total pulse energy of 0.1 to 1 mJ. Preferred lasers include: the Hurricane model from Spectra Physics Inc., which is diode pumped and gives 0.8 mJ per pulse with sub-50 fs pulses at 1 kHz; and the CPA-2001+ model from Clark-MXR Inc., which gives 1.3 mJ per pulse with sub-150 fs pulses at 1 kHz, pumping a Clark-MXR Inc. non-collinear parametric amplifier (hereinafter "NOPA") which produces 0.2 mJ per pulse, and is capable of generating sub-20 fs pulses. This NOPA system can even produce pulses between 10 fs and 4.5 fs.

A VESTEC 2000 MALDI TOF mass spectrometer is believed to be suitable for this invention, although most commercial MALDI instruments can be adapted with the to femtosecond laser, pulse shaper and feedback learning control method described herein. During extraction, all of the ions obtain the same energy in the 30-kV ion acceleration region, and because K.E.=½ $mv^2$, the lightest ions achieve the highest velocity and, thus, reach the detector first. This transient (for example, having a duration of 300 microseconds) mass spectrum is recorded by a transient recorder at the detector. It is common practice to sum many (10–100) of this transient mass spectra to produce a sound spectrum from an ion-counting statistics criterion.

Figure 3:
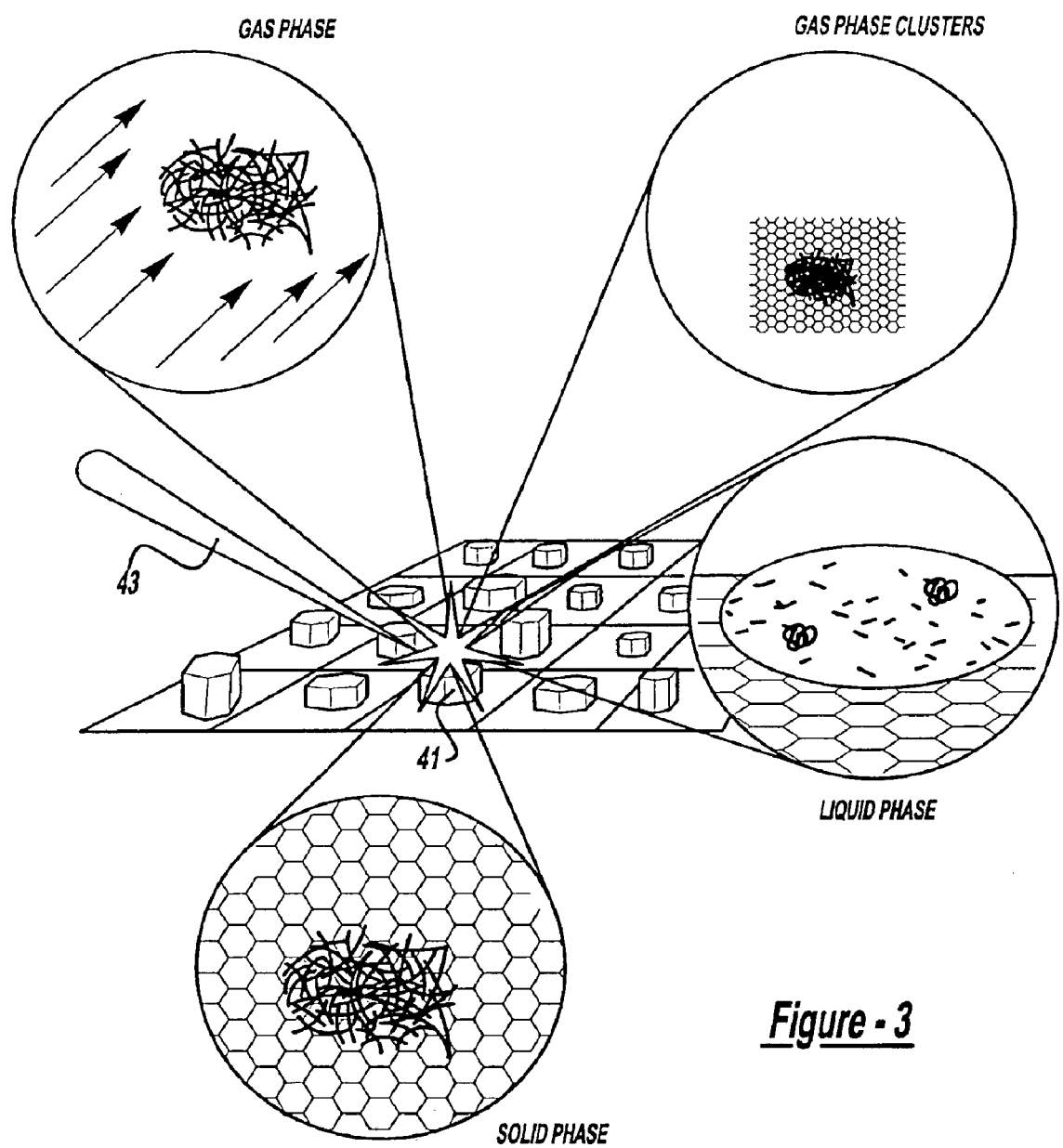

In FIG. 3, a conceptual schematic is shown outlining the four probable mechanisms theorizing where the proton transfer takes place. The laser impinges on matrix crystal specimen 41 creating a plume of highly charged particles. Some of the particle are proton rich, such as $M2H^+$ and are good proton donors. Gas phase collisions with the large and slow moving proteins may lead to the formation of the protonated analyte. Other gas-borne particles include clusters containing the naturally charged analyte and matrix molecules. As the clusters evaporate, the charged analyte remains. Alternatively, the laser causes local melting of the crystal. The proton transfer occurs in the liquid phase between the excited state (high acidity) matrix molecules and the analyte. Finally, the proton transfer could also occur in the solid phase. The excitons created by the laser near the protein can relax by reactive processes such as proton transfer. At present, it is unknown where the ionization step takes place.

A Fourier plane pulse shaper is preferably used with the present invention. Ultra-fast laser pulses contain from one to fifty optical cycles, and last only a few to femtoseconds. This is much faster than most current electronics and therefore shaping with fast time gates is very difficult. On the other hand, as a consequence of the uncertainty principle, the optical spectrum spans tens to hundreds of nanometers. Such a large bandwidth is relatively easy to measure and to filter, and there are several techniques to shape the spectrum in the frequency domain, and thereby shape the temporal pulse upon recompression.

In order to access the frequency domain and the individual frequency components that comprise the pulse, a geometric arrangement is employed, using two back-to-back spectrometers. The spectrometers are especially designed to introduce no net temporal dispersion: that is, all colors pass through the spectrometers within the same amount of time. The first spectrometer (including grating 25 and mirror 27) spreads the unshaped pulse spectrum along a line according to its dispersion function $y(\alpha)$. The light intercepts spatial amplitude and phase mask pulse shaper 29 at this point. The mask output then forms the entrance to a second spectrometer (including grating 33 and mirror 31) which recombines the colors into a single shaped pulse.

The heart of pulse shaper 29 is the programmable 256 pixel liquid-crystal mask (consisting of two overlapping 128 pixel liquid crystal arrays) that is placed at the Fourier plane. This mask must be capable of either attenuating the individual colors or shifting their phase. For alternate embodiment pulse shapers, two different electronically programmable masks that are capable of controlling both amplitude and phase have been demonstrated: a liquid crystal display ("LCD") and an acousto-optic modulator ("AOM"). A LCD pulse shaper can be obtained from CRI Co. and has a modulator electronic driver.

The AOM consists of an anti-reflection coated Tellurium Dioxide (TeO2) crystal with a piezo electric transducer glued onto one end. The central frequency of the acoustic wave is $\alpha c/2\pi = 200$ MHz. The acoustic velocity vs in the crystal is 4.2 km/s and the light pulse spends less than 10 ps in the crystal, so the acoustic wave moves less than $0.002\ \lambda$ acoustic during the transit of the light field through the crystal. Since the acoustic wave is essentially frozen as the optical pulse travels through the crystal, the complex amplitude of the acoustic wave traveling through the crystal in the y direction, $A(t)\cos \alpha ct = A(y/vs)\cos \alpha ct$, is mapped onto the optical field $E(\alpha)$ as it passes through the AOM. If some of the dispersed optical field encounters a weak acoustic wave, that frequency is attenuated; if the acoustic wave carrier is shifted by phase angle ø, that phase shift is imposed on the optical field. This pulse shaper has a total efficiency of about 20% including the diffraction efficiency of the AOM and the diffraction efficiency of the gratings. The diffracted light is used and the undiffracted "zero order" beam is blocked, to allow full modulation of both amplitude and phase in the shaped beam. The shaped beam than has the form $$E_{shaped}(\omega) = E_{input}(\omega) x \alpha(\omega) x e^{i\phi(\omega)t} \quad [1]$$

where $\alpha(\omega)e^{i\phi(\omega)} = A[y(\omega)/v_s]$; $\alpha$ is the frequency, and e is a constant.

The shaped pulses are measured using spectral interferometry. In this technique, the shaped laser pulse is joined with an unshaped reference pulse on a beam splitter, and then the combined pulses are analyzed in a spectrometer. The signal corresponds to a spectrally resolved interference. If the reference pulse is known to have a flat spectral phase, then the amplitude beating of the output beam is a direct measure of the spectral phase function.

The pulse shaping devices and methods can be further achieved as discussed within the following publications: A. M. Weiner, "Femtosecond Pulse Shaping Using Spatial Light Modulators," *Review of Scientific Instruments*, Vol. 71, No. 5, P. 1929 (May 2000); and J. X. Tull; "High-Resolution, Ultrafast Laser Pulse Shaping and its Applications," *Advances in Magnetic and Optical Resonance*, Vol. 20, P. 1 (1997). Fixed pulse shaping optics, such as chirped mirrors, can also be employed as will be discussed further hereinafter.

Figure 5A:
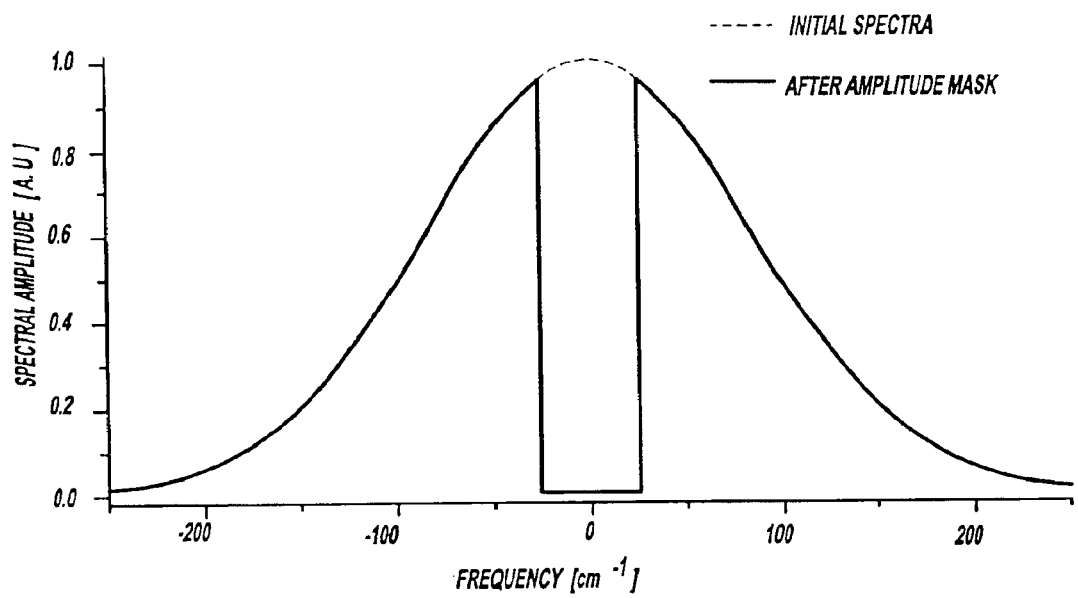
FIGS. 5A through 7B are sets of laser beam pulse shapes employed with the first preferred embodiment control system and apparatus.
Figure 5B:
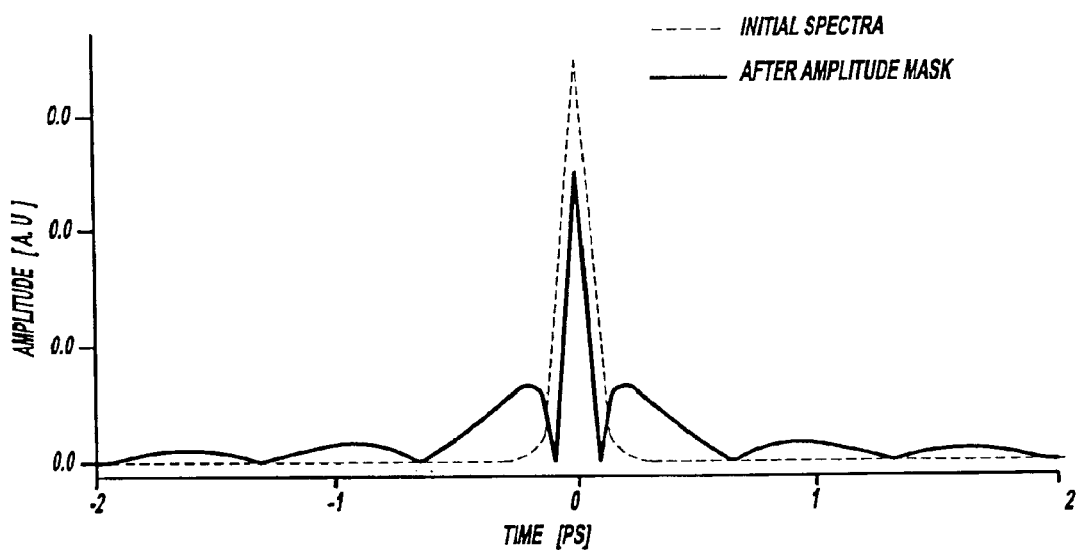
Figure 6A:
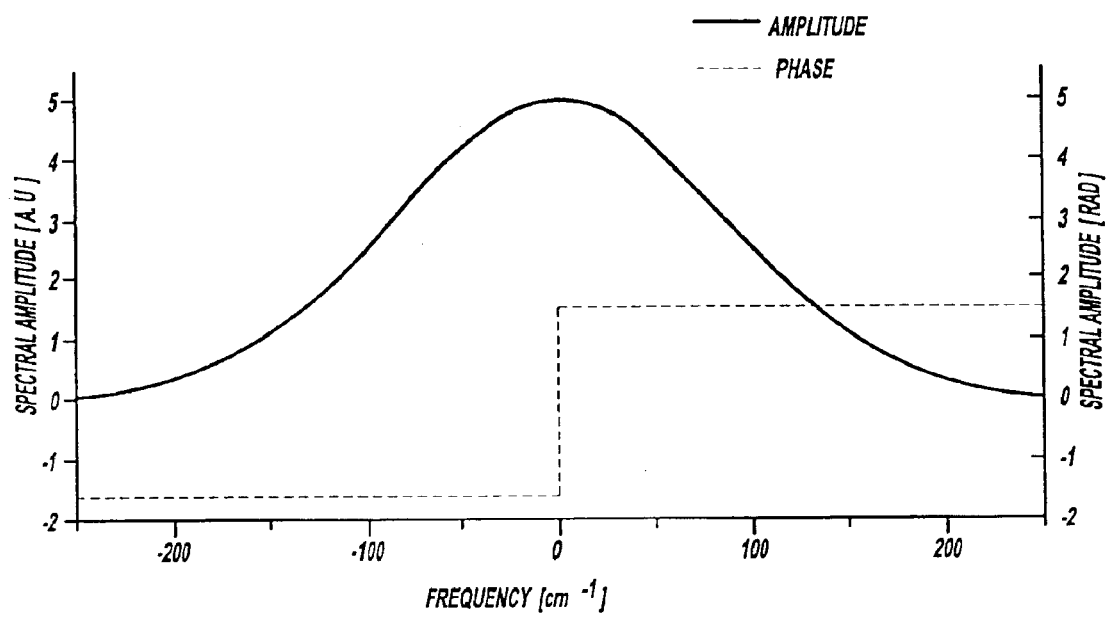
Figure 6B:
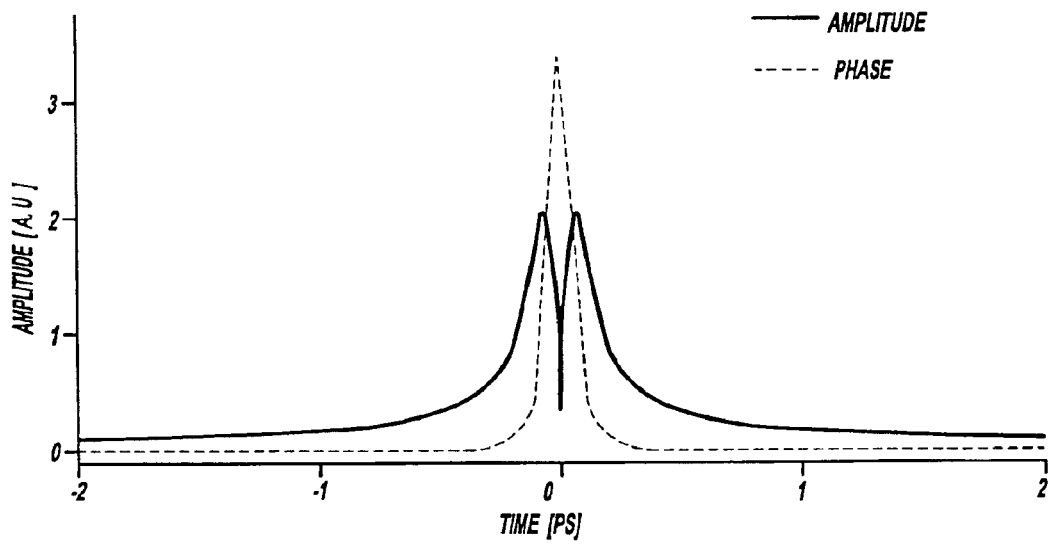
Figure 7A:
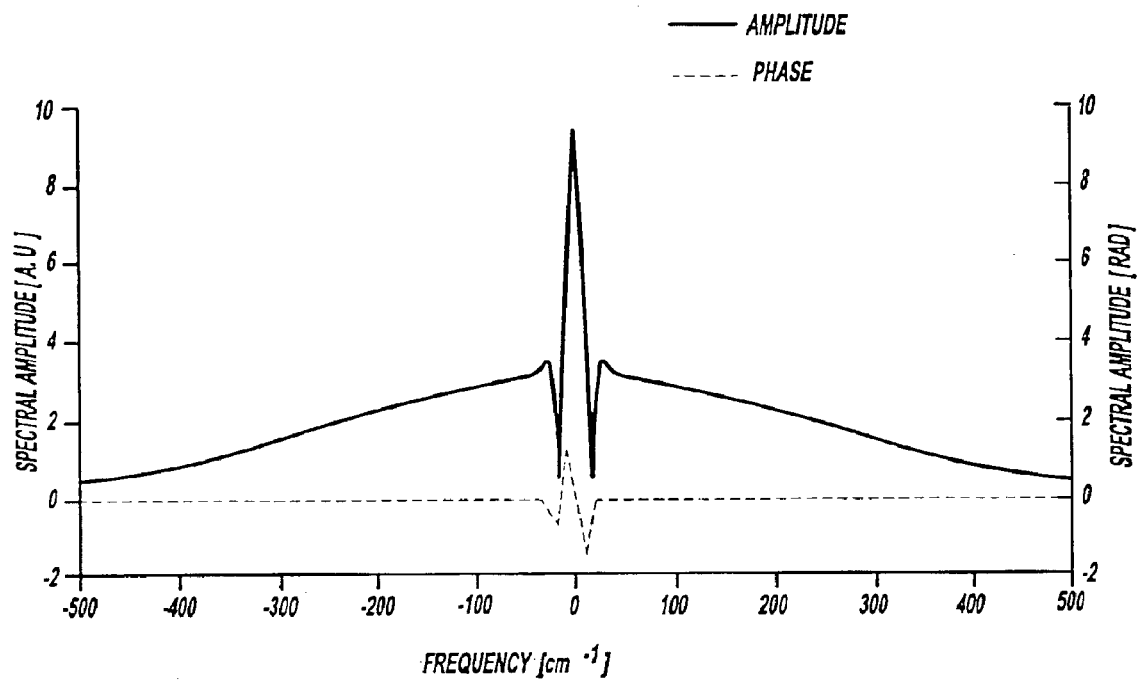
Figure 7B:
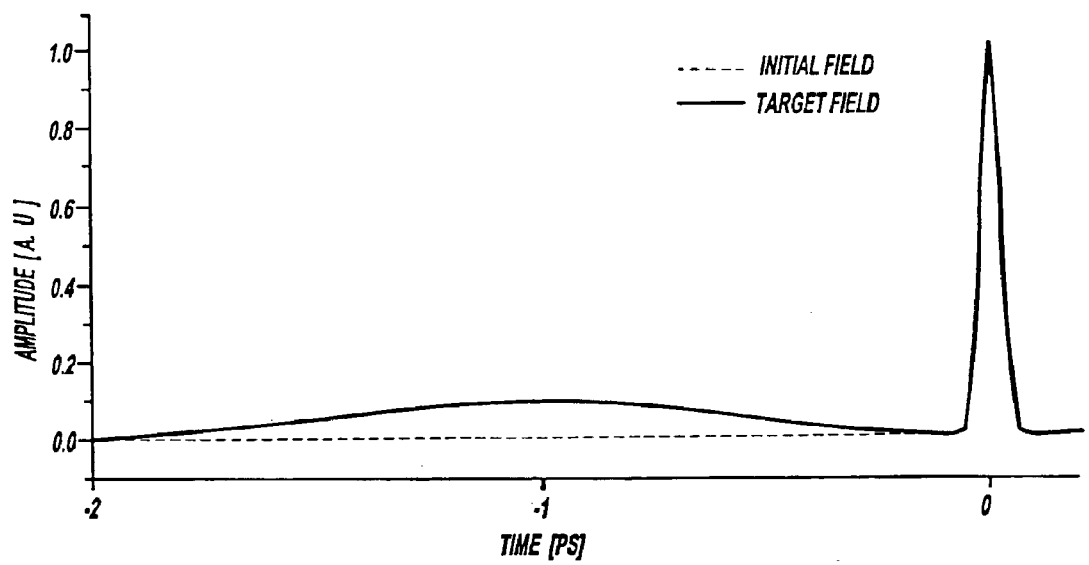

The transform limited pulses ("TL"), having all their frequencies in phase, are fed into the pulse shaper where curved mirror 27 focuses the spectrum onto Fourier plane 29. Changes in the phase ø and amplitude A of the spectral components indicated by the computer are used to tailor the laser pulse before reconstruction with second curved mirror 31 and grating 33. Once compressed, the shaped pulse is directed to mass spectrometer 39 for evaluation. The Fourier transform relationship between the time and the frequency domain allows us to calculate the necessary mask to create a certain shaped pulse. These calculations are based on $$f(v) = \frac{1}{2\pi} \int_{\infty}^{o} f(t)e^{i2\pi vct}dt \quad [2]$$

and $$f(t) = \int_{\infty}^{o} f(v)e^{-i2\pi vct}dv \quad [3]$$

where v is the frequency in wave numbers, t is the time, and c is the speed of light. As shown in FIGS. 5A and B an amplitude mask blocking a portion of the spectrum of a laser pulse at the Fourier plane leads to the formation of large periodic wings in the shaped pulse. When the phase of different frequencies in the laser pulses changes in sign, as shown in FIGS. 6A and B, the shaped pulse becomes a pair of out of phase pulses. Combinations of phase and amplitude masks can be used to create complex shaped pulses. The ideal pulse sequence for laser-desorption may be the combination of a long pulse to melt the matrix and vaporize the analyte combined with a fast pulse to cause multiphoton ionization. This sequence is based on the observation that below threshold laser excitation in MALDI generates a plume of material with very little ionization, and the fast pulse at the tail of the sequence would provide the prompt ionization. In FIGS. 7A and B, the formation of such a pulse is illustrated. Notice that the sharp femtosecond pulse is preceded by a long picosecond pulse.

The phase and amplitude masks of the pulse shaper are controlled by computer. The adaptive laser source is part of a learning feedback method that modifies the laser pulse shape based on its success at optimizing the yield of charged proteins. Traditionally in MALDI, the laser plays a relatively passive role as the energy source. In the present application, the laser pulse shape takes a more dynamic role. Pulse shapes are envisioned which include sequences of pulses where each pulse in the sequence plays a different role, for example, melting, excitation, selective fragmentation, proton transfer and evaporation.

The physical process runs itself by means of an intelligent "feedback" method by means of an intelligent loop. The learning method tries various pulse shapes, assesses their success in achieving the desired target excitation, and uses the knowledge gained in this way to improve the pulse shapes on subsequent laser shots, all with only minimal intervention of the researcher or system user. Changing conditions are automatically corrected within the learning method or feedback loop.

Figure 4:
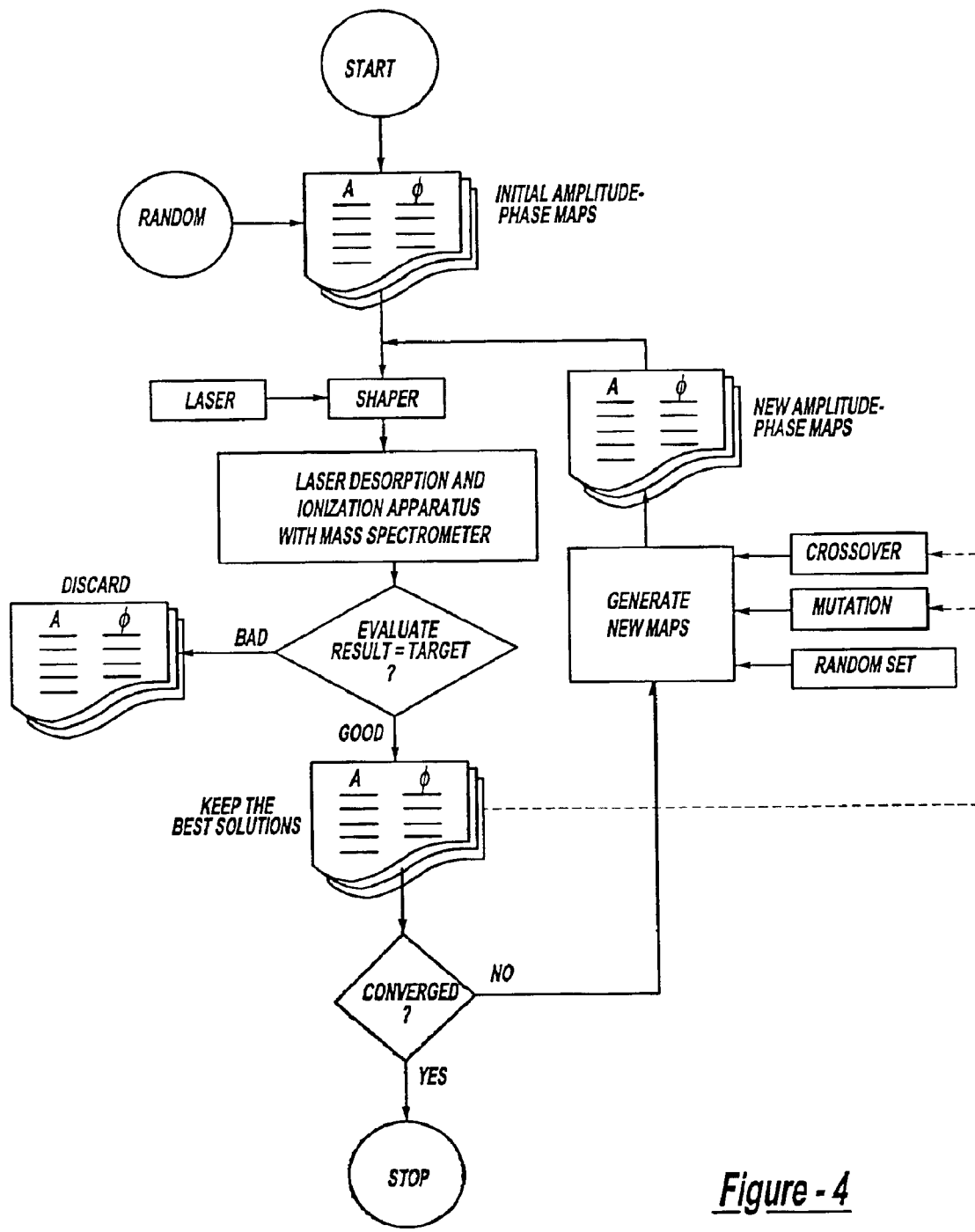
FIG. 4 is a flow chart showing the operation of the first preferred embodiment control system and apparatus.

Reference should now be made to FIG. 4. The feedback software is implemented with an initial random population of pulse shapes. Each pulse shape is characterized by a series of numbers that specify the spectral phase and amplitude in each of the wavelengths or frequencies within the pulse. This particular parameterization for the pulse shape is itself subject to optimization; this makes the algorithm adaptive. The most important part of the method is the test for fitness of a given pulse shape. Each pulse shape is tested for its ability to generate the result that most resembles a target selected in advance. For example, the program will calculate the ratio between the amplitude at the desired protein signal and the background. Once relative success is quantified, a new generation of pulse shapes is produced by mating different parts of the amplitude and phase information from pairs of the most fit pulse shapes from the current generation. In addition, the method prescribes a small probability (5%) of random changes or mutations in the successful pulse shapes. Furthermore, a new set (10%) of random pulses are introduced in order to explore entirely new regions in the parameter space. This basic series of processes is iterated until the fitness converges on a "best" value.

The convergence and robustness of the feedback method solutions can be measured in two different ways. First, the variance in the amplitude and phase information itself can be monitored. As the feedback method converges on a solution, the values fall into a narrow range that produces the best result. Over the course of many generations, some of the parameters become very stable, which is an indication that those spectral phases and amplitudes are particularly important for driving the process that determines fitness. Secondly, the information for different initial conditions is monitored. If the feedback method is working it should converge to a similar result.

New sets of parameters are created by modifying and combining elements of previous pulse shapes to create new ones. This is carried out by statistical operators that act on the phases and amplitudes of the pulse shapes. Operators that can be used include multi-point crossover, mutation, averaging, creep, smoothing, choice of phase and amplitude basis, and polynomial phase mutation. Crossover exchanges one or more sections of the phase and amplitude parameters from each of two or more pulse shapes. The resulting pulse shapes are then tested. Mutation randomly alters individual phases or amplitudes in a pulse shape. Averaging produces pulse shapes by averaging the values of two or more pulse shapes. Creep is mutation where the final parameter value is constrained to fall close to the initial value. Smoothing averages nearby phase or amplitude values in the pulse shape. Polynomial-phase mutation produces pulse shapes by replacing a portion of the parameters with a polynomial fit.

A well-chosen set of operators can greatly enhance the performance of the feedback method and lend additional physical insight. However, the proper choice is usually far from obvious, so the method is allowed to adapt itself by letting it choose how often to use a given operator to produce new pulse shapes. The use of adaptive operators helps speed up convergence, and, perhaps more importantly, it helps shed light on the control mechanism at work. For example, crossover is more effective in the beginning of the algorithm when there is maximal uncertainty, since it does a good job of mixing up the information of the initial pulse shapes. It becomes less effective as the feedback method converges to the best solutions, since at this point there is much less change in the parameters, so there is no longer a need to drastically change the information. Ideally, the learning program learns from its past mistakes and does not test possible pulse shapes which it now knows will fail, which saves a considerable amount of computing time.

For each pulse shape, a number of spectra will be obtained. The number of laser shots that are averaged per pulse shape will depend on achievement of a statistically significant spectrum. At first, when the pulse shapes are the result of random phases and amplitudes we imagine that up to 1000 repetitions may be needed to distinguish the more efficient pulse shapes. This will allow one pulse shape per second. As the selection process proceeds large gains in efficiency can be expected. The final stages of the optimization may be carried out at a rate of 100 different pulse shapes per second. The goal is to reach single pulse, femtomol sensitivity.

The learning feedback software employed in the present invention control system and apparatus is more fully described as follows. The preliminary investigation method and computer software steps for analyzing a pre-test unknown sample or specimen can be observed in FIG. 9. For any new system, the test should start with pre-defined pulse shapes in order to obtain a basic understanding of the system. Among the pre-defined pulses, the shortest pulse is expected to ionize molecules on the surface of the sample with minimum decomposition, the longest pulse is expected to mimic the nanosecond experiments where the singly protonated protein may be observed. It is also noteworthy to vary the delay between two laser pulses from a few picoseconds to a few nanoseconds in order to appreciate the time scales involved. The manual inputs of steps A through C will be initially performed by the system operator or user through entering input data into the personal computer. The microprocessor within personal computer 37 will then control laser 23 in accordance with step D, receive an essentially real time feedback input signal from mass spectrometer 39 in accordance with step F and then perform calculations, comparisons and evaluations in accordance with steps G, H and I. These automated steps can be substituted with manual user calculations and decisions if desired based on personal computer outputs.

Figure 9:
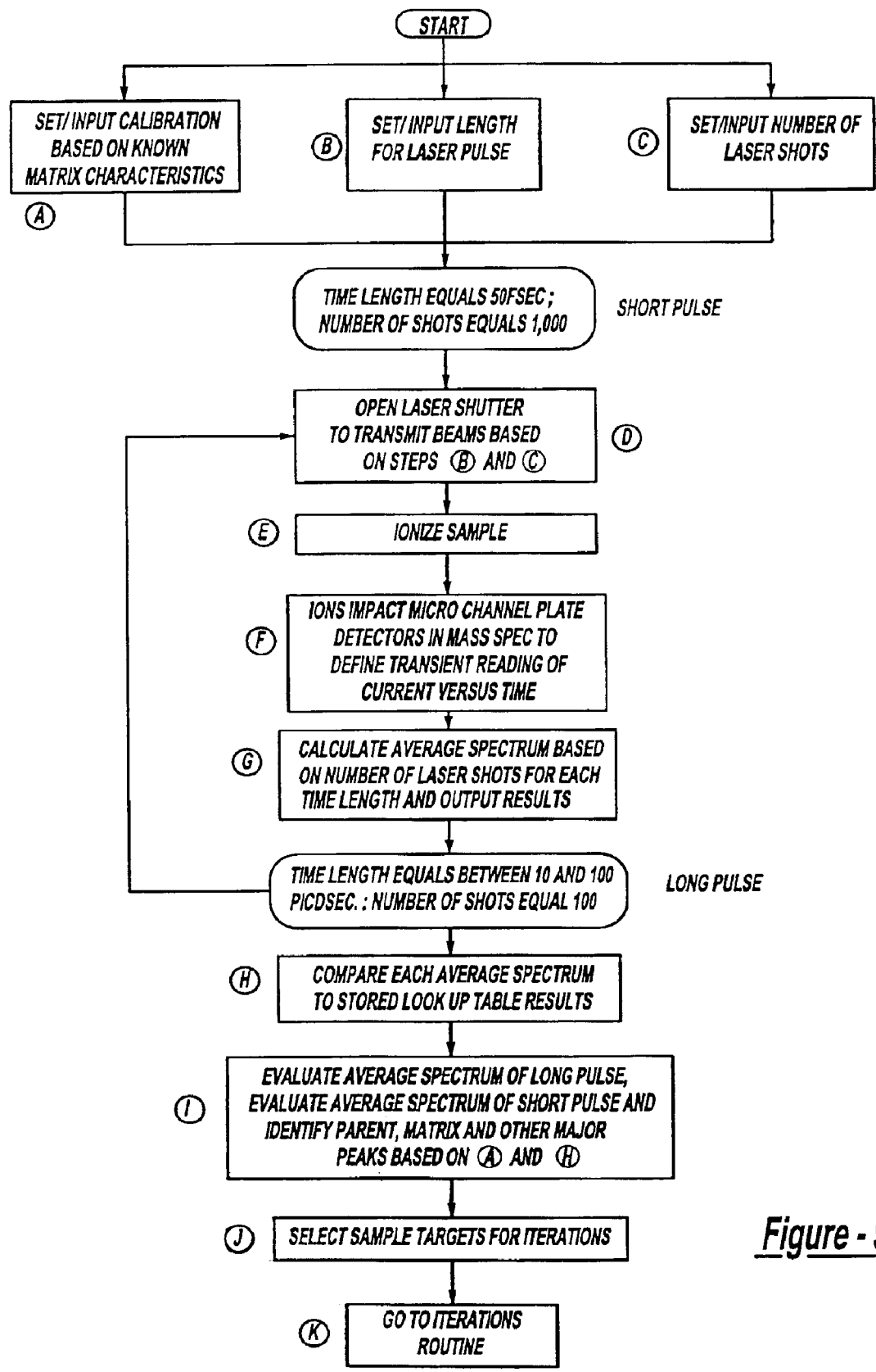
FIGS. 9 through 10B are flow charts for the method and computer software operation employed with the first preferred embodiment control system and apparatus.

The objective of the software routine of FIG. 9 is to aid in the selection of sample targets for further testing iterations for subsequent criteria data input. An optional alternate embodiment subroutine includes shooting long laser beam pulses then quick short laser beam pulses, with a separation set by an optical delay of less than ten nanoseconds. The short pulse of approximately 50 femtoseconds is performed in order to look for fragmentation and the matrix mass. Laser beam pulses of between approximately ten and 100 picoseconds are performed to look for the parent mass. The ultrafast laser beam pulse durations employed with the present invention advantageously allow for approximately 1000 laser beam shots at a single sample or specimen without significant degradation of the specimen; this allows for quicker and less expensive usage of the apparatus while also encouraging statistically more accurate results. The long and short pulse combinations can be used in addition to or without the benefit of pulse shaping. Otherwise, the control system and apparatus are the same as discussed herein.

Figure 10A:
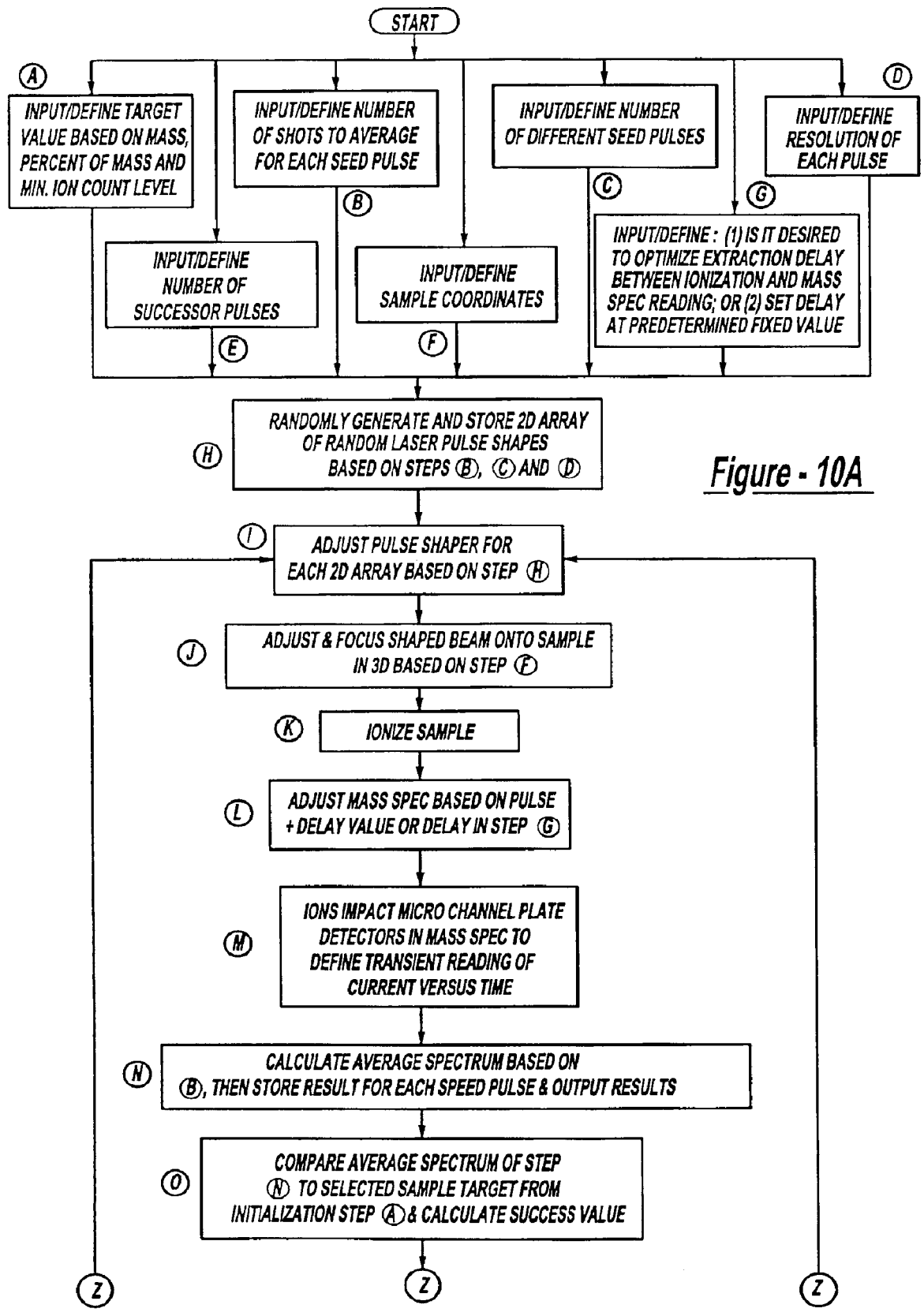
Figure 10B:
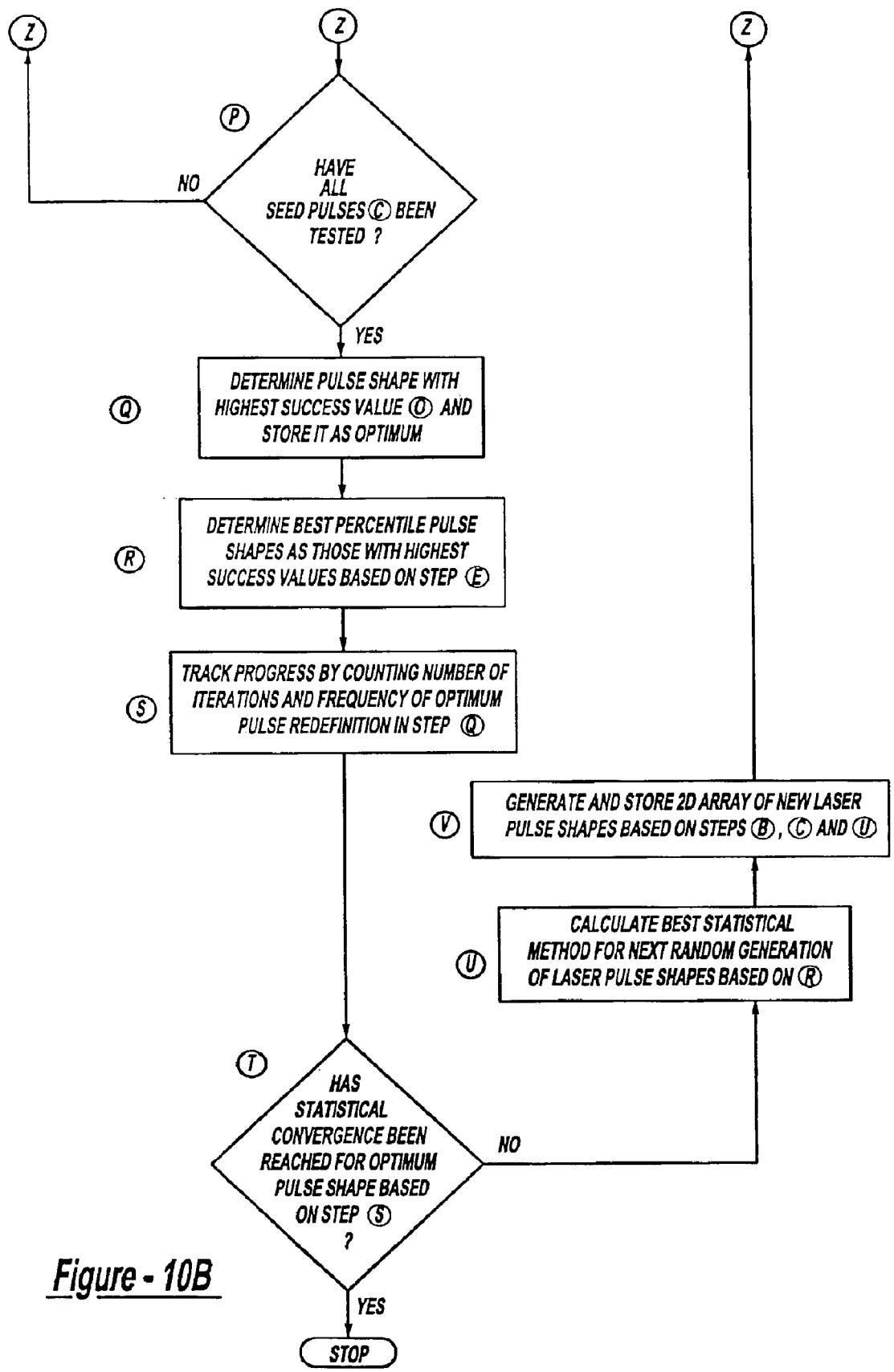

The real time learning feedback method and computer software will now be described in greater detail with regard to FIGS. 10A and 10B. This method and software are employed to statistically optimize the repetitive identification of molecularly complex and unknown samples or specimens in a highly automated and relatively quick manner. The data that is obtained in the mass spectrometer for each laser pulse consists of a two-dimensional array of numbers which are stored in random access memory of the personal computer. The first column of the array contains arrival times for the ions, when the data is obtained from the time-of-flight mass spectrometer. Equivalent numbers can be obtained from different mass spectrometry units such as quadrupole or ion-cyclotron spectrometers. This numbers can be converted to a mass assuming a charge for the species. The second number corresponds to the intensity (RI) of signal at that particular arrival time. This number correlates with the probability of detecting a charge species with that mass (see, for example, FIG. 8). The data acquisition involves collecting a number of data sets and then calculating the sum; this action is performed by the personal computer. The target is an ideal mass spectrum defined by the system user. The target can be the maximization or minimization of a signal at a particular single mass, or a number of masses with or without background suppression.

Each pulse shape is defined by a two-dimensional array of numbers which are stored in random access memory of the personal computer or otherwise accessible on a read only basis by the personal computer from a disk or the like. The length of each column determines the resolution with which the spectrum of the laser pulse is being sculpted. For a liquid spatial-light modulator, the number of pixels typically determines this number. The first column of numbers determines the amplitude transmission coefficient for every pixel. The second column determines the phase delay for every pixel. The entire array of amplitudes and phases determines the final shape of the output pulse. The shortest pulse is predefined as the shortest duration possible for the laser system will the longest pulse is predefined as the longest pulse that can be made with the pulse shaper. A two-pulse combination is pre-defined as the combination of an unshaped pulse with a shaped pulse. Pre-defined ultraviolet or infrared pulses at 400 or 800 nm, for example, can be used.

For the first iteration, the computer generates a number of different seed pulsed shapes with a pre-determined resolution using a random number generator. For each pulse shape, a number of mass spectra (the number of averages) are summed. The number of averages is determined by the reproducibility of the data obtained. The resulting average data is compared with the target and a success value is calculated. It is expected as the optimum pulse shape is achieved, the number of averages can be reduced because of the higher efficiency of these pulses. A number of successor pulses are chosen based on their success value and the rest of the pulse shapes are discarded. The best one is stored as the optimum. The number of "more iterations" is reset to zero; this number keeps track of how often the optimum pulse is redefined and is used to determine convergence. The success value is a number between zero and one that is assigned to each average set; this number quantifies how well the average data set approximates the target and can be obtained, for example, from a sum of the differences or a sum of the differences squared. Step A, inputting/defining the target value based on the mass, the percent of mass and minimum ion count level is very important as one wants to define regions in the spectrum to be maximized and/or minimized. This also assists in reducing background noise or interference from the mass spectrometer detections. Step B, inputting/defining the number of shots to average for each seat pulse can be set, for example, at 1000 laser beam shots for a single sample without significant degradation; this is highly advantageous over the typical 100 or less maximum shots traditionally used with prior nanosecond lasers before the specimen is unusable.

The adjustment and focusing of the shaped beam onto the sample in step J, can be performed manually or automatically by the personal computer. For example, a relatively weak diode laser, having the same wavelength as the main femtosecond laser and following the same path, can be used with a CCD camera to aim and focus the main shaped laser beam onto the sample in an automated and computer controlled, real time feedback manner. Furthermore, step L allows for a setting of delayed pulse extraction within the mass spectrometer. The calculation, comparison, and determination steps, such as those of steps N through V, are all conducted in an automatic manner within the microprocessor of the personal computer.

Step R allows the microprocessor to determine the best pulse shape with the highest success value and store it as the optimum value in the random access memory of the central processing unit. The computer will then pick approximately the ten percent best pulse shapes based on the highest success values and then reset the discarded values and automatically generate new laser pulse shapes in step V for subsequent testing iterations on the same specimen. The generation of new seed pulses is important for the success of the feedback method. The goal is to arrive at the optimum pulse in the shortest number of iterations making sure that one has searched the entire range of parameters, the global maximum. The "cost functional" refers to the statistical pressure that is placed on the optimum pulse shape in order to simplify it. For example, once an optical pulse shape or other characteristic is found, it may be important to determine how sensitive the outcome is to each of its amplitude and phase components. Perhaps a much lower resolution can produce the results. The simpler the pulse the easier it is to reproduce and interpret the results in terms of physical concepts. For certain cases, the shape can be simple enough that it can be prepared without a shaper which would allow for a less expensive alternative to the preferred pulse shaping; for example, a combination of two or three different 800 nm pulses, or a combination of infra-red and ultra-violet pulses could be employed as a modified or optimized pulse. Once statistical convergence has been determined by the personal computer, then the test is complete by determining the optimum pulse characteristics (whether they be pulse shape, pulse duration or any other such variable laser beam characteristic) for the corresponding and now post-test identified specimen.

The time scale of some of the processes that occur during MALDI may be longer than the femtoseconds pulses. In a first variation, the pulse shaper can be used to produce pulse sequences up to ten picoseconds apart. Optical delay lines can be used to increase this time delay in the nanosecond range if needed. In a second variation, the wavelength of the pulses being shaped is 800 nm. A second harmonic crystal is all that is needed to convert the wavelength to 400 nm, however, the shaper is capable of regulating the energy delivered to the sample without changing the carrier frequency (wavelength) of the laser.

The sensitivity and flexibility gained should make this unit cost effective, especially if in-source selective bond cleavage is achieved. Another variation, used to further minimize cost, provides that optimal pulse shapes may be synthesized from a combination of less expensive laser sources.

The concern of missing the MALDI crystal by using a sharply focused laser, usually observed when a weak and inexpensive laser source is used, can be overcome with the present system since it is able to use focal spots as large as a millimeter. The peak intensity of the laser will exceed $10^{11}$ W/cm$^2$, the ionization threshold due to multiphoton excitation, using 0.1 mJ per pulse focused on a 1 mm diameter spot.

Protein Sequencing

Laser desorption mass spectrometry can be employed with the present invention for identification and protein sequencing. This is significantly enhanced and made possible by the ultra-fast laser pulses and learning feedback system used. The matrix has been shown to enhance the yield of charged protein for analysis by MS detection. The matrix:phosphor diester backbone interaction has been shown to play an important role. The use of liquid matrices such as glycerol and lactic acid for IR-MALDI may bring some additional flexibility to sample preparation and delivery to the MALDI instrument. The "Ladder Sequencing" method involves a partial Edman degradation with phenyl isothiocyannate and using phenyl isoccyanate as a terminating agent. Partial enzymatic hydrolysis of polypeptides using trypsin is another strategy for protein sequencing. Trypsin digestion attaches only bonds in which the carboxyl group is contributed by either a lysine or an arginine residue. Analysis of metastable species in MALDI-PSD using a reflectron TOF spectrometer leads to valuable structural information. The introduction of 'delayed extraction' in MALDI allows improved resolution, suppression of matrix background, reduction of chemical noise, and minimization of the effect of laser intensity on performance.

Figure 11:
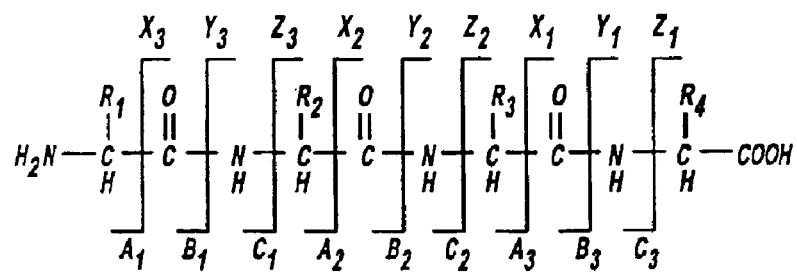
FIG. 11 is an exemplary molecular structure cleaved by the first preferred embodiment control system and apparatus.

MALDI is a soft ionization technique which produces protonated molecules that undergo very little or no subsequent fragmentation due to the low amount of energy imparted during the ionization process. Therefore, MALDI can be used to analyze mixtures of peptides because the mass spectrum of one peptide is unlikely to overlap with the spectrum of another. Ideally, cleavage of the ionized peptide at each peptide bond would provide a mass spectrum that could be interpreted, using knowledge of the masses of the amino acid residues, to deduce the sequence. However, as conceptually illustrated in FIG. 11, cleavage on either side of the I-carbon is also possible to give fragment ions, which, while diagnostically useful, also complicate the spectrum. It is also noteworthy that cleavage at any designated bond can generate either an N-terminal ion (a, b, c) or a C-terminal ion (x, y, z), the predominance of which for a protonated peptide (MH$^+$) depends on the locus of the more basic residues. In reality, the fragmentation process is more complicated than suggested in FIG. 11; for example, creation of a y-ion involves hydrogen transfer from the N-terminal side of the peptide bond and retention of the ionizing proton. In addition, there can be fragmentation of the side chain on certain residues; for example, fragmentation involving cleavage at the $h$-carbon of leucine and isoleucine generates w-ions, which distinguish these two isomeric residues.

Recognizing the ion types as represented by the appearance of peaks in the mass spectrum is not critical, as most strategies for interpretation, especially those using an algorithm, involve an iterative computational approach. However, the beginning of a C-terminal series of fragments can be distinguished from the start of an N-terminal series. The largest b-ion will be represented by a peak at high m/z value that differs from that representing MH$^+$ by a number of mass units equal to the sum of the mass of an amino acid residue plus the mass of water due to expulsion of the C-terminal residue, which contains the hydroxyl group. On the other hand, the largest y-ion is represented at a high m/z value by a peak differing from that for MH$^+$ by a number of mass units equal to only the mass of an amino acid residue.

In principle, the sequence of a peptide is deduced from a mass spectrum in which a complete series of any given ion type are represented. In practice, however, a complete series of any one type is rarely observed, but in fortunate situations, overlapping patterns of two or more incomplete series may give complete sequence information. Ideally, one would prefer to observe complementary information from series of N-terminal and C-terminal fragment ions to bolster confidence in the analysis.

Figure 8:
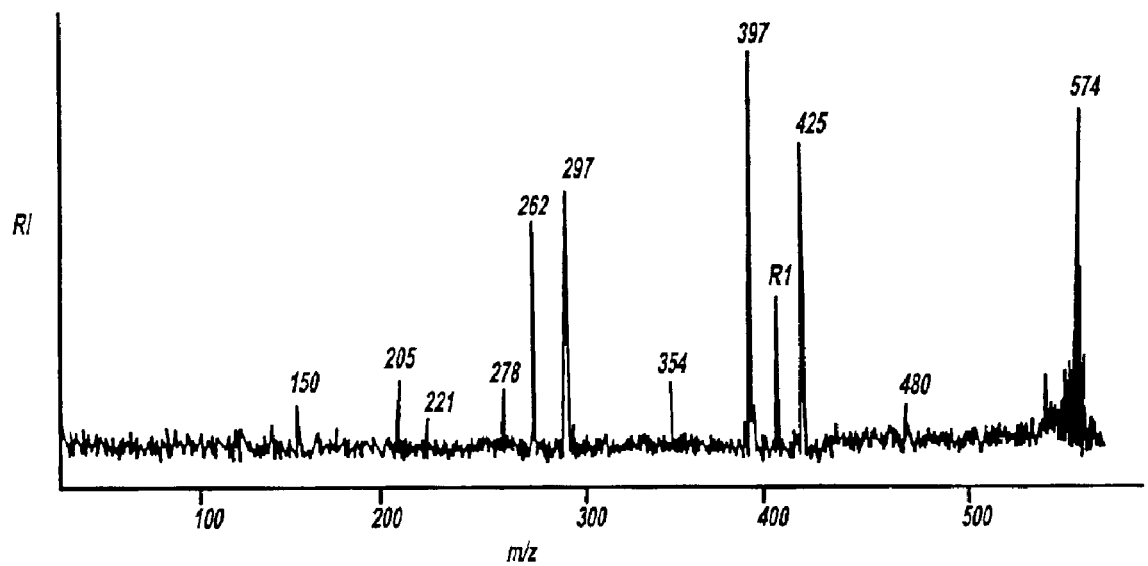
FIG. 8 is an exemplary ionization fragmentation chart employed with the first preferred embodiment control system and apparatus.

Consider the MALDI-PSD mass spectrum shown in FIG. 8 as an unknown. It can be assumed at the outset that the major peak at m/z 574 Da represents the protonated molecule, which was the precursor ion selected for PSD. The protonated molecules fragment during the PSD process and degrade into fragment ions represented by the peaks at lower m/z shown in FIG. 8. The procedure for analysis or data interpretation consists of merely examining the mass difference between each of the fragment ion peaks and the peak representing the protonated molecule. The goal is to find a fragment ion peak that differs in mass from the protonated molecule peak by either a residue mass or a residue mass plus water. A peak at a mass-to-charge (m/z) value that differs from the protonated molecule peak by the mass of a residue mass plus water corresponds to the amino acid that was located at the C-terminus of the original peptide.

In considering the mass spectrum in FIG. 8, the peak at m/z 425 corresponds to the loss of 149 Da, which corresponds to the mass residue of methionine and water; i.e., 149=131 (the residue mass in methionine)+18. The observation of the peak at m/z 425 suggest that methionine was expelled from the C-terminus to form a b ion at m/z 425. Having recognized the largest b ion in the mass spectrum by its peak at m/z 425, the goal is to identify the next smaller b ion, namely one that also has lost the second amino acid residue from the C-terminus to form the second b ion. The peak at m/z 278 represents a mass difference from 425 that corresponds to only the residue mass of an amino acid. That is, the mass difference between 425 and 278 is 147 Da, which is the residue mass of phenylalaninne. This suggests that the second amino acid in the sequence from the amino terminus is phenylalanine: -Phe-Met.

Continuing with the b series, the peak at m/z 221 is 57 u lower than 278. This mass difference corresponds to the residue mass of glycine: -Gly-Phe-Met. This observation suggests that the third amino acid from the C-terminus is a glycine residue. Finally, it can be seen that there are no other peaks observed below m/z 221 that correspond to the loss of a residue mass from 221; the search for further b ions come to a halt. At this point, the peak represents the intact molecule (the peak at m/z 574 which is the protonated peptide) and an examination of fragment ion peaks that differing in mass from 574 by exactly a residue mass to try to recognize the beginning of the y series of ions, is pursued. Upon reconsideration of this mass spectrum, one notices that the peak at m/z 411 is 163 lower than the peak at m/z 574. This corresponds to the residue mass of tyrosine. Residue loss from the protonated molecule suggests that tyrosine is the amino acid located at the amino terminus of the peptide.

With the focus now on m/z 411 as a reference point, notice that the peak at m/z 354 is 57 Da lower, a mass which corresponds to the residue of glycine. The observation of peak at m/z 354 suggests that the second amino acid from the N-terminus is a glycine residue, giving the partial sequence: Tyr-Gly-. Using the peak at m/z 354 as a reference point, the peak at m/z 297 is 57 Da lower than m/z 354 and suggests the expulsion of another residue of glycine in the formation of this ion. These observations suggest that the third amino acid residue is also a glycine residue in sequence from the N-terminus. Continuing with the peak at m/z 297 as a reference point, the peak at m/z 150 is 147 Da lower, suggesting expulsion of a phenylalanine residue or that phenylalanine is the fourth amino acid from the N-terminus, giving the partial sequence: Try-Gly-Gly-Phe-. Since there are no other peaks at lower m/z that differ from m/z 150 by a residue mass of an amino acid, recognition of the sequence comes to a halt.

Having suggested possibilities for amino acid sequences from either terminus of the peptide, these two suggested partial sequences are overlaid to compose a complete sequence. For example, the data reviewed above suggest that the sequence at the C-terminus is: -Gly-Phe-Met; whereas another series of data suggested that the series of amino acids at amino terminus was: Try-Gly-Gly-Phe-. Note that each of these two partial sequences shows the C-terminus of a glycine residue connected to the amino terminus of a phenylalanine residue. These two residues must be a redundant observation in the two sequences, and they can be overlaid at that point. This would give an overall sequence starting from the amino terminus of: Try-Gly-Gly-Phe-Met.

If the residue masses of the postulated amino acids in the complete sequence are summed, 555 Da will be the obtained value. Add 18 Da to this sum for the hydrogen at the amino terminus and the hydroxyl at the C-terminus. Then add 1 Da for the proton on the protonated molecule. This will give a total of 574 Da for the expected mass of the protonatetd molecule, in perfect agreement with the observed peak at m/z 574, giving credence to the suggested amino acid composition implicit in the sequence Y-G-G-F-M.

The protein sequencing can be conducted by use of the present invention with or without use of a matrix. The use of an ultrafast, femtosecond laser is envisioned to minimize any destructive burning of the specimen, thereby potentially rendering use of an expensive and time-consuming matrix as unnecessary. Without a matrix (herein, also known as having "isolated molecules"), the identification and sequencing of the protein is simplified since the matrix characteristics do not have to be accounted for and filtered out of the calculations. A femtosecond laser in the range of approximately 20 femtosecond duration pulses allows for localization of the energy based on the speed of the pulse and the ability to quickly shape the phase and amplitude modulation of the pulse. Furthermore, the specimen fragmentation is primarily due to laser cleavage rather than enzyme or chemical cleaving. This is ideally suitable for insoluble proteins, glycocylated proteins which have been linked to cancer, (including the selective cleavage of the associated oligosacharides) direct protein analysis from silicate substrates, direct analysis of PAGE gels, direct sampling of membrane proteins from intact cells and bacteria, the direct sampling of genetically modified agricultural produce (such as grains), and even human matter such as hair, fingernails and fingerprints.

The personal computer employs a method and software for protein sequencing as follows. The foundation of this method is based on the fact that there are only 20 amino acids and that their masses are well known. First, the computer determines the molecular weight of the intact proteins specimen. This requires the generation of a single high-mass peak and minimization of the low weight background. Secondly, the computer automatically finds peaks that are an integer number of amino acids smaller than the parent protein; a laser beam pulse shape that causes some fragmentation can be employed. Thirdly, this procedure is continued from high to low masses. Finally, confirmation of results can be automatically obtained by a statistical optimization method (such as that previously described for the MALDI process) that attempts to optimize a given mass; the success of this optimization will depend on whether that fragment of the protein has an integer number of amino acids. Automatic adjustment for the N or C terminus is also automatically adjusted for by the computer as previously explained. Alternately, each single amino acid could be separately searched for. Thus, the present invention control system and apparatus is ideally suited for analyzing, identifying, sequencing and severing complex multimolecular specimens in a highly automated manner.

Selective Bond Cleavage

The ultra-fast laser of the present invention is used to enhance in-source photochemistry and fragmentation, however, random fragmentation would not be as useful as selective bond cleavage. Furthermore, selective peptide bond cleavage would be ideal for protein sequencing. Cleavage of amino acid side chains may be of value for de novo sequencing because it would allow a determination of the presence or absence of certain amino acids. Similarly, selective cleavage of phosphate groups, oligosacharides and other post-translational modifications would be equally valuable. The ideal, of course, would be to achieve peptide bond cleavage without loss of side chains or other appended groups. This would allow, for example, to determine phosphorylation sites.

It is envisioned that selective bond cleavage can be realized when using shaped pulses that are capable of localizing the energy in a time scale that is short enough to prevent total energy randomization. For example, the protonated molecule of bradykinin potentiator C, as produced by MALDI, fragments poorly during PSD, and does not produce a suitable spectrum from which one could deduce the amino acid sequence. Thus, this 11-residue peptide is ideal for this application. Selective laser bond cleavage may have additional application as a synthetic route to specific products.

Fixed Shape Pulse Shaping Apparatus

Figure 12:
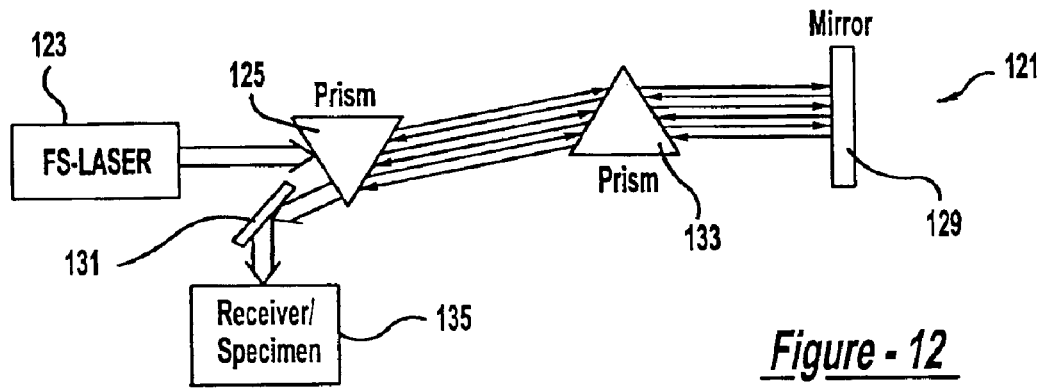
FIG. 12 is a diagrammatic view showing a second preferred embodiment of a laser excitation apparatus of the present invention.

A second preferred embodiment of a laser excitation apparatus 121 is showing in FIG. 12. Apparatus 121 includes a femtosecond laser 123, an upstream prism 125, a downstream prism 133, a pulse shaping mirror 129 at the Fourier plane, an offset mirror 131, and a receiver or targeted specimen 135. Upstream prism 125 initially acts to disperse the colors of the emitted laser beam pulse while downstream prism 133 serves to redirect this dispersed laser beam pulse toward pulse shaping mirror 129. Pulse shaping mirror 129 has a predetermined or fixed pulse shaping surface, such as a set of 800 nm wavelength sine curves, formed or machined therein. The physical characteristic or shape of the actual pulse shaping surface is predetermined through optimization experimentation for the intended use and intended laser beam input by use of a learning program such as that disclosed in the first preferred embodiment. After the desired mirror surface shape is known for the intended use, the less expensive, fixed shape mirror 129, or an alternate fixed pulse shaping optic, can be employed to reduce equipment costs for actual production systems. Also, the computer and optimization program are not required for these types of known set up and known specimen applications after the initial determination is conducted.

The passive pulse shaping mirror 129 thereby reshapes the laser beam pulse shape characteristic, reflects it back through the same prisms in reverse order, and in an offset or time-delayed manner. The position and orientation of mirror 129 alters the final characteristics of the shaped pulse. Thus, a computer controlled automatic actuator can move or change the position or orientation of mirror 129, based on an algorithm, such as shaping the pulse with the cosine portion of the sine wave shape. Offset mirror 131 subsequently reflects the shaped laser beam toward the receiver, which can be a mass spectrometer, fiber optic sensor/switch, or a targeted specimen.

It is alternately envisioned that an in-line optical apparatus can be used, such as that disclosed with the first preferred embodiment, however, the pulse shaper at the Fourier plane would be replaced by a passive mask having a transmissive optic with a predetermined coefficient of refraction, or a polarizing-type sine mask on a transparent substrate. Also, a polymer-doped glass or blend of polymer sheets that are capable of retarding the phase of the laser beam pulse wave or otherwise varying a wavelength, timing or shaping characteristic of same can be employed.

Alternately, certain optics can be used such as a backside coated, chirped mirror having multiple dichroic layers, which would be satisfactory for pulse shaping without dispersive optics and without the need for a Fourier plane. An acceptable chirped mirror is disclosed in Matuschek, et al, "Back-side-coated Chirped Mirrors with Ultra-smooth Broadband Dispersion Characteristics," *Applied Physics B*, pp. 509–522 (2000). A negative dispersion mirror from CVI Laser Corp., part no. TNM2-735-835-1037 is another suitable example. A rotatable wheel having multiple different chirped mirrors, each with specific pulse shaping characteristics, can also be used to provide a discrete number of predetermined shaped pulses.

Optical Coherence Tomography

Figure 17:
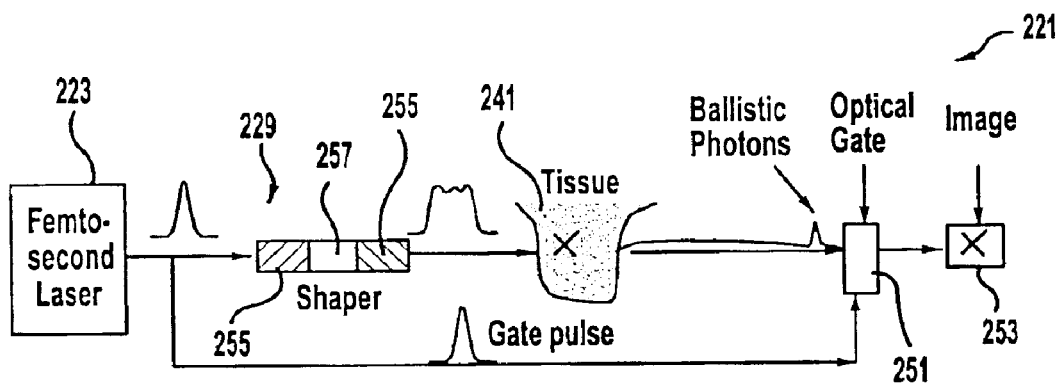
FIG. 17 is a diagrammatic view showing third and fourth preferred embodiments of the present invention laser excitation apparatus applied to optical coherence tomography and photodynamic therapy.

A third preferred embodiment of the present invention uses an apparatus 221 for laser excitation or ionization with Optical Coherence Tomography ("OCT"). In general, FIG. 17 illustrates the OCT application of apparatus 221 wherein there is a femtosecond laser 223, a laser beam shaper 229, a human or animal tissue specimen 241, an optical gate 251 and an image 253. Laser 223 emits a laser beam pulse shorter than 1 picosecond. Shaper 229 is made of three parts; two dispersive elements 255 which sandwich a phase mask element 257. Shaper 229 essentially prevents multiphoton excitation which can damage the person's or animal's DNA, as will be discussed in more detail as follows. An unshaped laser beam pulse is used to gate the ballistic photons to render the image for tomography use. Optical gating can be accomplished by up-conversion in a frequency doubling crystal or with a kerr-gate in liquid carbon disulphide. The construction of apparatus 221 as illustrated supposes transmission imaging; the same end result can alternately be accomplished with back scattered imaging. Image 253 could be viewed like an x-ray-type image of the internal organs of the human or animal specimen but without harmful three photon exposure. The use of the shaped pulse in OCT provides for an increase in laser intensity for better imaging while preventing the damaging effects caused by multiphoton excitation of healthy tissue.

Photodynamic Therapy

A fourth preferred embodiment of the present invention uses an apparatus also shown as 221 for laser excitation or ionization with photodynamic therapy ("PDT"). In general, FIG. 17 also illustrates the PDT application of apparatus 221, but optical gate 251 and image 253 are not being required. Shaper 229 allows two photon excitation but essentially prevents three photon excitation. Shaper 229 enhances the laser induced activity of a therapeutic agent which prevents damage of healthy tissue. Use of laser beam pulse shaping of the present invention should provide superior control and results for PDT applications as compared to those practically possible with conventional methods as disclosed, for example, in U.S. Pat. No. 6,042,603 entitled "Method for Improved Selectivity in Photo-Activation of Molecular Agents" which issued to Fisher et al. on Mar. 28, 2000, and is incorporated by reference herein. Alternately, the pulse shaper can be tuned to target cancerous cells for multiphoton gene therapy or destruction, with or without the presence of a therapeutic agent, without damaging healthy tissue.

Control of Nonlinear Optical Processes

As applied to all of the applications herein, selective control of one and multiphoton processes in large molecules, including proteins, is possible using simple pulse shaping. The results show an extraordinary level of control that is robust and sample independent, with contrast ratios near two orders of magnitude (clearly visible with the naked eye). Such large contrast ratios allow for more precise cancellation control of undesired photons and other laser beam characteristics, such that nonlinear transitions induced by each pulse are controlled. Because simple phase functions can be incorporated into a passive optical component such as mirror 129 (see FIG. 12), these applications do not require the complexity and expense of computer controlled pulse shapers after initial set up, although systems such as in FIG. 1 can still be employed.

Figure 13A:
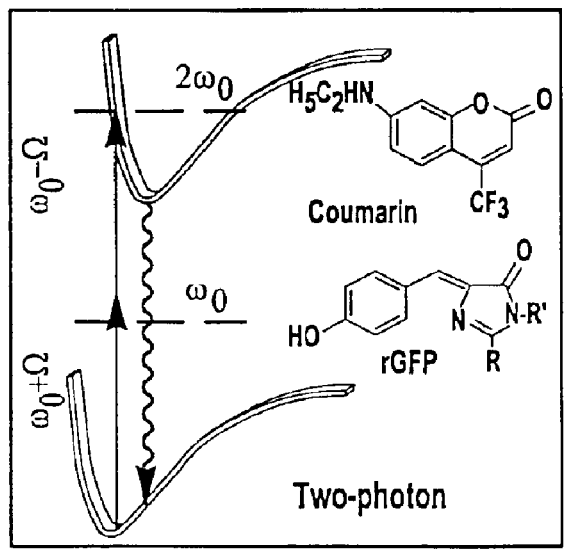
FIGS. 13A–13C are schematic and graphical representations of two photon and three photon induced fluorescence employed with the laser excitation apparatus.
Figure 13B:
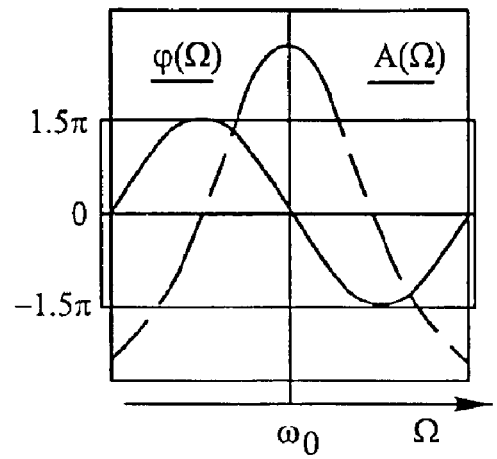
Figure 13C:
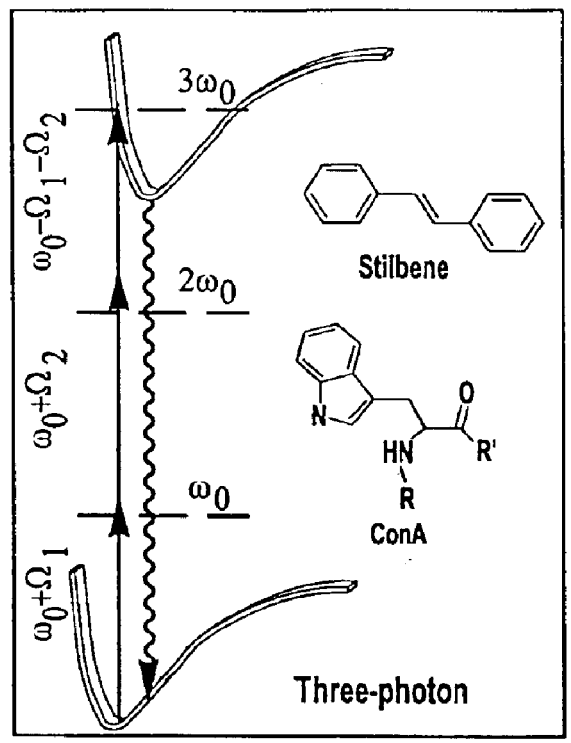

The underlying concept of the apparatus and associated method are shown in FIGS. 13A–13C. Multiphoton transitions are optimized when the central bandwidth of the laser pulse $\omega_0$, is some fraction (half for two-photons, a third for three-photons, etc.) of the total energy of the transition as illustrated in FIGS. 13A and 13C. For ultrafast pulses, when the bandwidth is large, different frequency components ($\omega_0 \pm \Omega$) of the pulse can interfere, thereby reducing the probability for multiphoton excitation. Referring to FIG. 13B, the spectrum of the ultrafast laser pulse with amplitude $A(\Omega)$ is plotted as a function of detuning from the central frequency. A phase mask $\phi(\Omega)$ can be imprinted on the pulse such that the phase of each frequency component $\Omega$ acquires a specific value. The effect of pulse shaping on the probability for two-photon absorption ("2PA") can be calculated as follows:

$$P_{2PA} \propto \left| \int_{-\infty}^{\infty} A(\Omega) A(-\Omega) \exp[i\{\varphi(\Omega) + \varphi(-\Omega)\}] d\Omega \right|^2 \quad [4]$$

and for three-photon absorption ("3PA"), a similar formula can be derived as follows:

$$P_{3PA} \propto \left| \int_{-\infty}^{\infty} \int_{-\infty}^{\infty} A(\Omega_1) A(\Omega_2) A(-\Omega_1 - \Omega_2) \exp[i\{\varphi(\Omega_1) + \varphi(\Omega_2) + \varphi(-\Omega_1 - \Omega_2)\}] d\Omega_1 d\Omega_2 \right|^2 \quad [5]$$

where amplitudes and phases are introduced for two different detuning values $\Omega_1$ and $\Omega_2$, as shown in FIG. 13C. One photon transitions are not affected by the phase of the pulses, however, one photon processes are difficult to selectively achieve at high photon flux due to the onset of multiphoton processes.

A schematic representation of two photon and three photon induced fluorescence is illustrated in FIGS. 13A and 13B, respectively. The vertical arrows represent ultrafast pulses that induce the two and three photon transitions. Because of their broad bandwidth, ultrafast pulses contain photons that are detuned from the central wavelength $\omega_0$ by an amount $\Omega$. Referring again to FIG. 13C, ultrafast laser pulses are shaped using a sine function phase mask across the pulse spectrum underlying the dashed curve while the structures of the chromophores are also shown.

EXAMPLE 1

The experiments in all of the following example were carried out using an amplified titanium sapphire laser producing 50 fs pulses. The pulses were shaped using a spatial light modulator ("SLM") at the Fourier plane of a zero-dispersion two grating arrangement. The two independent modulator plates, based on liquid crystal technology in the SLM (128 pixels each), were calibrated so that only phase delays were introduced without changes to the output spectrum, intensity, and polarization. The shaped pulses centered at 809 nm were characterized by second harmonic generation frequency resolved optical gating. When all phases were set to zero, laser pulses were near transform limited. Unless indicated otherwise, measurements were made with pulse energies of 0.4 µJ/pulse at the sample. Experiments were carried out by setting the phase function equal to a sinusoid, as shown in FIG. 13B, in the 779–839 nm spectral range. Emission from one photon or multiphoton induced processes from various samples was measured as a function of $\delta$, the phase shift of the mask across the spectrum. The maximum phase advancement or retardation was 1.5π.

Equations 4 and 5 can be used to calculate the expected signal for two and three photon processes as a function of $\delta$. These calculations are graphed in FIGS. 14A–14H for sinusoidal phase functions having a half (FIGS. 14A and 14B) or a full (FIGS. 14C and 14D) period across the entire phase mask. The calculated probability for two photon and three photon transitions peaks at half integer values of π in FIGS. 14A and 14B, while the calculated probability for two photon and three photon transitions peaks at integer values of π in FIGS. 14C and 14D. The shape of the phase function, where maxima and minima in the probability are achieved, is indicated as inserts.

Experimental data were obtained with the phase functions used for the calculations in FIGS. 14A–14D. In these experiments, the two and three photon emission from large organic molecules is detected as a function of $\delta$. Although the model described by equations 4 and 5 assumes two level systems, FIGS. 14E–14H experimentally demonstrate that this principle can be applied to complex systems having a manifold of vibrational states broadened by the presence of a solvent. It is noteworthy that the peaks and valleys predicted by equations 4 and 5 are observed in the experimental data; essentially, the intensity maxima are found when the phase function is antisymmetric with respect to the central wavelength of the pulse and minima when it is symmetric.

More specifically, theoretical and experimental phase-mask control of two and three photon induced fluorescence is shown in FIGS. 14A–14H. Equations 4 and 5 predict that as the phase mask is translated by an amount $\delta$, the probability of two ("$P_{2PA}$") and three photon transitions ("$P_{3PA}$") is modulated, as illustrated in FIGS. 14A–14D, for a half period sine mask (FIGS. 14A and 14B) and a full period sine mask (FIGS. 14C and 14D). Transform limited pulses yield a maximum value of 1. The small inserts in FIGS. 14A and 14C display the phase function at specific positions where maximum and minimum values of fluorescence take place (FIGS. 14E–14H) wherein experimental two and three photon laser induced fluorescence measured for Coumarin and Stilbene, respectively, as a function of phase mask position $\delta$ are shown. The phase masks used for these experiments were the same as those used in the calculations. Thus, the pulse shaping masks can be predetermined or fixed in shape based on calculations, experiments or learning program values for known equipment and known specimens.

EXAMPLE 2

Figure 15A:
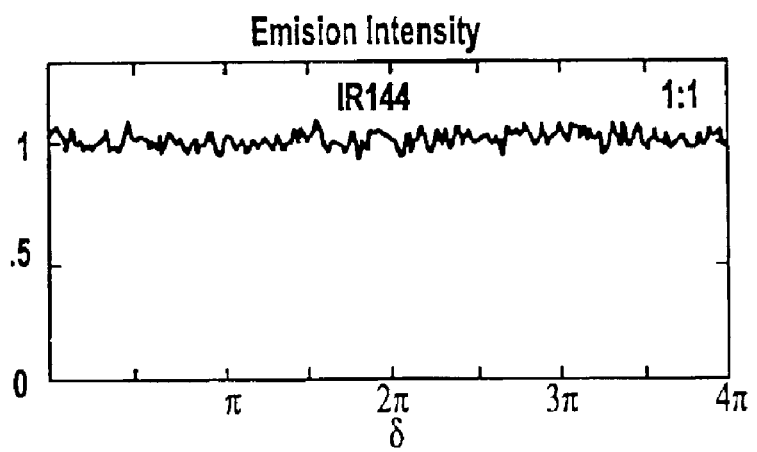
FIGS. 15A–15G are sets of laser beam pulse shapes employed with the laser excitation apparatus for two and three photon induced fluorescence.
Figure 15B:
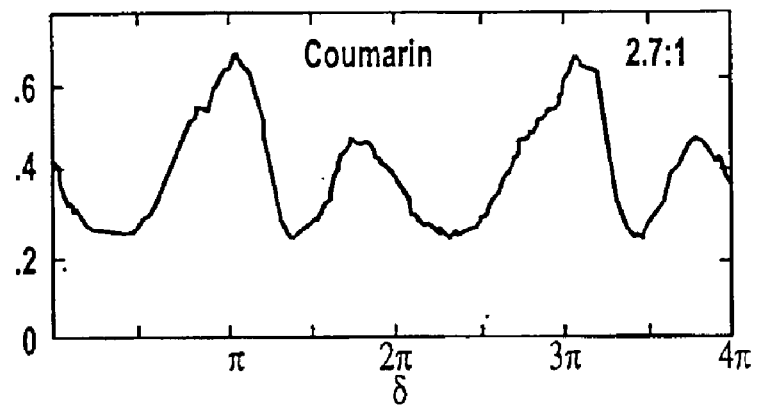
Figure 15C:
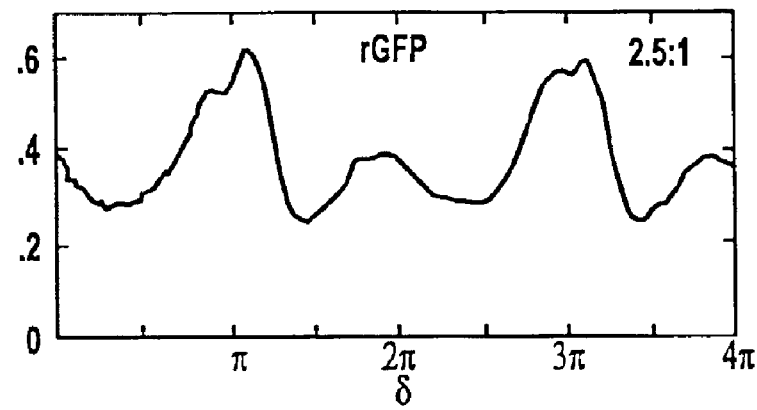
Figure 15D:
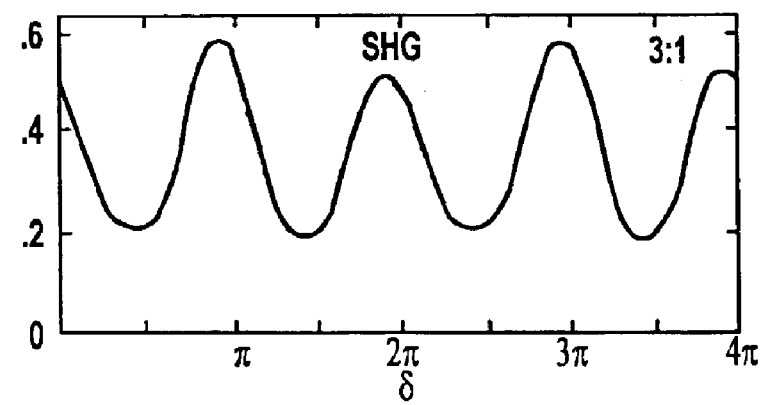

Experimental results for various samples obtained with a full-period sinusoidal phase mask are shown in FIGS. 15A–15G. FIG. 15A shows one photon laser induced fluorescence ("1PLIF") of IR144 observed at 842 nm as a function of phase mask position. This measurement was made with 0.3 nJ/pulse to avoid nonlinear processes at the specimen. It is noteworthy that one photon process in the weak field regime show no dependence on phase shaping. FIG. 15B shows results for the two photon laser induced fluorescence ("2PLIF") from Coumarin collected at 500 nm. The data in FIG. 15C shows the dependence of 2PLIF in recombinant green fluorescent protein ("rGFP") detected at 505 nm. The data in FIG. 15D corresponds to the intensity of the second harmonic generation ("SHG") signal at 405 nm from a 0.3 mm β-barium borate crystal. The maximum and minimum signal for SHG coincides with that observed for 2PLIF but is not identical.

Figure 15E:
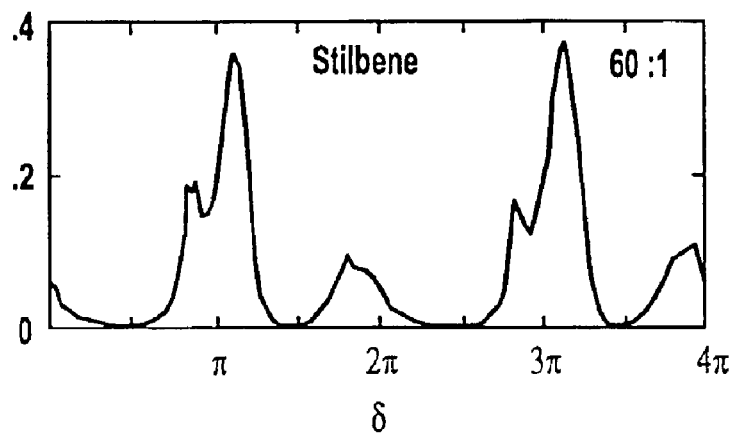
Figure 15F:
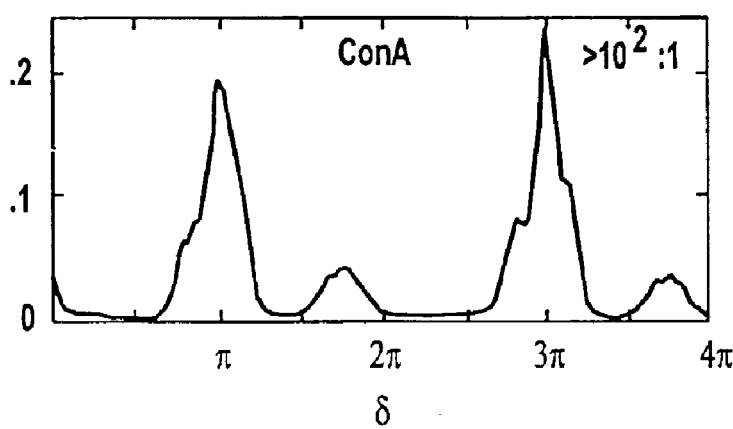
Figure 15G:
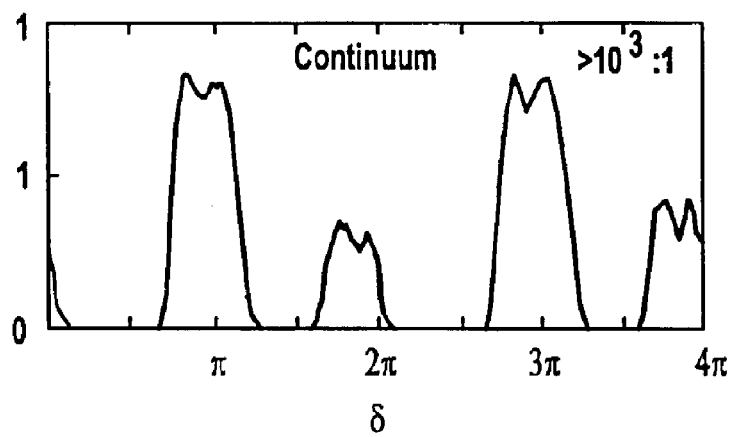

With reference to FIG. 15E, the dependence of three photon laser induced fluorescence ("3PLIF") from Trans-Stilbene is illustrated. The signal was collected at 350 nm as a function of $\delta$. In this case, the maximum contrast (max:min) is measured to be 60:1. The data in FIG. 15F corresponds to the 3PLIF from Tryptophan residues in Con A, collected at 350 nm. In 3PLIF the maximum fluorescence signal is less than that obtained for transform limited pulses (when all the phases in the mask are set equal to zero), but the overall contrast ratio over the three-photon excitation is excellent, approaching two orders of magnitude. The data in FIG. 15G corresponds to the continuum generation response (a nonlinear self-frequency modulation process yielding white light pulses) from a 3 mm slab of quartz detected at 600 nm.

More specifically, FIGS. 15A–15G demonstrate the experimental measurements of one and multi-photon emission obtained as a function of phase mask position δ. In all cases, the phase mask is a full period sine function. The signal measured with transform limited pulses is unity. The contrast ratio (max:min) is given in the upper right corner of each of the experimental plots. Here we find that the higher the order of the optical nonlinearity, the greater the contrast that we observe, therefore discrimination among different order processes is possible. In other words, the higher the order, the greater the photons, which makes it easier for photon cancellation. Also, the greater the contrast ratio, the more the background noise is filtered out.

EXAMPLE 3

FIG. 16A presents the maximum discrimination between linear and nonlinear response observed for intense pulses (0.5 μJ/pulse). Separate detectors simultaneously collected the 1PLIF from IR144 solution and a portion of the continuum output. Maximum and minimum contrast ratios of >$10^3$:1 and 1:0.6 were obtained for one photon process versus continuum, respectively, as shown in FIGS. 16A and 16B. This control is extremely valuable when one is interested in linear processes under high-flux conditions, like in laser microscopy or in optical fiber communications. Using the simple phase function discussed earlier, particular windows of opportunity to control second versus higher order processes can be employed as demonstrated in FIGS. 16C and 16D. For certain values of δ, continuum generation even for relatively high intensity laser pulses (~1 μJ/pulse) can be completely suppressed. FIGS. 16C and 16D show that maximum and minimum contrast ratios of >$10^3$:1 and 1:4 were obtained for 2PLIF versus continuum, respectively.

Two photon transitions can be achieved while suppressing three photon processes for use in two photon microscopy or in two photon PDT. This type of control is much more difficult because once multiphoton transitions take place it is very difficult to stop at a particular order. A mixture of Coumarin and Fluoranthene were prepared to explore control of 2PLIF versus 3PLIF. Because fluorescence from these two molecules overlaps the same spectral region, the separation between the two signals was achieved by temporal gating. Coumarin fluorescence was detected at 495 nm during the first 20 ns, while fluoranthene fluorescence was detected at 460 nm with a gate that opened 40 ns after the initial rise and extended for 120 ns. Maximum and minimum contrast ratios of 1.4:1 and 1:2.2 were obtained for 2PLIF versus 3PLIF, respectively, as presented in FIGS. 16E and 16F. The contrast data presented in FIGS. 16–16F were obtained when transform limited pulses yielded equal intensities for the processes. Better contrast can be obtained using additional pulse shaping as described in the following section, especially as the multiphoton processes are detuned from resonance.

Predetermined Pulse Shaping and Phase Control of Multiphoton Processes

The present invention can utilize the presently invented phenomenon of "Multiphoton Intrapulse Interference" as optimized for large molecules, proteins, and other condensed phase materials, through a combination of: (a) a chirped mask pulse shaper; and (b) a smooth function of phase versus frequency for the mask pulse shaper. The following formulas provide a predictive advantage for finding appropriate phase masks instead of using a learning program. The probability of two photon transitions can be calculated as follows for any given pulse shape:

For an electric field with a carrier frequency $\omega_0$ and a slow amplitude $E_0(t)$, $$E(t) = E_0(t)e^{-i\omega_0 t} \text{ and } E_0(t) = \frac{1}{\sqrt{2\pi}} \int_{-\infty}^{\infty} F_0(\Omega)e^{-i\Omega t}d\Omega \quad [6]$$

where the Fourier image $F_0(\Omega)$ around carrier frequency $\Omega=\omega-\omega_0$ can be written as:

$$F_0(\Omega) = \frac{1}{\sqrt{2\pi}} \int_{-\infty}^{\infty} E_0(t)e^{i\Omega t}dt, \quad [7]$$

the amplitude of two photon transition at resonance frequency ω is:

$$A_2(\omega) \propto \int_{-\infty}^{\infty} E(t)^2 e^{i\omega t}dt \quad [8]$$
$$= \int_{-\infty}^{\infty} E_0(t)^2 e^{i(\omega-2\omega_0)t}dt$$
$$= \int_{-\infty}^{\infty} E_0(t)^2 e^{i\Delta t}dt,$$

where detuning $\Delta=\omega-2\omega_0$, the probability of two photon transition is:

$$P_2(\omega) = |A_2(\omega)|^2. \quad [9]$$

Furthermore, the Fourier image of convolution is the product between Fourier images $$T(f*g) = (Tf)(Tg) \quad [10]$$

where convolution (*, function from Δ) of two functions (f) and (g) is:

$$f*g = \frac{1}{\sqrt{2\pi}} \int_{-\infty}^{\infty} f(\Omega)g(\Delta-\Omega)d\Omega. \quad [11]$$

Direct (T, function from Ω) and inverse ($T^{-1}$, function from t) Fourier images are $$T(f) = \frac{1}{\sqrt{2\pi}} \int_{-\infty}^{\infty} f(t)e^{i\Omega t}dt \text{ and } T^{-1}(f) = \frac{1}{\sqrt{2\pi}} \int_{-\infty}^{\infty} f(\Omega)e^{-i\Omega t}d\Omega. \quad [12]$$

Additionally, the relation between direct and reverse transforms is:

$$T^{-1}T(f) = TT^{-1}(f) = f. \quad [13]$$

Thus, using the inverse transform, the formula can be written as:

$$f*g = T^{-1}T(f*g) = T^{-1}[(Tf)(Tg)] \text{ or} \quad [14]$$

formula [14] in integral form is as follows:

$$\int_{-\infty}^{\infty} f(\Omega)g(\Delta-\Omega)d\Omega = \quad [15]$$
$$\int_{-\infty}^{\infty} e^{i\Delta t}\left[\left(\frac{1}{\sqrt{2\pi}}\int_{-\infty}^{\infty}f(\Omega)e^{-i\Omega t}d\Omega\right)\left(\frac{1}{\sqrt{2\pi}}\int_{-\infty}^{\infty}g(\Omega)e^{-i\Omega t}d\Omega\right)\right]dt.$$

The time-frequency transformation can be calculated. Using the of formula [7] and convolution theorem of formula [15], formula [8] to obtain the formula for two photon transitions as follows:

$$A_2(\Delta) \propto \int_{-\infty}^{\infty} E_0(t)^2 e^{i\Delta t} dt \propto \int_{-\infty}^{\infty} F_0(\Omega) F_0(\Delta - \Omega) d\Omega \quad [16]$$

This expression provides the two photon absorption amplitude given the spectrum of the laser pulse of $F_0(\Omega)$ and the detuned spectrum of the $F_0(\Delta-\Omega)$ that depends on the absorption of the sample.

The probability of three photon transitions can be subsequently calculated.

The complex amplitude of transition is:

$$A_3(\omega) \propto \int_{-\infty}^{\infty} E(t)^3 e^{i\omega t} dt = \int_{-\infty}^{\infty} E_0(t)^3 e^{i\Delta t} dt, \quad [17]$$

where detuning $\Delta = \omega - 3\omega_0$. Using the reverse Fourier presentation for the fields of formula [6], formula [17] can be rewritten as:

$$A_3(\omega) \propto \int_{-\infty}^{\infty} e^{i\Delta t} \left[ \int_{-\infty}^{\infty} F_0(\Omega) e^{-i\Omega t} d\Omega \right. \quad [18]$$
$$\left. \int_{-\infty}^{\infty} F_0(\Omega) e^{-i\Omega t} d\Omega \int_{-\infty}^{\infty} F_0(\Omega) e^{-i\Omega t} d\Omega \right] dt$$

Next, equation [18] can be rewritten using a new function $G(\Omega)$ $$A_3(\omega) \propto \int_{-\infty}^{\infty} e^{i\Delta t} \left[ \int_{-\infty}^{\infty} F_0(\Omega_1) e^{-i\Omega_1 t} d\Omega_1 \int_{-\infty}^{\infty} G(\Omega_1) e^{-i\Omega_1 t} d\Omega \right] dt, \quad [19]$$

where $G(\Omega_1)$ is defined as the kernel of the integral $$\int_{-\infty}^{\infty} G(\Omega_1) e^{-i\Omega_1 t} d\Omega_1 = \int_{-\infty}^{\infty} F_0(\Omega_1) e^{-i\Omega_1 t} d\Omega_1 \int_{-\infty}^{\infty} F_0(\Omega_1) e^{-i\Omega_1 t} d\Omega_1, \quad [20]$$

using the convolution formula [15], the following formula is obtained:

$$A_3(\omega) \propto \int_{-\infty}^{\infty} F_0(\Omega_1) G(\Delta - \Omega_1) d\Omega_1. \quad [21]$$

The Fourier image of the Reverse Fourier image of equation [20] defines the intermediate function using relationship of equation [13] and the integral form of the convolution theorem expressed in formula [15] as:

$$G(\Delta - \Omega_1) \propto \quad [22]$$
$$\int_{-\infty}^{\infty} e^{i(\Delta - \Omega_1)t} \left[ \int_{-\infty}^{\infty} F_0(\Omega_2) e^{-i\Omega_2 t} d\Omega_2 \int_{-\infty}^{\infty} F_0(\Omega_2) e^{-i\Omega_2 t} d\Omega_2 \right] dt =$$
$$\int_{-\infty}^{\infty} F_0(\Omega_2) F_0(\Delta - \Omega_1 - \Omega_2) d\Omega_2$$

The final formula for the detuned $\Delta = \omega - 3\omega_0$ three photon transition is obtained by using equations [21] and [22] after changing the order of integration:

$$A_3(\Delta) \propto \int_{-\infty}^{\infty} E_0(t)^3 e^{i\Delta t} dt \quad [23]$$
$$= \int_{-\infty}^{\infty} \cdots \int_{-\infty}^{\infty} F_0(\Omega_1) F_0(\Omega_2) F_0(\Delta - \Omega_1 - \Omega_2) d\Omega_1 d\Omega_2$$

such that the probability is:

$$P_3(\omega) = |A_3(\omega)|^2. \quad [24]$$

The method described above gave the formula for the n-photon transition by recurrence:

$$A_n(\Delta) \propto \int_{-\infty}^{\infty} E_0(t)^n e^{i\Delta t} dt \quad [25]$$
$$\propto \int_{-\infty}^{\infty} \cdots \int_{-\infty}^{\infty} F_0(\Omega_1) \ldots$$
$$F_0(\Omega_{n-1}) F_0(\Delta - \Omega_1 \ldots - \Omega_{n-1}) d\Omega_1 \ldots d\Omega_{n-1}$$

where detuning is $\Delta = \omega - n\omega_0$. Thus, $$P_n(\omega) \propto |A_n(\omega)|^2. \quad [26]$$

It is also desirable to take into account inhomogeneous broadening (as encountered in solutions and condensed phase materials). The integrated probability for the n-photon transition in molecules with spectral a density $g_n(\omega)$ with amplitude defined by formula [25] is proportional to the weighed average $$P_n = \int_{-\infty}^{\infty} g_n(\omega) |A_n(\omega)|^2 d\omega. \quad (1) \; [27]$$

Normalization for the case of transform limited laser pulse is $N_n$ and $$N_n = \int_{-\infty}^{\infty} g_n(\omega) |A_{TLn}(\omega)|^2 d\omega, \quad [28]$$

where $$A_{TLn}(\omega) = \ldots \quad [29]$$
$$\int_{-\infty}^{\infty} |F_0(\Omega_1)| \ldots |F_0(\Omega_{n-1})| |F_0(\Delta - \Omega_1 \ldots - \Omega_{n-1})| d\Omega_1 \ldots d\Omega_{n-1}.$$

Figures 18A, 18B, 18C:
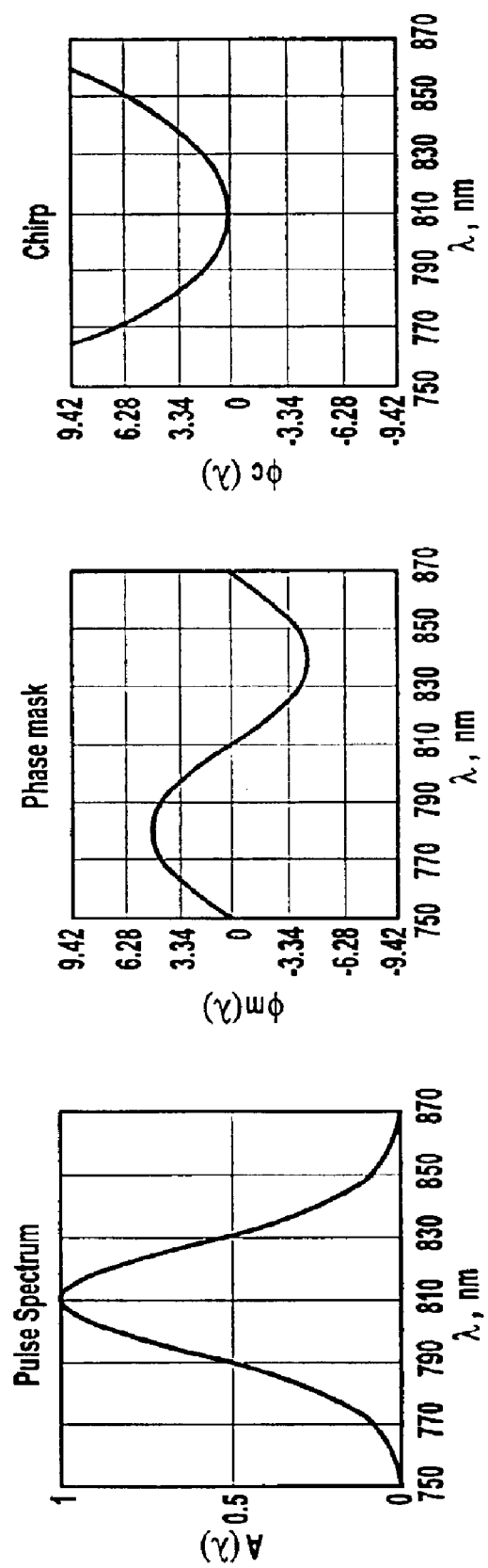
FIGS. 18A–18C are graphs showing the laser beam pulse spectrum employed with the laser excitation apparatus.

The preceding formulas [6]–[29] give the general result. The following parameters must be defined, however, for a user to define a phase mask that would minimize or maximize a particular multiphoton process. First, the laser pulse spectrum of FIG. 18A must be defined. The shorter the pulses (broader spectrum), the better the control. 45 fs pulses have been satisfactorily used but 20 or 10 fs would lead to even better results. The carrier frequency (or center wavelength) must also be defined by availability. Tuning the wavelength of the pulse could enhance certain processes but is not typically required. Secondly, the phase modulator (or alternately, the SLM, deformable mirror, chirped mirror, etc.) should cover the entire pulse spectrum and must be defined. Thirdly, a phase mask definition should be introduced. The simple sine function of FIG. 18B works remarkably well, yet other functions that can become symmetric and antisymmetric as a function of their position are also suitable. Fourthly, the addition of positive or negative linear chirp β further enhances the observed control, as expressed in FIG. 18C, and should be defined. The phase mask used in the examples presented herein is defined by $$\varphi_m(\lambda, \delta) = \varphi_a \sin\left(\frac{\lambda - \lambda_{\min}}{\lambda_{\max} - \lambda_{\min}} \cdot 2\pi N - \delta\right) \quad [30]$$

where δ is the position of the sine function (centering) across the spectrum, $\phi_a$ is the maximum phase delay, and $N_{pixel}$ is the number of pixels in the SLM, as illustrated in FIG. 18B.

When chirp is added, it can be defined by $$\phi_c(\Omega) = \tfrac{1}{2}\beta\Omega^2 \quad [31]$$

where β is the amount of linear chirp expressed in FIG. 18C. Thus, the complete phase mask with chirp is:

$$\phi(\lambda) = \phi_m(\lambda, \delta) + \phi_c(\lambda). \quad [32]$$

Figure 19B:
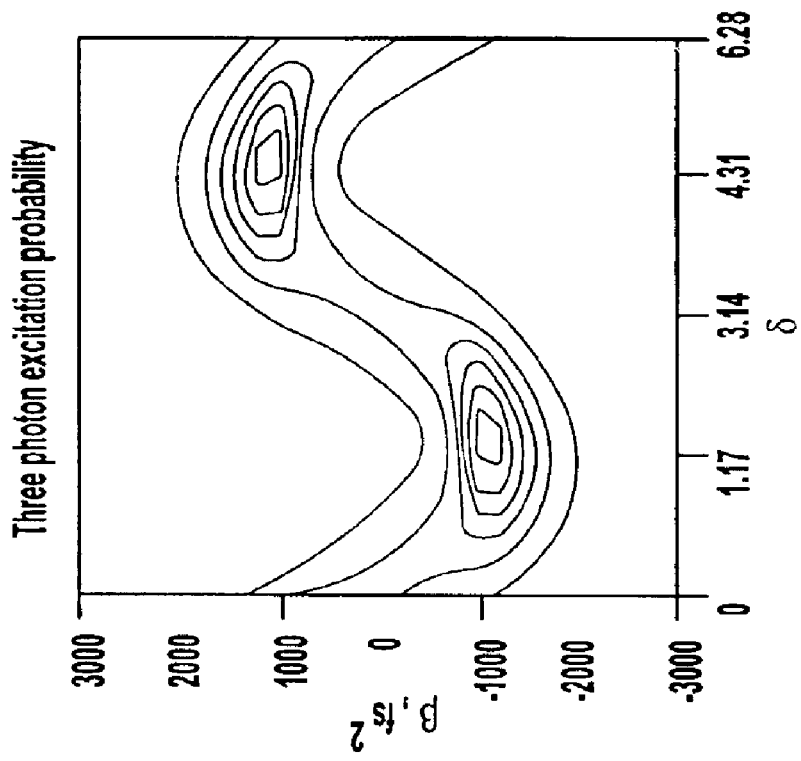
FIGS. 19A and 19B are graphs showing the calculated two and three photon absorption probability employed with the laser excitation apparatus.
Figure 19A:
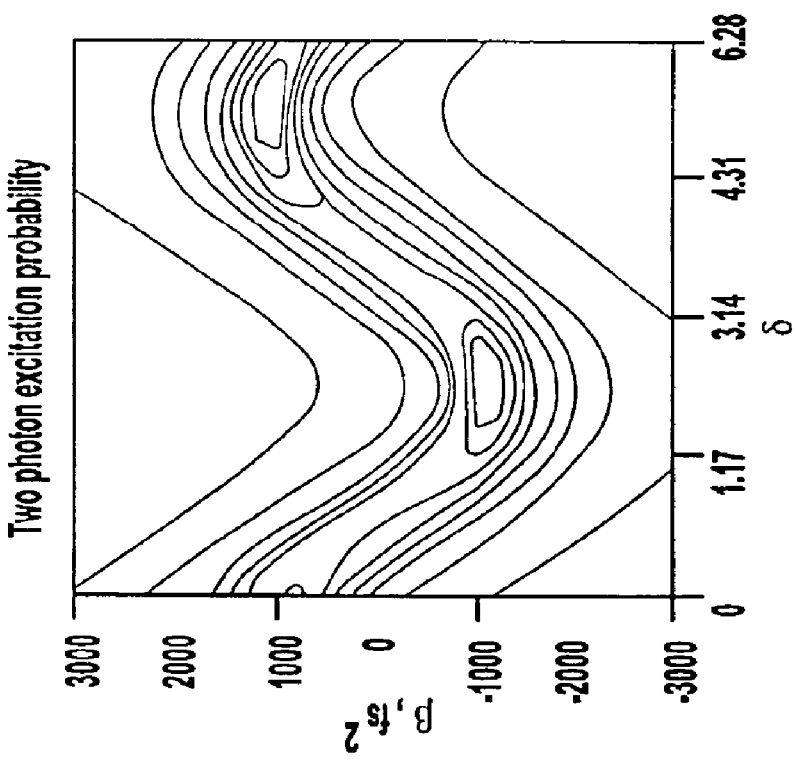
Figure 20B:
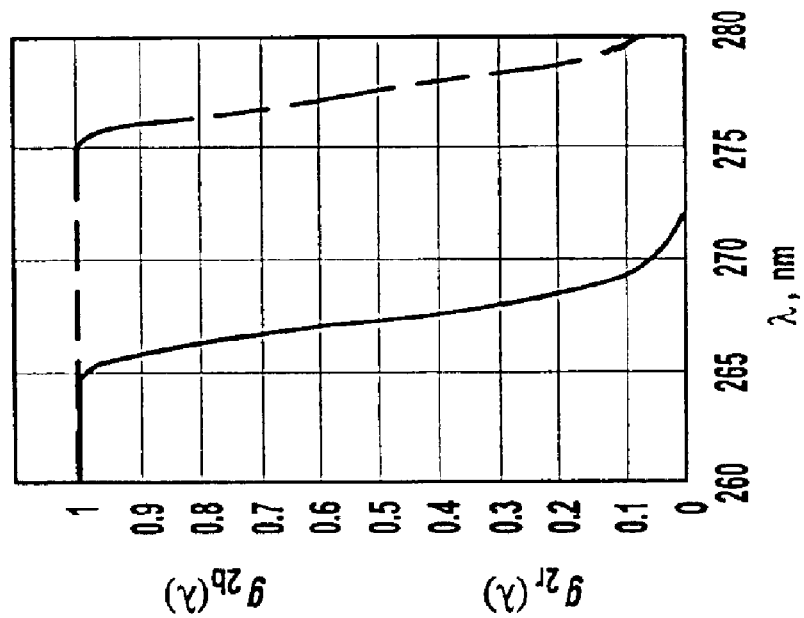
FIGS. 20A–20C are graphs showing the calculated two and three photon absorption probability employed with the laser excitation apparatus.
Figure 20A:
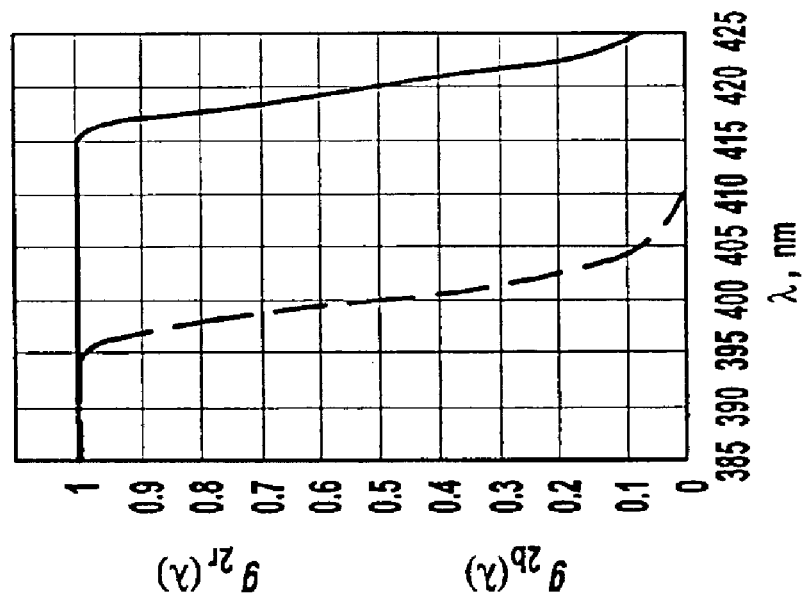
Figure 20C:
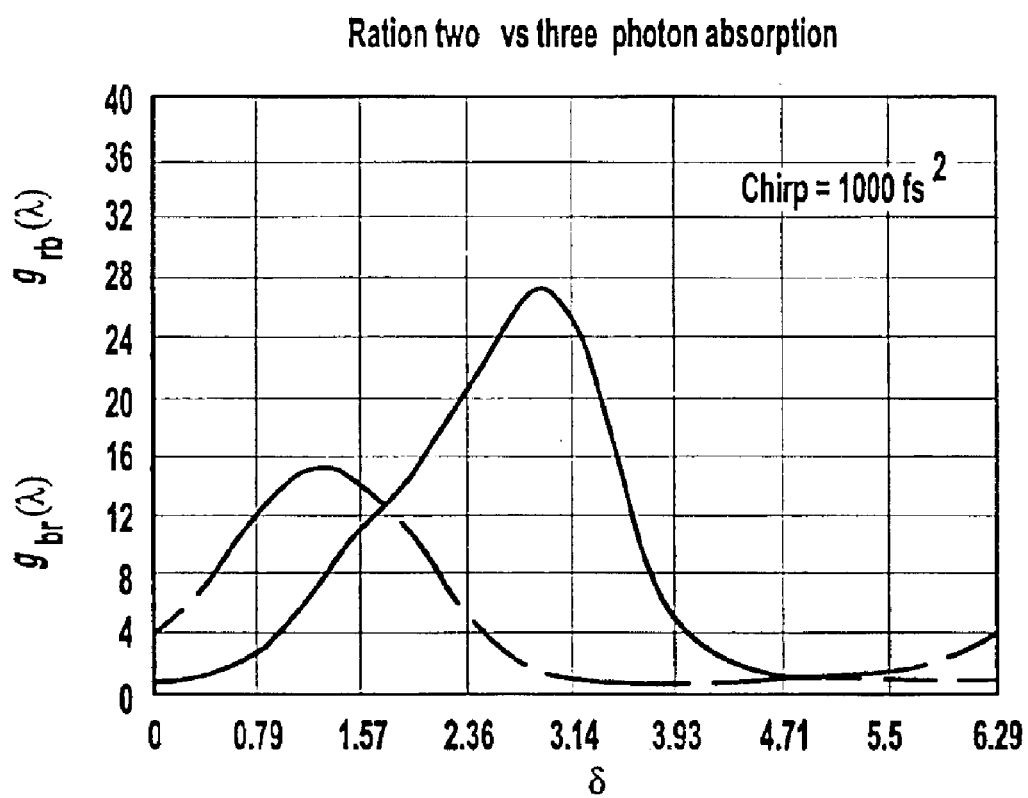

FIGS. 19A and 19B show the calculated two and three photon absorption probability using the equation presented and the absorption spectra as calculated by the dotted lines in FIGS. 20A–20C. FIG. 20C shows the calculated ration two:three photon absorption for the two different combinations of absorption spectra given in FIGS. 20A and 20B. Accordingly, robust control of multiphoton processes in molecules, proteins and nonlinear optical materials can be achieved through either adaptive, active and self optimizing learning programs and control systems, or through calculated, predetermined or fixed, passive laser beam pulse shaping devices. Therefore, inexpensive fixed phase masks can be designed before the experiment, and even without computer controlled shapers and learning programs, to control the order of multiphoton processes for large, complex molecules, proteins in photodynamic therapy, optical tomography, surgery (such as laser cutting by five or greater photon wave conveyance to maximize nonlinear energy), and photochemistry control of, for example: (a) photopolymerization (by photon pair switching to seed the process), (b) charge transfer, (c) radical reaction, (d) nucleophelic attack and (e) electrophylic attack.

Communications

Figure 21:
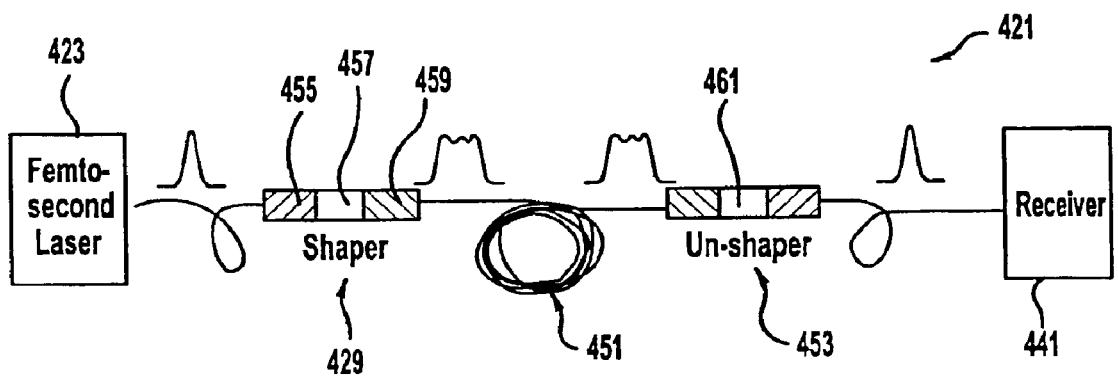
FIG. 21 is a diagrammatic view showing a fifth preferred embodiment of the present invention laser excitation apparatus applied to fiber optic communications.

With reference to FIG. 21, a fifth preferred embodiment of a laser excitation apparatus 421 of the present invention employs a femtosecond laser 423, an optical fiber 451, a laser beam pulse shaper device 429, a laser beam pulse un-shaper device 453, and a receiver 441 which includes an optical switch or sensor and the related circuitry and electrical control unit. Laser 423 emits a series of laser beam pulses, each shorter than 1 ps, into the connected fiber 451. Pulse shaper device 429 is of a predetermined mask type with a fixed pulse characteristic varying shape (such as with calculated sine wave surface shapes) and has three elements connected to fiber 451: a dispersive element 455 such as a fiber that incorporates a diffraction grating; a phase mask element 457 that can be made using a doped glass or polymer sheet; and a dispersive element 459, like element 455 but reversed, for accepting spectrally dispersed light and coupling it back to fiber 451.

The shaped laser beam pulse is capable of traveling long distances through fiber 451 without suffering nonlinear distortion because of the unique phase function imprinted or formed on shaper device 429. For example, the red color spectrum may be advanced in front of the blue color spectrum in a precise sine manner. Un-shaper device 453 subsequently reverses the phase changes introduced by shaper device 429. It is constructed the same as the shaper device but with a different phase mask element 461 that compensates for the pulse characteristic changes made by mask element 457. Alternately, an acousto-optic modulator or transient grating can be used for optical switching through constructive or destructive reference of waves. Shaping and unshaping can also be accomplished by means of a chirped mirror or spectral masks.

Thus, the present invention's ability to precisely control the laser beam pulse shape or other characteristic, especially for nonlinear or multiphoton emissions, significantly improves the quality of the communication transmission while minimizing self-focusing, self phase modulation and possible destruction of the fiber. The pulse characteristic control of ultrafast laser beam pulses, as described in all of the embodiments herein, should minimize, if not prevent, multiplicative noise effect disruption of nonlinear propagation channels in fiberoptic lines, as discussed in Mitra, et al., "Nonlinear Limits to the Information Capacity of Optical Fibre Communications," *Nature*, vol. 411, pp. 1027–1030 (Jun. 28, 2001). It is further envisioned that this type of pulse shaping apparatus can be employed within salt water oceans for submarine-to-submarine communications using shorter than 1 ps laser pulses.

While the preferred embodiment of the control system and apparatus of the present invention have been disclosed, it should be appreciated that various modifications can be made without departing from the spirit of the present invention. For example, other laser beam pulse characteristics can be varied and employed with the present invention beyond the pulse shaping and duration characteristics preferably described. Furthermore, additional software subroutines and statistical analyses can be employed. Moreover, other optical and pulse shaping devices can be used in place of those described, such as deformable mirrors and the like. Finally, analog, solid state and fiber optic electrical control circuits can be substituted for or used in addition to a microprocessor and other computer circuitry. Various optics, including lenses and mirrors, can be used to achieve collimation or focusing. Additionally, dispersive optics, such as gratings and prisms, can be interchanged. Detection of the laser induced processes may use various spectroscopic methods including laser induced fluorescence, Raman spectroscopy, nuclear magnetic resonance, gas chromatography, mass spectrometry and absorbtion spectroscopy. While various materials, specimens and components have been disclosed, it should be appreciated that various other materials, specimens and components can be employed. It is intended by the following claims to cover these and any other departures from the disclosed embodiments which fall within the true spirit of this invention.

The invention claimed is:

1. An apparatus for use with a specimen, the apparatus comprising:
    a femtosecond laser operable to emit a laser beam of less than about 50 femtosecond pulse duration upon the specimen;
    a pulse shaper operable to shape the laser beam;
    a device operable to detect characteristics of the specimen when the shaped laser beam has been emitted upon the specimen; and
    an electrical control system connected to the device and the pulse shaper, the electrical control system operably varying the pulse shaping performance of the pulse shaper for subsequent laser beam emissions based on an evaluation of the characteristics detected by the device.

2. The apparatus of claim 1 wherein the pulse shaper includes a Fourier plane.

3. The apparatus of claim 2 wherein the pulse shaper further includes at least one collimating optic and a dispersive optic.

4. The apparatus of claim 3 wherein the pulse shaper includes a second collimating optic and a second dispersive optic, wherein the Fourier plane is optically located between the collimating optics.

5. The apparatus of claim 1 wherein the specimen is a protein.

6. The apparatus of claim 5 wherein the electrical control system determines the protein sequence of the specimen.

7. The apparatus of claim 5 wherein the laser beam selectively cleaves bonds in the specimen.

8. The apparatus of claim 5 wherein there is direct laser desorption of the protein specimen free of a matrix.

9. The apparatus of claim 1 wherein the device is a mass spectrometer.

10. The apparatus of claim 9 wherein matrix-assisted laser desorption ionization, post-source decay mass spectrometry is employed to analyze the specimen by the mass spectrometer and electrical control system.

11. The apparatus of claim 1 wherein the pulse shaper includes an acousto-optic modulator operable to control amplitude and phase of the laser beam.

12. The apparatus of claim 11 wherein the acousto-optic modulator includes an anti-reflection coated Tellurium Dioxide crystal with a piezo-electric transducer.

13. The apparatus of claim 1 wherein the pulse shaper includes a liquid crystal display operable to control amplitude and phase of the laser beam.

14. The apparatus of claim 1 wherein the pulse shaper includes a deformable mirror.

15. The apparatus of claim 1 wherein the electrical control system automatically determines the most desirable laser beam pulse shape based on prior device results using substantially randomly employed pulse shapes.

16. The apparatus of claim 1 wherein the femtosecond laser operably transmits a laser beam of less than 11 femtosecond duration.

17. The apparatus of claim 1 wherein the specimen is multi-molecular.

18. A system for use with a sample, the system comprising:
laser beam pulses operably emitted upon the sample; and
a pulse shaper operable to vary shapes of the laser beam pulses;
wherein the shaped laser beam pulses selectively cleave atomic bonds in the sample.

19. The system of claim 18 further comprising a laser operably emitting the laser beam pulses with less than 50 femtosecond durations.

20. A system for use with a sample, the system comprising:
laser beam pulses operably emitted upon the sample;
a pulse shaper operable to vary shapes of the laser beam pulses;
wherein the shaped laser beam pulses chemically modify the sample; and
an electric control system operably causing the pulse shaper to vary the laser beam pulse shapes based on modification results in an automatic manner.

21. The system of claim 20 wherein the shaped laser beam pulses selectively cleave atomic bonds in the sample.

22. The system of claim 20 wherein chemical bonds are selectively cleaved in the sample.

23. The system of claim 20 further comprising a laser operably emitting the laser beam pulses with less than 50 femtosecond durations.

24. A system comprising:
a specimen substrate having molecules;
at least one laser beam pulse operably emitted upon the molecules; and
a pulse modification device operably changing an excitation characteristic of the emitted pulse;
wherein the modified laser beam pulse causes desorption of and assists with identification of the molecules.

25. The system of claim 24 wherein the specimen does not use a matrix between the molecules, and the pulse modification device is a pulse shaper.

26. The system of claim 24 wherein at least some of the molecules are substantially unknown prior to the identification.

27. The system of claim 24 wherein the molecules include a protein.

28. The system of claim 24 wherein the pulse has a duration of less than fifty one femtoseconds.

29. A system for use with a sample, the system comprising:
a laser operable to emit a laser beam pulse upon the sample;
a mass spectrometer operable to analyze ionization of the sample; and
an electrical control system operable to cause the laser beam pulse to be modified prior to it being received by the sample, the electrical control system further modifying and substantially optimizing at least one characteristic of subsequent laser beam pulses in an automatic manner.

30. The system of claim 29 wherein the modification and optimization includes a laser beam pulse having a combination of pulse durations determined by the electrical control system.

31. The system of claim 29 wherein the modification and optimization includes a laser beam pulse having a combination of pulse shapes determined by the electrical control system.

32. The system of claim 29 wherein the modification and optimization includes a laser beam pulse having a combination of pulse wavelengths determined by the electrical control system.

33. The system of claim 29 wherein the pulse has a duration of less than fifty one femtoseconds.

34. A control system for use with a specimen, the system comprising:
a laser operable to emit a laser beam upon the specimen;
a pulse shaper operable to shape the laser beam;
a detection device operable to detect characteristics of the specimen when the shaped laser beam has been emitted upon the specimen; and
a control device connected to the detection device and the pulse shaper;
the control device automatically varying the pulse shapes for subsequent laser beam emissions based at least in part on at least one signal generated by the detection device;
the control device operably comparing a target to each pulse shape result as detected by the detection device;
the control device operably causing the laser to emit laser beam pulses and the pulse shaper to transmit subsequent sets of varying pulse shapes, the results of which are then compared to at least one of the pulse shape results of the prior iterations; and
the control device operably determining if statistical convergence has been obtained from repeated pulse shape set iterations.

35. The system of claim 34 wherein the laser operably transmits a laser beam of less than about 20 femtosecond duration.

36. The system of claim 34 wherein the detection device is part of a matrix-assisted laser desorption ionization, post-source decay system and the detection device is a mass spectrometer, and the control device includes a microprocessor.

37. The system of claim 34 wherein the specimen is a protein and the control device assists in determining a sequence of the protein.

38. The system of claim 34 wherein the control device varies the laser beam emission in an adaptive manner.

39. A system for use with living tissue, the system comprising:
 a high peak intensity laser beam pulse; and
 a device operable to change a characteristic of the pulse prior to emission of the pulse upon the living tissue;
 wherein nonlinear transitions induced by each pulse are controlled.

40. The system of claim 39 wherein the device uses a pulse shaper and the desired eradicated substances in the tissue undergo two photon absorbtion.

41. The system of claim 39 wherein the pulse has a duration of less than fifty one femtoseconds.

42. The system of claim 39 further comprising generating an optical tomography image produced by the shaped pulse passing through the tissue.

43. A system for use with living tissue, the system comprising:
 a laser beam pulse; and
 a device operable to change a characteristic of the pulse prior to emission of the pulse upon the living tissue;
 wherein nonlinear transitions induced by each pulse are controlled; and
 wherein the device includes a pulse shaper which enhances two photon absorbtion by a therapeutic substance and substantially prevents three photon induced damage of adjacent healthy tissue.

44. The system of claim 43 wherein the pulse has a duration of less than fifty one femtoseconds.

45. A system for use with living tissue, the system comprising:
 a laser beam; and
 a device operable to change a characteristic of the pulse prior to emission of the pulse upon the living tissue;
 wherein nonlinear transitions induced by each pulse are controlled; and
 wherein the device includes a chirped phase mask modifying the pulse.

46. The system of claim 45 wherein the pulse has a duration of less than fifty one femtoseconds.

47. A system for use with living tissue, the system comprising:
 a laser beam pulse; and
 a device operable to change a characteristic of the pulse prior to emission of the pulse upon the living tissue;
 wherein nonlinear transitions induced by each pulse are controlled; and
 wherein the pulse is shaped to enhance targeted mutliphoton damage to modify or destroy certain molecules in the living tissue.

48. The system of claim 47 wherein the pulse has a duration of less than fifty one femtoseconds.

49. A method of ionizing and determining a characteristic of a specimen, the method comprising:
 (a) emitting a laser beam having a pulse duration of less than about 51 femtoseconds;
 (b) shaping the laser beam pulse;
 (c) sensing a characteristic of the specimen after the laser beam pulse has ionized at least a portion of the specimen;
 (d) varying laser beam pulse shapes emitted upon the specimen for subsequent iterations;
 (e) sensing characteristics of the specimen after the laser beam has ionized at least a portion of the specimen for the subsequent iterations; and
 (f) comparing the sensed results.

50. The method of claim 49 further comprising determining a protein sequence of the specimen based at least in part on the sensed characteristics.

* * * * *

UNITED STATES PATENT AND TRADEMARK OFFICE
CERTIFICATE OF CORRECTION

| | | |
|---|---|---|
| PATENT NO. | : 7,105,811 B2 | |
| APPLICATION NO. | : 10/628874 | |
| DATED | : September 12, 2006 | |
| INVENTOR(S) | : Marcos Dantus and Vadim V. Lozovoy | |

It is certified that error appears in the above-identified patent and that said Letters Patent is hereby corrected as shown below:

ON THE TITLE PAGE, under No. (54), Title "OF" should be --OR--.

ON THE TITLE PAGE, under No. (56), References Cited, Other Publications, page 2, column 1, line 7, Reference No. 2, "Leters" should be --Letters--.

ON THE TITLE PAGE, under No. (56), References Cited, Other Publications, page 3, column 1, line 22, Reference No. 6, "2000" should be --2002--.

ON THE TITLE PAGE, under No. (56), References Cited, Other Publications, page 3, column 2, line 17, Reference No. 5, "by use to" should be --by use of--.

ON THE TITLE PAGE, under No. (56), References Cited, Other Publications, page 4, column 1, line 16, Reference No. 5, "Characteriziang" should be --Characterizing--.

ON THE TITLE PAGE, under No. (56), References Cited, Other Publications, page 4, column 2, line 20, Reference No. 5, "pp. 1584-1598" should be --pp. 1584-1589--.

ON THE TITLE PAGE, under No. (56), References Cited, Other Publications, page 4, column 2, line 29, Reference No. 8, "Roer" should be --Roger--.

ON THE TITLE PAGE, under No. (56), References Cited, Other Publications, page 4, column 2, line 40, Reference No. 11, "Greutzmacher" should be --Gruetzmacher--.

ON THE TITLE PAGE, under No. (56), References Cited, Other Publications, page 5, column 2, line 36, Reference No. 10, "Physic" should be --Physics--.

ON THE TITLE PAGE, under No. (56), References Cited, Other Publications, page 6, column 1, line 28, Reference No. 10, "197" should be --107--.

ON THE TITLE PAGE, under No. (56), References Cited, Other Publications, page 6, column 2, line 12, Reference No. 4, "Redfiled" should be --Redfield--.

UNITED STATES PATENT AND TRADEMARK OFFICE
CERTIFICATE OF CORRECTION

PATENT NO.      : 7,105,811 B2
APPLICATION NO. : 10/628874
DATED           : September 12, 2006
INVENTOR(S)     : Marcos Dantus and Vadim V. Lozovoy It is certified that error appears in the above-identified patent and that said Letters Patent is hereby corrected as shown below:

ON THE TITLE PAGE, under No. (56), References Cited, Other Publications, page 8, column 2, line 54, Reference No. 16, "mid-tR" should be --mid-IR--.

ON THE TITLE PAGE, under No. (56), References Cited, Other Publications, page 10, column 2, line 20, Reference No. 7, "Relization" should be --Realization--.

ON THE TITLE PAGE, under No. (56), References Cited, Other Publications, page 10, column 2, line 58, Reference No. 18, "pp. 5508-511" should be --pp. 5508-5511--.

ON THE TITLE PAGE, under No. (56), References Cited, Other Publications, page 11, column 1, line 16, Reference No. 5, "precision" should be --precession--.

ON THE TITLE PAGE, under No. (56), References Cited, Other Publications, page 11, column 2, line 34, Reference No. 10, "Frquency" should be --Frequency--.

Column 1, line 2, "OF" should be --OR--.

Column 4, line 60, after "the", delete "to".

Column 5, line 24, after "few", delete "to".

Column 11, line 4, "femtoseconds" should be --femtosecond--.

Column 16, line 63, "$\phi$" should be --$\varphi$--.

Column 19, line 49, "FIGS. 16-16F" should be --FIGS. 16A-16F--.

Column 21, line 2, after "the", insert --spectral presentation--.

Column 21, line 3, after "[8]", insert --can be written--.

UNITED STATES PATENT AND TRADEMARK OFFICE
CERTIFICATE OF CORRECTION

PATENT NO. : 7,105,811 B2
APPLICATION NO. : 10/628874
DATED : September 12, 2006
INVENTOR(S) : Marcos Dantus and Vadim V. Lozovoy It is certified that error appears in the above-identified patent and that said Letters Patent is hereby corrected as shown below:

Column 21, line 13, after "absorption", insert --spectrum--.

Column 21, line 41, after "$d\Omega_1$," insert --and--.

Column 28, line 1, Claim 45, after "beam", insert --pulse--.

Signed and Sealed this

Sixteenth Day of June, 2009

JOHN DOLL
*Acting Director of the United States Patent and Trademark Office*